US009776992B2

(12) United States Patent
Brooks et al.

(10) Patent No.: US 9,776,992 B2
(45) Date of Patent: Oct. 3, 2017

(54) 1-OXO-1,2-DIHYDROISOQUINOLIN-7-YL-(5-SUBSTITUTED-THIOPHEN-2-YL)-SULFONAMIDE COMPOUNDS, FORMULATIONS CONTAINING THOSE COMPOUNDS, AND THEIR USE AS AICARFT INHIBITORS IN THE TREATMENT OF CANCERS

(71) Applicant: Eli Lilly and Company, Indianapolis, IN (US)

(72) Inventors: Harold Burns Brooks, Carmel, IN (US); Robert Dean Dally, Carmel, IN (US); Timothy Barrett Durham, Indianapolis, IN (US); Kevin Robert Fales, Avon, IN (US); Kwame Frimpong, Indianapolis, IN (US); Jefferson Ray McCowan, Indianapolis, IN (US); Frank George Njoroge, Carmel, IN (US); Timothy Alan Shepherd, Indianapolis, IN (US); Chong Si, Zionsville, IN (US); Kenneth Jeff Thrasher, Indianapolis, IN (US); James Lee Toth, Knightstown, IN (US); Zhipei Wu, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/518,787

(22) PCT Filed: Nov. 24, 2015

(86) PCT No.: PCT/US2015/062391
§ 371 (c)(1),
(2) Date: Apr. 13, 2017

(87) PCT Pub. No.: WO2016/089670
PCT Pub. Date: Jun. 9, 2016

(65) Prior Publication Data
US 2017/0233378 A1 Aug. 17, 2017

Related U.S. Application Data

(60) Provisional application No. 62/086,357, filed on Dec. 2, 2014.

(51) Int. Cl.
*C07D 409/12* (2006.01)
*C07D 409/14* (2006.01)
*C07C 211/07* (2006.01)

(52) U.S. Cl.
CPC .......... *C07D 409/14* (2013.01); *C07C 211/07* (2013.01); *C07D 409/12* (2013.01)

(58) Field of Classification Search
CPC .... C07D 409/12; C07D 409/14; C07C 211/07
See application file for complete search history.

(56) References Cited

U.S. PATENT DOCUMENTS 6,525,050 B1 * 2/2003 Romines, III ....... C07D 409/14
514/235.8

FOREIGN PATENT DOCUMENTS

| GB | 2188319 A | 9/1987 |
| WO | 00/13688 | 3/2000 |
| WO | 2013/027168 A1 | 2/2013 |

OTHER PUBLICATIONS

Allegra, C., "Inhibition of phosphorisbosylaminoimidazolecarboxamide transformylase by methotrexate and dihydrofolic acid polyglutamates", Biochemistry vol. 82, pp. 4881-4885 (Aug. 1985).
Shih, C. Multiple Folate Enzyme Inhibition: Mechanism of a Novel Pyrrolopyrimidine-Based Antifolate LY231514 (MTA), Advanced Enzyme Regulation, vol. 38, pp. 135-152 (1998).
Shih C., "LY231514, a Pyrrolo[2,3-d]pyrimidine-based Antifolate That Inhibits Multiple Folate-requiring Enzymes", Cancer Research, vol. 57, pp. 1116-1123, (Mar. 1997).
Budzik, G., "Effects of Methotrexate on Nucleotide Pools in Normal Human T Cells and the Cem T Cell Line", Life Sciences, vol. 66, No. 23, pp. 2297-2307 (2000).
Smolenska, Z., "Effect of Methotrexate on blood purine and pyrimidine levels in patients with rheumatoid arthritis", Rheumatology, vol. 38 pp. 997-1002 (1999).
Cheong, C. "Crystal Structures of Human Bifunctional Enzyme Aminoimidazole-4-carboxamide Ribonucleotide Transformylase/IMP Cyclohydrolase in Complex with Potent Sulfonyl-containing Antifolates*", The Journal of Biological Chemistry, vol. 279, No. 17, pp. 18034-18045 (2004).
Li, C. "Virtual Screening of Human 5-Aminoimidazole-4-carboxamide Ribonucleotide Transformylase against the NCI Diversity Set by Use of AutoDock to Identify Novel Nonfolate Inhibitors", Journal of Medicinal Chemistry, vol. 47, pp. 6681-6690 (2004).
Yagi, N. "Synthesis of N-substituted 7-acylamino-3-phenylisocarbostyril and 6-phenylbenzimidazo [2,1-a] isoquinoline Derivatives and their Fluorescent Spectra", Journal of Synthetic Organic Chemistry, Japan, vol. 75, No. 1, pp. 51-58 (1969).
Wang, Y., "Novel 5-Substituted Pyrrolo[2,3-d]pyrimidines as Dual Inhibitors of Glycinamide Ribonucleotide Formyltransferase and 5-Aminoimidazole-4-carboxamide Ribonucleotide Formyltransferase and as Potential Antitumor Agents", Journal of Medicinal Chemistry.
Kompis, I., "DNA and RNA Synthesis: Antifolates" Chemistry Review, vol. 105, pp. 593-620 (2005).
Faessel, H. "Super in Vitro Synergy between Inhibitors of Dihydrofolate Reductase and Inhibitors of Other Folate-requiring Enzymes: The Critical Role of Polyglutamylation", Cancer Research, vol. 58, pp. 3036-3050, (1998).

* cited by examiner

Primary Examiner — Timothy R Rozof
(74) Attorney, Agent, or Firm — John C. Demeter

(57) ABSTRACT

1-Oxo-1,2-dihydroisoquinolin-7-yl-(5-substituted-thiophen-2-yl)-sulfonamide compounds, formulations containing those compounds, and their use as AICARFT inhibitors.

8 Claims, No Drawings

1-OXO-1,2-DIHYDROISOQUINOLIN-7-YL-(5-SUBSTITUTED-THIOPHEN-2-YL)-SULFONAMIDE COMPOUNDS, FORMULATIONS CONTAINING THOSE COMPOUNDS, AND THEIR USE AS AICARFT INHIBITORS IN THE TREATMENT OF CANCERS

The mammalian folic acid metabolism cycle is a complex but important process for the transfer of one-carbon unit biomolecules. Folic acid cannot be synthesized but is obtained through diet. Dietary folic acid is the starting material for the cycle's fundamental molecule tetrahydrofolic acid (tetrahydrofolate, THFA). One function of folic acid metabolism is the support of DNA synthesis and repair through the generation of nucleic acid building blocks. This metabolic process includes the de novo synthesis of deoxythymidine monophosphate (dTMP) from deoxyuridine monophosphate (dUMP) through the addition of a methyl group by the enzyme thymidylate synthase with subsequent phosphorylation to the deoxynucleotide triphosphate. Purine nucleotide de novo biosynthesis begins with the activated sugar 5-phosphoribosyl-1-pyrophosphate (PRPP). Through a series of reactions, also including tetrahydrofolate, this pathway affords inosine 5'-monophosphate (IMP). IMP may subsequently be converted into either adenosine monophosphate (AMP) or guanosine monophosphate (GMP).

One step in the IMP purine de novo synthesis pathway is catalyzed by the enzyme 5-aminoimidazole-4-carboxamide ribonucleotide formyltransferase (AICARFT). AICARFT catalyzes the formylation of 5-aminoimidazole-4-carboxamide-1-β-D-ribofuranosyl-5'-monophosphate (ZMP) to 5-formylaminoimidazole-4-carboxamide ribonucleotide (FAICAR) by $N^{10}$-formyl-tetrahydrofolate (10-formyltetrahydrofolate; 10-CHO-THFA). Purine nucleotide functions include proliferation and self-renewal. Because of the importance of purine nucleotides in the synthesis of RNA and DNA, and consequent cell division and proliferation by both normal and malignant cells, the purine biosynthetic pathway has long been considered an attractive target for anticancer drug development.

Interference with folate metabolism has a greater toxic effect on rapidly dividing cells than on normally dividing cells. Because folate metabolism is required for cell replication and survival, compounds that are metabolic inhibitors have been used as antitumor therapeutics, although with toxicity and limited application. Aminoopterin, methotrexate, ralitrexed (not available in the United States), pralatrexate, and pemetrexed are examples of folic acid analogues (antifolates). The chemotherapeutic agent 5-fluorouracil, although not considered a folic acid analogue, is also an antitumor therapeutic that is a folate metabolism inhibitor.

Although not considered their primary mechanism of action, methotrexate and pemetrexed are both reported to demonstrate AICARFT inhibitory activity. Further, compounds reported to be useful as AICARFT inhibitors are provided in WO 2000/13688. Nevertheless, to date, no commercial AICARFT inhibitor chemotherapeutic agents have emerged.

There is a need to find compounds having primarily AICARFT inhibitory activity over other enzymes in the folate metabolic pathway. There is a further need to find compounds that may contribute to IMP pathway signaling inhibitory activity generally, and particularly to AICARFT inhibitory activity.

One aspect of the invention is AICARFT inhibitor compounds of Formula I:

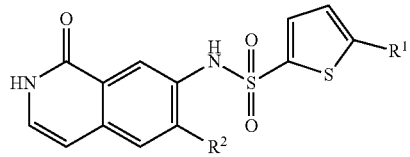

wherein:
$R^1$ is selected from the group:

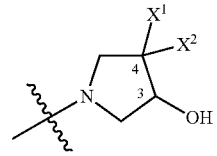

wherein each of $X^1$ and $X^2$ is independently selected from hydrogen, fluoro, or —$CH_3$; or one of $X^1$ and $X^2$ is selected from —OH, —$OCH_3$, —$N(CH_3)_2$ or morpholin-4-yl and the other is hydrogen;

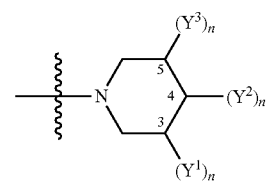

wherein each n is independently selected from 0, 1 or 2; $Y^1$, $Y^2$ and $Y^3$ are independently selected from hydrogen, —OH, fluoro, —$NH_2$, or —$CF_3$; provided all are not hydrogen; and
provided all n's are not simultaneously 0; and further provided only one n may be 2; and when one n is 2, each of $Y^1$, $Y^2$ and $Y^3$ are independently selected from fluoro, —OH, or —$CF_3$;

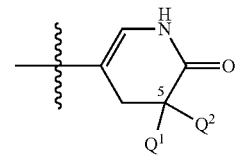

wherein $Q^1$ and $Q^2$ are independently selected from hydrogen, —$CH_3$ or —$CH_2CH_3$;

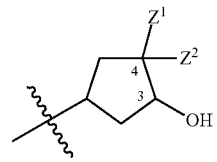

wherein each of $Z^1$ and $Z^2$ is independently selected from hydrogen or fluoro;

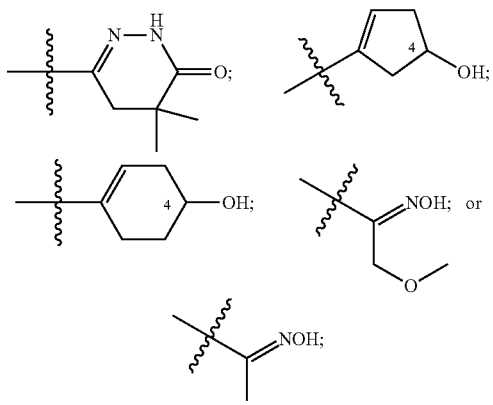

$R^2$ is hydrogen or fluoro;
or a pharmaceutically acceptable salt thereof.

A further aspect of the invention provides compounds of Formula I wherein:
$R^1$ is selected from the group:

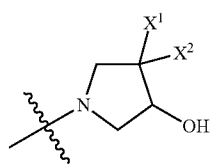

wherein each of $X^1$ and $X^2$ is independently selected from hydrogen, fluoro, or —CH$_3$; or one of $X^1$ and $X^2$ is selected from —OH, —OCH$_3$, —N(CH$_3$)$_2$ or morpholin-4-yl and the other is hydrogen;

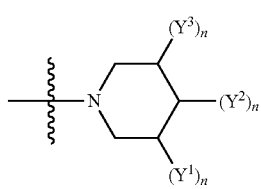

wherein each n is independently selected from 0, 1 or 2; $Y^1$, $Y^2$ and $Y^3$ are independently selected from hydrogen, —OH, fluoro, —NH$_2$, or —CF$_3$; provided all are not hydrogen; and
provided all n's are not simultaneously 0; and further provided only one n may be 2; and when one n is 2, each of $Y^1$, $Y^2$ and $Y^3$ are independently selected from fluoro, —OH, or —CF$_3$;

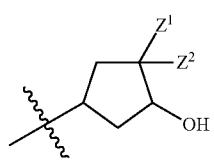

wherein each of $Z^1$ and $Z^2$ is independently selected from hydrogen or fluoro; or

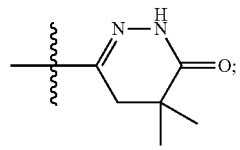

$R^2$ is hydrogen or fluoro;
or a pharmaceutically acceptable salt thereof.

Another aspect of the invention provides compounds of Formula I wherein:
$R^1$ is selected from the group:

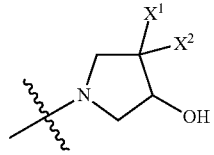

wherein each of $X^1$ and $X^2$ is independently selected from hydrogen, fluoro, or —CH$_3$;

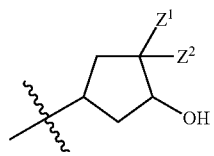

wherein each of $Z^1$ and $Z^2$ is independently selected from hydrogen or fluoro; or

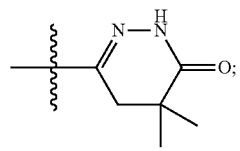 [SMILES: *C1=NNC(=O)C(C)(C)C1]

$R^2$ is fluoro;
or a pharmaceutically acceptable salt thereof.

Another aspect of the invention is a compound:
N-(6-Fluoro-1-oxo-1,2-dihydroisoquinolin-7-yl)-5-[(3R)-3-hydroxypyrrolidin-1-yl]thiophene-2-sulfonamide, or a pharmaceutically acceptable salt thereof;
N-(6-Fluoro-1-oxo-1,2-dihydroisoquinolin-7-yl)-5-[(3S)-3-hydroxypyrrolidin-1-yl]thiophene-2-sulfonamide, or a pharmaceutically acceptable salt thereof;
5-[(3S,4R)-3-Fluoro-4-hydroxy-pyrrolidin-1-yl]-N-(6-fluoro-1-oxo-1,2-dihydroisoquinolin-7-yl)thiophene-2-sulfonamide, or a pharmaceutically acceptable salt thereof;
5-(3,3-Difluoro-(4R)-4-hydroxy-pyrrolidin-1-yl)-N-(6-fluoro-1-oxo-1,2-dihydroisoquinolin-7-yl)thiophene-2-sulfonamide, or a pharmaceutically acceptable salt thereof;
5-(5,5-Dimethyl-6-oxo-1,4-dihydropyridazin-3-yl)-N-(6-fluoro-1-oxo-1,2-dihydroisoquinolin-7-yl)thiophene-2-sulfonamide, or a pharmaceutically acceptable salt thereof; or N-(6-Fluoro-1-oxo-1,2-dihydroisoquinolin-7-yl)-5-[(1R,3R)-3-hydroxycyclopentyl]thiophene-2-sulfonamide, or a pharmaceutically acceptable salt thereof.

Another aspect of the invention is a compound: N-(6-Fluoro-1-oxo-1,2-dihydroisoquinolin-7-yl)-5-[(3R)-3-hydroxypyrrolidin-1-yl]thiophene-2-sulfonamide, or a pharmaceutically acceptable salt thereof.

A further aspect of the invention is a pharmaceutical composition comprising a compound of Formula I, or a pharmaceutically acceptable salt thereof, with a pharmaceutically acceptable carrier.

Another aspect of the invention provides a method of treating a cancer which is glioblastoma, cervical cancer, uterine cancer, breast cancer, triple negative breast cancer, bladder cancer, head and neck cancer, kidney cancer, melanoma, pancreatic cancer, liver cancer, lung cancer (including mesothelioma), colorectal cancer, gastric cancer, osteosarcoma, non-Hodgkin lymphoma (including T-cell lymphoma), fibroblastic sarcoma, chronic myelogenous leukemia (CML), or acute lymphoid leukemia (ALL; including T-ALL, lymphoblast, and monocytic leukemia) in a patient comprising administering to a patient in need thereof a therapeutically effective amount of a compound of Formula I, or a pharmaceutically acceptable salt thereof.

Another aspect of the invention provides a method of treating a cancer which is triple negative breast cancer, bladder cancer, lung cancer (including mesothelioma), colorectal cancer, non-Hodgkin lymphoma (including T-cell lymphoma), chronic myelogenous leukemia (CML), or acute lymphoid leukemia (ALL; including T-ALL, lymphoblast, and monocytic leukemia) in a patient comprising administering to a patient in need thereof a therapeutically effective amount of a compound of Formula I, or a pharmaceutically acceptable salt thereof.

A still further aspect of the invention provides a compound of Formula I, or a pharmaceutically acceptable salt thereof, for use in therapy.

Another aspect of the invention provides a compound of Formula I, or a pharmaceutically acceptable salt thereof, for use in the treatment of a cancer which is glioblastoma, cervical cancer, uterine cancer, breast cancer, triple negative breast cancer, bladder cancer, head and neck cancer, kidney cancer, melanoma, pancreatic cancer, liver cancer, lung cancer (including mesothelioma), colorectal cancer, gastric cancer, osteosarcoma, non-Hodgkin lymphoma (including T-cell lymphoma), fibroblastic sarcoma, chronic myelogenous leukemia, or acute lymphoid leukemia (ALL; including T-ALL, lymphoblast, and monocytic leukemia).

Another aspect of the invention provides a compound of Formula I, or a pharmaceutically acceptable salt thereof, for use in the treatment of a cancer which is triple negative breast cancer, bladder cancer, lung cancer (including mesothelioma), colorectal cancer, non-Hodgkin lymphoma (including T-cell lymphoma, chronic myelogenous leukemia (CML), or acute lymphoid leukemia (ALL; including T-ALL, lymphoblast, and monocytic leukemia).

A further aspect of the invention provides use of a compound of Formula I, or a pharmaceutically acceptable salt thereof, for the manufacture of a medicament for treatment of a cancer which is glioblastoma, cervical cancer, uterine cancer, breast cancer, triple negative breast cancer, bladder cancer, head and neck cancer, kidney cancer, melanoma, pancreatic cancer, liver cancer, lung cancer (including mesothelioma), colorectal cancer, gastric cancer, osteosarcoma, non-Hodgkin lymphoma (including T-cell lymphoma), fibroblastic sarcoma, chronic myelogenous leukemia, or acute lymphoid leukemia (ALL; including T-ALL, lymphoblast, and monocytic leukemia).

A further aspect of the invention provides use of a compound of Formula I, or a pharmaceutically acceptable salt thereof, for the manufacture of a medicament for treatment of a cancer which is triple negative breast cancer, bladder cancer, lung cancer (including mesothelioma), colorectal cancer, non-Hodgkin lymphoma (including T-cell lymphoma), chronic myelogenous leukemia (CML), or acute lymphoid leukemia (ALL; including T-ALL, lymphoblast, and monocytic leukemia).

The term "patient" means mammal and "mammal" includes, but is not limited to, a human and companion animals including the domestic cat (*Felis catus*), domestic dog (*Canis lupus familiaris*), and domestic horse (*Equus ferus caballus*).

"Therapeutically effective amount" means the dosage of a compound of Formula I, or pharmaceutically acceptable salt thereof, or pharmaceutical composition containing a compound of Formula I, or pharmaceutically acceptable salt thereof necessary to inhibit AICARFT in a cancer patient and either destroy the target cancer cells or slow or arrest the progression of the cancer in a patient. Anticipated dosages of a compound of Formula I, or a pharmaceutically acceptable salt thereof, are in the range of 100 to 800 mg/patient/day. Preferred dosages are anticipated to be in the range of 150 to 600 mg/patient/day. Most preferred dosages are anticipated to be in the range of 225 to 500 mg/patient/day. The exact dosage required to treat a patient and the length of treatment time will be determined by a physician in view of the stage and severity of the disease as well as the specific needs and response of the individual patient. Although expressed as dosage on a per day basis, the dosing regimen may be adjusted to provide a more optimal therapeutic benefit to a patient and to manage or ameliorate any adverse reactions by a patient.

The terms "treatment," "treat," and "treating," are meant to include the full spectrum of intervention for the cancer from which the patient is suffering, such as administration of the active compound to alleviate, to slow, or reverse one or more of the symptoms and to delay progression of the cancer even if the cancer is not actually eliminated. The patient to be treated is a mammal, in particular a human being.

A compound of Formula I, or a pharmaceutically acceptable salt thereof, is preferably formulated as a pharmaceutical composition using a pharmaceutically acceptable carrier and administered by a variety of routes. Preferably, such compositions are for oral administration. Such pharmaceutical compositions and processes for preparing them are well known in the art. See, e.g., REMINGTON: THE SCIENCE AND PRACTICE OF PHARMACY (A. Gennaro, et al., eds., 19$^{th}$ ed., Mack Publishing Co., 1995). In a particular embodiment, the pharmaceutical composition comprises N-(6-fluoro-1-oxo-1,2-dihydroisoquinolin-7-yl)-5-[(3R)-3-hydroxypyrrolidin-1-yl]thiophene-2-sulfonamide, or a pharmaceutically acceptable salt thereof, and pharmaceutically acceptable carrier and optionally other therapeutic ingredients particularly for treatment of cancer generally or a specific cancer type.

A compound of the present invention, such as Example 1, is named: N-(6-fluoro-1-oxo-1,2-dihydroisoquinolin-7-yl)-5-[(3R)-3-hydroxypyrrolidin-1-yl]thiophene-2-sulfonamide (IUPAC); and may also be named: 2-thiophenesulfonamide, N-(6-fluoro-1,2-dihydro-1-oxo-7-isoquinolinyl)-5-[(3R)-3-hydroxy-1-pyrrolidinyl]-(CAS); and other names may be used to unambiguously identify a compound of the present invention.

A person of ordinary skill in the art will understand compounds of Formula I, particularly the $R^1$ groups and substituents on $R^1$ groups at the 3- and potentially 4-positions of a pyrrolidin-1-yl group; potentially at the 3-, 4- and 5-positions of a piperidin-1-yl group; 3- and potentially 4-positions of a cyclopentyl group; potentially 5-position of a 6-oxo-1,4,5,6-tetrahydropyridin-3-yl group; 4-position of a cyclopent-1-en-1-yl group; and 4-position of a cyclohex-1-en-1-yl group are chiral centers, or may give rise to chiral centers, affording a racemic mixture of two, or more stereoisomers. As used herein, a solid bond line, as distinguished from wedge or hatched line bond to a substituent, unless further specified to the extent known, includes the undetermined configuration individual stereoisomers and racemic mixture(s) including the named compound. Specific stereoisomers can be prepared by stereospecific synthesis using enantiomerically pure or enriched starting materials. The specific stereoisomers of either starting materials, intermediates, or final products can be resolved by techniques well known in the art, such as those found in *Stereochemistry of Organic Compounds*, E. I. Eliel and S. H. Wilen (Wiley 1994) and *Enantiomers, Racemates, and Resolutions*, J., Jacques, A. Collet, and S. H. Wilen (Wiley 1991), including chromatography on chiral stationary phases, enzymatic resolutions, or fractional crystallization or chromatography of diastereomers formed for that purpose, such as diastereomeric salts. Where a chiral compound is isolated or resolved into its isomers, but absolute configurations or optical rotations are not determined, the isomers are arbitrarily designated as isomer 1 and isomer 2 corresponding to the order each elutes from chiral chromatography and if chiral chromatography is initiated early in the synthesis, the same designation is applied to subsequent intermediates and examples.

One of ordinary skill in the art will recognize the compounds of Formula I can exist in tautomeric equilibrium. For illustrative purposes, the equilibrium is shown below:

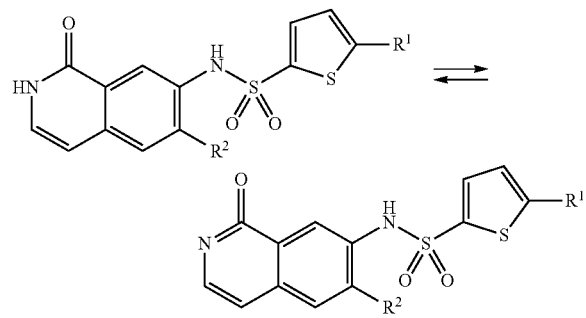

For convenience, the 4-oxo form is depicted in Formula I, and the corresponding nomenclature is used throughout this specification. However, such depictions include the corresponding tautomeric hydroxy form.

The compounds employed as initial starting materials in the synthesis of compounds of the present invention are well known and, to the extent not commercially available, are readily synthesized using specific references provided, by standard procedures commonly employed by those of ordinary skill in the art, or are found in general reference texts.

Examples of known procedures and methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5th Edition, Michael B. Smith and Jerry March, Wiley Interscience, 2001; Advanced Organic Chemistry, 4$^{th}$ Edition, Part B, Reactions and Synthesis, Francis A. Carey and Richard J. Sundberg, Kluwer Academic/Plenum Publishers, 2000, etc., and references cited therein.

Additionally, certain intermediates described in the following schemes may contain one or more protecting groups. The variable protecting group may be the same or different in each occurrence depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

The compound of Formula I, or pharmaceutically acceptable salts thereof, may be prepared by a variety of procedures known in the art, some of which are illustrated in the Preparations and Examples below. The specific synthetic steps for each of the routes described may be combined in different ways, or in conjunction with steps from different procedures, to prepare compounds of Formula I, or salts thereof. The product of each step can be recovered by conventional methods well known in the art, including extraction, evaporation, precipitation, chromatography, filtration, trituration, and crystallization. In addition, all substituents unless otherwise indicated, are as previously defined.

As used herein, "ACN" refers to acetonitrile; "AICAr" refers to 5-aminoimidazole-4-carboxamide 1-β-D-ribofuranosyl; "ATIC" refers to 5-amino-4-imidaloledcarboxamide ribonucleotide transformylase/Inosine 5'-monophosphate cyclohydralase; "BSA" refers to Bovine Serum Albumin; "Bu" refers to butyl; "DCM" refers to dichloromethane; "DIPEA" refers to diisopropylethylamine "DMAP" refers to 4-dimethylaminopyridine; "DMEM" refers to Dulbecco's Modified Eagle's Medium; "DMF-DMA" refers to 1,1-dimethoxy-N,N-dimethyl-methanamine; "DMSO" refers to dimethylsulfoxide; "DTT" refers to dithiothreitol; "EDTA" refers to ethylenediaminetetraacetic acid; "ee" refers to enantiomeric excess; "EtOAc" refers to ethyl acetate; "Ex" refers to example; "F12" refers to Ham's F12 medium; "FBS" refers to Fetal Bovine Serum; "HEPES" refers to 4-(2-hydroxyethyl)-1-piperazineethanesulfonic acid; "HOAc" refers to acetic acid; "HPBCD" refers to hydroxypropyl beta-cyclodextrin; "IC$_{50}$" refers to the concentration of an agent that produces 50% of the maximal inhibitory response possible for that agent; "IMP" refers to inosine 5'-monophosphate; "IPA" refers to isopropyl alcohol or isopropanol; "min" refers to minute or minutes; "IPTG" refers to isopropyl-beta-D-thiogalactopyranoside; "MeOH" refers to methanol or methyl alcohol; "MTBE" refers to methyl tert-butyl ether; "Ni-NTA" refers to nickel-nitrilotriacetic acid; "PBS" refers to Phosphate Buffered Saline; "Prep" refers to preparation; "psi" refers to pounds per square inch; "QD" refers to once a day dosing; "RPMI" refers to Roswell Park Memorial Institute; "R$_t$" refers to retention time; "SCX" refers to strong cation exchange chromatography; "SFC" refers to supercritical fluid chromatography; "SEM" refers to standard error of the mean; "TFA" refers to trifluoroacetic acid; "THF" refers to tetrahydrofuran.

The following preparations and examples further illustrate the invention.

Scheme 1

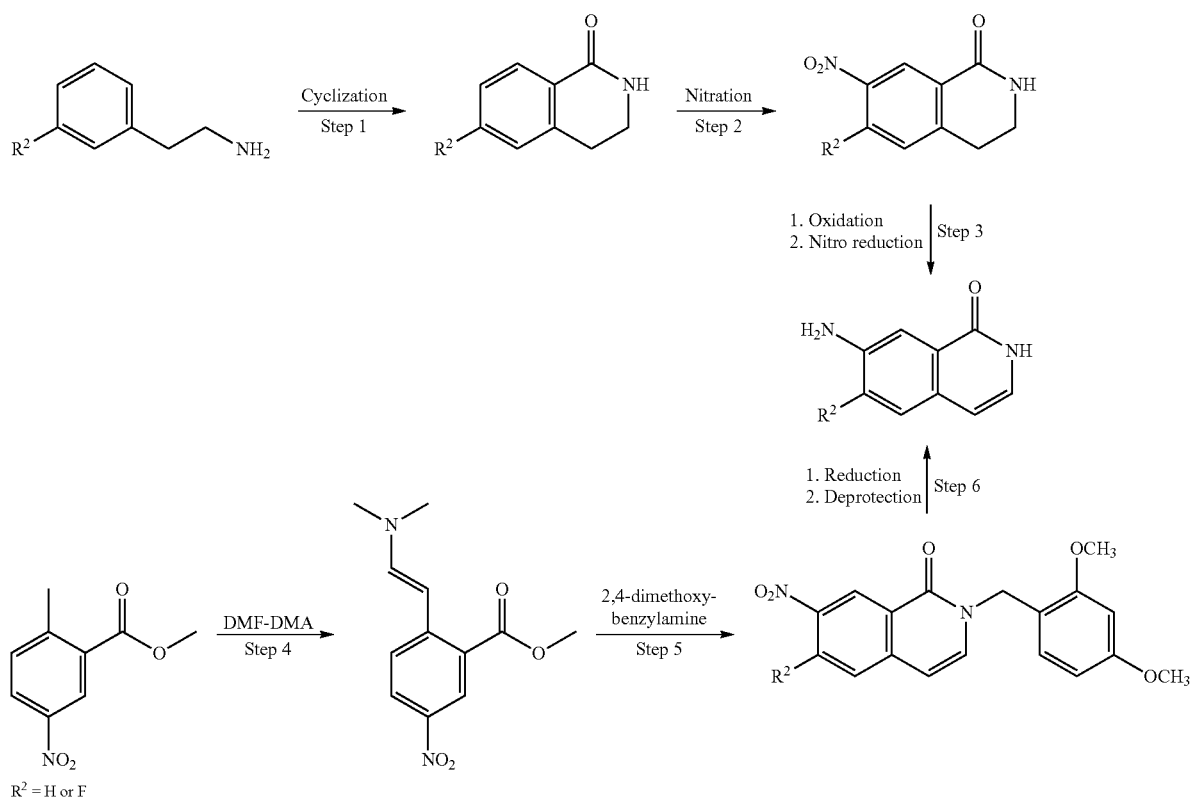

R² = H or F

R² is as defined above for Formula I. As illustrated in Scheme 1, the synthesis of the isoquinolin-1-one begins with Friedal-Crafts cyclization of a phenethylamine or 3-fluoro phenethylamine using triphosgene and dropwise addition of an organic base such as triethylamine with stirring followed by the addition of a Lewis acid such as aluminum trichloride to give the product of Step 1. In Step 2, nitration at the 7-position proceeds under conditions well known in the art, using an inorganic acid such as sulfuric acid and portion-wise addition of potassium nitrate. Step 3 involves oxidation using a large excess of manganese dioxide, about 18 equivalents, in dichloroethane with heating to about 120° C. to give the 6-substituted or unsubstituted-7-nitro-1,2-dihydroisoquinolin-1-one. The subsequent reduction of the nitro group may proceed under a variety of conditions known to one skilled in the art. For example, palladium-mediated hydrogenation in a polar aprotic solvent such as MeOH at about 50 psi pressure and about 60° C. gives the 6-substituted or unsubstituted-7-amino-1,2-dihydroisoquinolin-1-one, (Step 3).

In an alternate preparation (Scheme 1, Step 4), DMF-DMA is reacted with methyl 2-methyl-5-nitro-benzoate in a polar aprotic solvent such as acetone and heating to about 90-100° C. to give a methyl 2-[2-dimethylamino)vinyl]-5-nitro-benzoate as the product of Step 4. In Step 5, this intermediate is cyclized using 2,4-dimethoxybenzylamine in a non-polar solvent such as toluene with heating to about 90-100° C., yielding 7-amino-(6-substituted or unsubstituted-2-(2,4-dimethoxybenzyl)isoquinolin-1(2H)-one. The nitro group can be reduced as described above in Step 3 or alternatively, by adding zinc powder in a solution of about 1:1 MeOH and water with ammonium chloride and heating to about 40-80° C. providing 7-amino-2-(2,4-dimethoxy-benzyl)-(6-fluoro or unsubstituted)-isoquinolin-1-one. Removal of the 2,4-dimethoxybenzyl protecting group can be completed as shown in Step 6 or at a later step in the synthesis using conditions well known in the art such as with TFA or HBr in water with heating to about 80-95° C.

Scheme 2

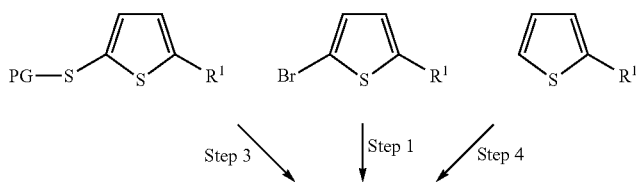

-continued

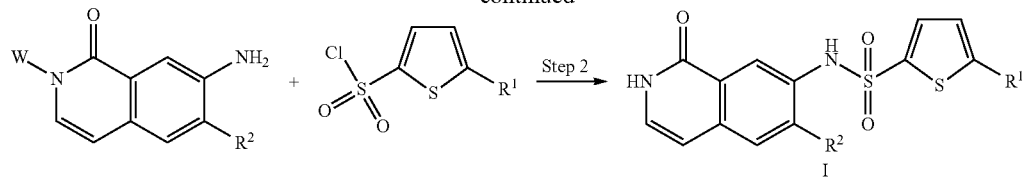

$R^1$ = Hal or as defined above for Formula I; Hal is Br or F
$R^2$ = H or F
W = H or PG; PG is a Protecting Group Scheme 2 illustrates the preparation of and coupling of 5-substituted thiophene-2-sulfonyl chloride with protected or unprotected isoquinolin-1(2H)-one to give the sulfonamide compounds of Formula I when $R^1$ is as defined for Formula I. As necessary to generate the requisite intermediate sulfonyl chloride, 2-substituted 5-bromothiophene can be treated with butyl lithium in a polar aprotic solvent such as THF at −78° C. and then treated with sulfur dioxide and sulfuryl chloride (Step 1). This intermediate can be added to the 7-amino-2H-isoquinolin-1-one in a solvent such as DCM and an organic base such as pyridine to give compounds of Formula I from Step 2. If protected isoquinolin-1(2H)-one is used, the protecting group can be removed with an acid such as TFA. Other alternatives involve preparing the product of Step 1 from a 2-substituted thiophene with chlorosulfuric acid or chlorsulfuric acid and phosphorus pentachloride, (Step 4), and from a protected 5-sulfanyl-2-substituted thiophene with 1,3-dichloro-5,5-dimethylhydantoin (Step 3).

Scheme 3

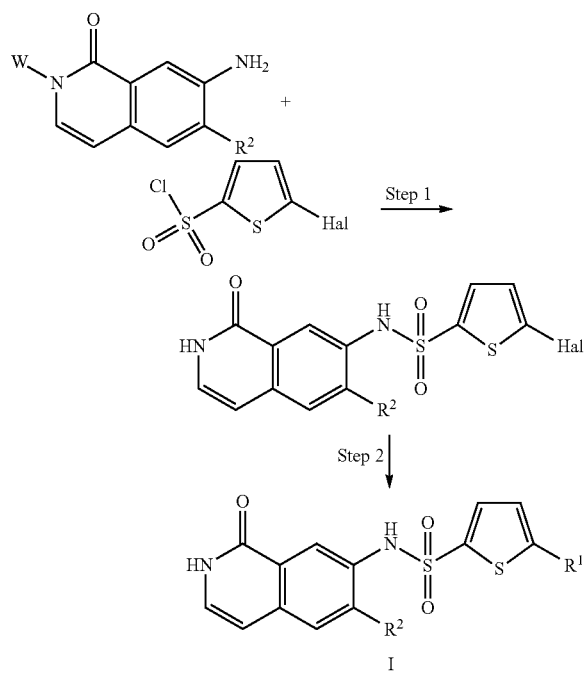

Hal = Br or F
$R^2$ = H or F
W = H or PG

In an alternative preparation as shown in Scheme 3, coupling of 5-halo-substituted thiophene-2-sulfonyl chloride with protected or unprotected isoquinolin-1 (2H)-one provides useful sulfonamide intermediates. This is effected through reaction of the amine with 5-halo-thiophene-2-sulfonyl chloride in the presence of an organic base such as pyridine, with or without a solvent such as DCM at 0° C. to room temperature to give the sulfonamide intermediate product of Step 1. The intermediate product of Step 1 is also illustrated as having the optional protecting group removed, such as with TFA. The intermediate product from Step 1 can be further alkylated under Suzuki-Miyaura cross coupling conditions with an appropriate boronic acid. The skilled artisan will recognize that there are a variety of conditions useful for facilitating such cross-coupling reactions. Accordingly, a suitable palladium reagent includes bis(triphenylphosphine)palladium(II) chloride, tris(dibenzylideneacetone)dipalladium (0) with tricyclohexylphosphine, (1,1'-bis (diphenylphosphino)ferrocene)palladium(II) chloride, palladium tetrakistriphenylphosphine, or palladium(II) acetate. A suitable base includes cesium carbonate, sodium carbonate, potassium carbonate, or potassium phosphate tribasic monohydrate. The reactions can be heated to a temperature of about 100-150° C. in a non-polar solvent such as dioxane.

Alternatively, copper-mediated amination of the 5-bromothiophene products of Step 1, can be accomplished using copper(I)bromide, an organic base, hydroxyproline, an appropriate amine, and an inorganic base such as cesium carbonate or potassium carbonate in a polar aprotic solvent such as DMSO and heating to about 100° C., to yield compounds of Formula I in Step 2. A further coupling example can be accomplished via a SnAr reaction on intermediates from Step 1 where Hal is fluorine, using an organic base such as pyridine and/or DIPEA, an appropriate amine and heating to about 100° C. to give compounds of Formula I. In either case, when W is PG, the protecting group is removed with an acid such as TFA.

In an optional step, a pharmaceutically acceptable salt of a compound of Formula I can be formed by reaction of a compound of Formula I with an appropriate pharmaceutically acceptable base in a suitable solvent under standard conditions. The formation of such salts is well known and appreciated in the art. See, for example, P. Stahl, et al., HANDBOOK OF PHARMACEUTICAL SALTS: PROPERTIES, SELECTION AND USE, (VCHA/Wiley-VCH, 2002); Gould, P. L., "Salt selection for basic drugs," *International Journal of Pharmaceutics,* 33: 201-217 (1986); Bastin, R. J., et al. "Salt Selection and Optimization Procedures for Pharmaceutical New Chemical Entities," *Organic Process Research and Development,* 4: 427-435 (2000); and Berge, S. M., et al., "Pharmaceutical Salts," *Journal of Pharmaceutical Sciences,* 66: 1-19, (1977). One of ordinary skill in the art will appreciate that a compound of Formula I is readily converted to and may be isolated as a pharmaceutically acceptable salt, such as sodium, potassium, calcium, or magnesium salt.

PREPARATIONS AND EXAMPLES

The following preparations and examples further illustrate the invention.

Preparation 1

Methyl 2-[(E)-2-(dimethylamino)vinyl]-5-nitro-benzoate

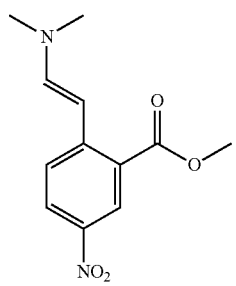

Add methyl 2-methyl-5-nitro-benzoate (1.79 Kg, 9.17 mol) to acetone (16 L). Add DMF-DMA (1.83 Kg, 15.4 mol). Stir the resulting mixture at 95-100° C. for 16 hours. Cool to 20-25° C. and pour the mixture into water (48 L) with stirring to form a slurry. Filter the solid and wash the cake with water. Slurry the solid with water (2×16 L) and filter the solid. Dry the solid in the air for two days to give the crude title compound as a red solid (2.42 Kg, 105%). $^1$H-NMR (400 MHz, CDCl$_3$): δ 8.72 (1H, d, J=2.4 Hz), 8.06 (1H, dd, J=9.2, 2.8 Hz), 7.46 (1H, d, J=8.8 Hz), 7.21 (1H, d, J=13.6 Hz), 6.42 (1H, d, J=13.2 Hz), 3.92 (3H, s), 3.02 (6H, s).

Preparation 2

2-(2,4-Dimethoxybenzyl)-7-nitroisoquinolin-1(2H)-one

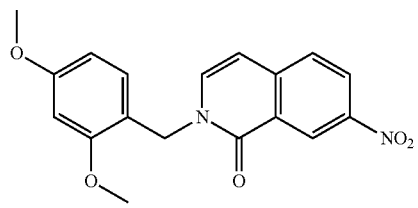

Add methyl 2-[(E)-2-(dimethylamino)vinyl]-5-nitro-benzoate (2.4 Kg crude, 9.65 mol), 2,4-dimethoxybenzylamine (2.14 Kg, 12.8 mol) and toluene (30 L). Heat the mixture to 95-100° C. and stir at that temperature for 16 hours. Cool to 20-25° C. and collect the precipitated solid by filtration. Dry the yellow solid in the air for two days to give the crude product (2.17 Kg, 66%) which is used without further purification. ES/MS (m/z): 341.1 (M+H).

Preparation 3

7-Amino-2-(2,4-dimethoxybenzyl)isoquinolin-1(2H)-one

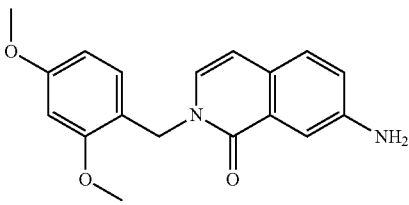 [SMILES: COc1ccc(Cn2ccc3ccc([N+](=O)[O-])cc3c2=O)c(OC)c1]

Add MeOH (10 L), water (10 L), and ammonium chloride (1.56 Kg, 29.2 mol). Add 2-(2,4-dimethoxybenzyl)-7-nitroisoquinolin-1(2H)-one (2 Kg, 5.84 mol). Heat the resulting mixture to 40° C. Then, add zinc powder (1.53 Kg, 23.37 mol) to the mixture at 40° C. Remove the heat. The internal temperature increases to 70° C. slowly. Heat the reaction to 80° C. and stir at that temperature for 16 hours. Cool the reaction mixture to 15-20° C. Filter the mixture and wash the cake with EtOAc (1 L×2). Add water (15 L) to the filtrate and extract with EtOAc (5 L×3). Dry the combined organic extracts over Na$_2$SO$_4$, filter, and concentrate to dryness. Treat the resultant residue with MTBE/MeOH to give the title compound (942 g, 53%). ES/MS (m/z): 311.1 (M+H).

Preparation 4

7-Aminoisoquinolin-1(2H)-one

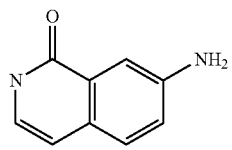 [SMILES: Nc1ccc2cc[nH]c(=O)c2c1]

Add together 7-amino-2-(2,4-dimethoxybenzyl)isoquinolin-1(2H)-one (849 g, 2.74 mol) and TFA (5 L) to form a brown mixture. Heat the mixture to 80-85° C. and stir at that temperature for 2 hours. The solid dissolves gradually and the mixture turns dark purple. Cool the reaction mixture to 20-25° C. Remove most of the TFA under reduced pressure. Add MeOH (5 L) and stir at 40-50° C. for 30 minutes. Filter the mixture and concentrate the filtrate to dryness. Dissolve the residue in EtOAc (5 L) and water (5 L). Extract the aqueous phase with EtOAc (5 L). Heat the aqueous phase to 55-60° C. and add active charcoal (90 g). Stir the mixture at that temperature for 1 hour. Filter the mixture through diatomaceous earth and rinse with water. Cool the filtrate to 35° C. naturally and neutralize with solid Na$_2$CO$_3$ (153 g) at 35-40° C. to pH=7-8. Cool the mixture to 5-10° C. and stir for 16 hours. Collect the precipitated solid by filtration, wash with cold water and MTBE, and dry in open air to give the title compound (260 g, 59%). ES/MS (m/z): 161.1 (M+H).

Alternate Preparation 4

Add 7-amino-2-(2,4-dimethoxybenzyl)isoquinolin-1 (2H)-one (2.1 Kg, 3.72 mol) to HBr solution (21 L, 40% in H$_2$O). Heat the resulting mixture to 95° C. and stir for 18 hours at that temperature. Cool the reaction to 20-25° C. Filter the reaction to remove insoluble material. Extract the filtrate with CHCl₃/IPA (10/1, 2×11 L). Separate the organic phase. Filter the aqueous suspension solid precipitate. Add the cake into CHCl₃/IPA (10/1, 11 L) and HBr solution (1 L, 40% in H₂O). Stir the mixture at 80° C. for 2 hours. Filter the mixture to give a crude solid. Add the crude solid to water (1 L) and adjust the pH to 7-8 with 10 M NaOH solution. Filter the solid and dry in oven at 40° C. for 24 hours to give the title compound as a brown solid (475 g, 44%). ES/MS (m/z): 161.1 (M+H).

Preparation 5

6-Fluoro-3,4-dihydroisoquinolin-1(2H)-one

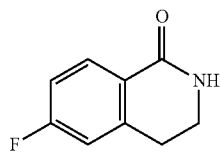 [SMILES: O=C1NCCc2cc(F)ccc21]

Add a solution of 2-(3-fluorophenyl)ethanamine (1 Kg, 7.18 mol) in DCM (2 L) to a solution of triphosgene (852.4 g, 2.87 mol) in DCM (5 L) in an ice-bath. Then, add drop wise triethylamine (2 L, 14.36 mol). Stir the resulting solution for 2 hours and filter through diatomaceous earth and wash with DCM. Add the filtrate into a suspension of AlCl₃ (3.82 Kg, 28.72 mol) in DCM (6 L) at 0° C. Allow the resulting solution to warm to room temperature and stir for 18 hours. Quench the reaction by addition of water and then 10% HCl. Collect the organic layer by phase separation and extract the aqueous layer with DCM. Wash the combined DCM layers with saturated sodium bicarbonate solution and brine solution, dry over Na₂SO₄, concentrate in vacuo, and purify on silica gel eluting with petroleum ether/EtOAc=2:1 to give the title compound (474.73 g, 40%). ¹H NMR (400 MHz CDCl₃) δ 8.05-8.09 (m, 1H), 7.02-7.04 (m, 1), 6.90-6.92 (m, 1H), 6.77 (br, s, 1H), 3.55-3.59 (m, 2H), 2.97-3.00 (t, 2H).

Preparation 6

6-Fluoro-7-nitro-3,4-dihydroisoquinolin-1(2H)-one

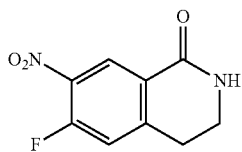 [SMILES: O=C1NCCc2cc(F)c([N+](=O)[O-])cc21]

Cool a solution of 6-fluoro-3,4-dihydroisoquinolin-1 (2H)-one (1 Kg, 6.06 mol) in H₂SO₄ (10 L) to 0° C. and add KNO₃ (643 g, 6.36 mol) portion wise. Stir the resulting mixture in ice-bath for 2 hours. Pour the mixture into ice-water and filter the solid. Wash the solid with water and dry in vacuo at 50° C. overnight to give the title compound (1.18 Kg, 93%). ¹H NMR (400 MHz DMSO) δ 8.43-8.45 (d, 1H), 8.26 (br, s, 1H), 7.59-7.62 (d, 1H), 3.39-3.43 (m, 2H), 3.01-3.04 (m, 2H).

Preparation 7

6-Fluoro-7-nitroisoquinolin-1(2H)-one

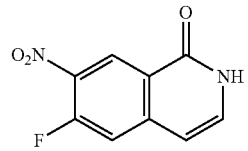

Add MnO₂ (4.136 Kg, 47.60 mol) to a solution of 6-fluoro-7-nitro-3,4-dihydroisoquinolin-1(2H)-one (1 Kg, 4.76 mol) in dichloroethane (10 L) and heat the mixture to 120° C. for 5 hours. Add MnO₂ (2.068 Kg, 23.8 mol) and stir the mixture overnight. Add further MnO₂ (1.241 Kg, 14.28 mol) and stir the reaction overnight. Cool the mixture to about 80° C., filter over diatomaceous earth, and rinse with DMSO (5×). Concentrate the filtrate to remove the dichloroethane and pour the DMSO solution into water. Filter the precipitated yellow solid, wash with water, and dry to obtain the title compound (446 g, 45%). ¹H NMR (400 MHz MeOD) δ 8.98-9.00 (d, 1H), 7.62-7.65 (d, 1H), 7.38-7.40 (d, 1H), 6.68-6.70 (d, 1H).

Preparation 8

7-Amino-6-fluoroisoquinolin-1(2H)-one

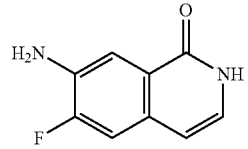 [SMILES: Nc1cc2c(=O)[nH]ccc2cc1F]

Add to a vessel a mixture of carefully wetted 10% palladium on carbon (20 g, 0.18 mol) in MeOH (1.5 L) and 6-fluoro-7-nitroisoquinolin-1(2H)-one (100 g, 0.48 mol). Seal the vessel and purge three times with H₂. Stir the resulting mixture under 50 psi of H₂ for 2.5 hours at 60° C. Filter the mixture, rinse with MeOH repeatedly, and concentrate to dryness. Suspend the residue in MTBE, filter, rinse with MTBE, and dry to give the title compound (81.2 g, 95%) as a brown solid. ¹H NMR (400 MHz, DMSO): δ 10.88 (br, s, 1H), 7.49-7.51 (d, 1H), 7.25-7.29 (d, 1H), 6.85-6.88 (m, 1H), 6.32-6.34 (d, 1H), 5.52 (br, s, 2H).

Preparation 9

5-Bromo-N-[2-(2,4-dimethoxybenzyl)-1-oxo-1,2-dihydroisoquinolin-7-yl]thiophene-2-sulfonamide

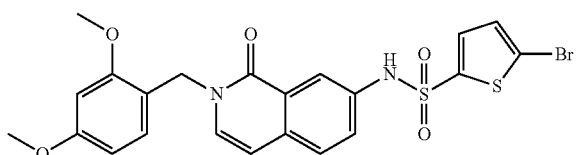

Add pyridine (78.2 mL, 966 mmol) and 5-bromothiophene-2-sulfonyl chloride (69.53 g, 266 mmol) to a solution of 7-amino-2-(2,4-dimethoxybenzyl)isoquinolin-1(2H)-on (75 g, 241.6 mmol) in DCM (750 mL) at 0° C. Stir the resulting solution at room temperature for 2 hours. Add water (500 mL) to precipitate a dark solid. Filter the mixture and wash the solid with water (3×300 mL) and MTBE, dry under vacuum to give the title compound (91 g, 70%). ES/MS (m/z) ($^{79}$Br/$^{81}$Br) 535/537 [M+H]$^+$.

Preparation 10

5-Bromo-N-(1-oxo-1,2-dihydroisoquinolin-7-yl)thiophene-2-sulfonamide

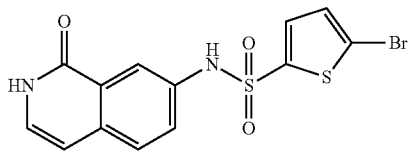 [SMILES: O=c1[nH]ccc2ccc(NS(=O)(=O)c3ccc(Br)s3)cc12]

Heat to 80° C. a solution of 5-bromo-N-[2-(2,4-dimethoxybenzyl)-1-oxo-1,2-dihydroisoquinolin-7-yl]thiophene-2-sulfonamide (50 g, 93.38 mmol) in TFA (100 mL) for 3 hours. Allow to warm to room temperature. Dissolve the residue in THF (60 mL) and add ammonia (60 mL) carefully. Stir the resulting mixture at room temperature overnight. Filter the solid in suspension, wash with EtOAc, dry, and collect. Wash the filtrate with saturated aqueous NaHCO$_3$ and separate the two phases. Extract the aqueous phase with a 9:1 mixture CHCl$_3$/IPA (4×250 mL) and combine the organic extracts, dry and evaporate to dryness. Triturate the residue in a 9:1 MTBE/IPA mixture until a light brown solid precipitates. Filter the solid, wash with MTBE, dry and collect the solid. Concentrate the filtrate and purify in a silica gel column (1:1 ACN/CH$_2$Cl$_2$) to get additional product. Triturate the three solids in a 1:1 mixture of ACN/CH$_2$Cl$_2$. Filter the combined solids, wash with IPA, dry, and collect the solid to give the title compound (24.5 g, 68%). ES/MS (m/z) ($^{79}$Br/$^{81}$Br) 385/387 [M+H]$^+$.

Alternate Preparation 10

Add 7-aminoisoquinolin-1(2H)-one (15.1 g, 94.27 mmol), 5-bromothiophene-2-sulfonyl chloride (26.2 g, 97.10 mmol) and pyridine (45.7 mL, 565.63 mmol) to DCM (500 mL). Stir the resulting mixture at room temperature under nitrogen for 30 minutes. Dilute the mixture with water and acidify with 5 N HCl to pH of about 4. Stir for 10 minutes. Filter the resulting precipitate, rinse with water, ether and dry the solid. Suspend the precipitate in MeOH and add NH$_3$/EtOH to dissolve it. Stir the solution with activated charcoal, filter over diatomaceous earth, and evaporate the filtrate. Suspend the obtained solid in acetone, filter, and dry the solid to give the title compound (24 g, 66%) as a pale yellow solid. ES/MS (m/z) ($^{79}$Br/$^{81}$Br) 385/387 [M+H]$^+$.

Preparation 11

5-Bromo-N-(6-fluoro-1-oxo-1,2-dihydroisoquinolin-7-yl)thiophene-2-sulfonamide

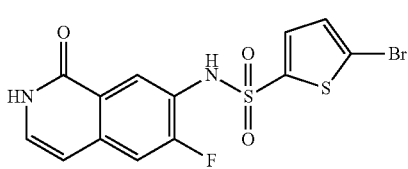 [SMILES: O=c1[nH]ccc2cc(F)c(NS(=O)(=O)c3ccc(Br)s3)cc12]

Add 5-bromothiophenesulfonyl chloride (54.48 g, 202.06 mmol) in portions to a solution of 7-amino-6-fluoroisoquinolin-1(2H)-one (30 g, 168 mmol) in pyridine (210 mL). Stir the resulting mixture at room temperature under nitrogen for 2 hours. Dilute the mixture with DCM (120 mL) and water (210 mL). Acidify the mixture with concentrated HCl until pH of about 6. Filter the precipitated solid, wash with water (2×), 1 N HCl, water (3×), and MTBE, dry and collect the solid to give the title compound (53.6 g, 79%). ES/MS (m/z) ($^{79}$Br/$^{81}$Br) 403/405 [M+H]$^+$.

Prepare the following compounds essentially by the method of Preparation 11 using the appropriate sulfonyl chloride cooling the reaction to 0° C. and working up by washing with NaOH (1 N) and extracting with EtOAc followed by acidification and work-up as in Preparation 11.

TABLE 1

| Prep No. | Chemical Name | Structure | ES/MS (m/z) (M + 1) |
|---|---|---|---|
| 12 | 5-Fluoro-N-(6-fluoro-1-oxo-1,2-dihydroisoquinolin-7-yl)thiophene-2-sulfonamide | 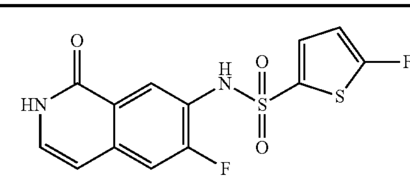 | 343 |

Preparation 13

5-Acetyl-N-(1-oxo-1,2-dihydroisoquinolin-7-yl)thiophene-2-sulfonamide

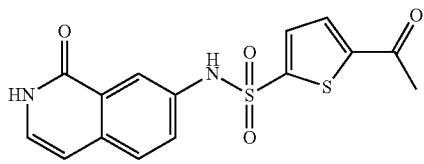 [SMILES: CC(=O)c1ccc(S(=O)(=O)Nc2ccc3cc[nH]c(=O)c3c2)s1]

Dissolve 5-bromo-N-(1-oxo-1,2-dihydroisoquinolin-7-yl)thiophene-2-sulfonamide (0.5 g, 1.3 mmol) in THF (20 mL) and cool the resulting mixture under nitrogen in a dry ice/acetone bath. Slowly add butyl lithium (1.6 M in hexanes, 2.9 mL, 4.64 mmol) and stir with cooling for approximately 40 minutes whereupon a suspension forms. Then add N-methoxy-N-methyl-acetamide (0.17 g, 1.64 mmol) in THF (2 mL, 24.6 mmol) and allow mixture to warm to 0° C. Quench the reaction mixture with ice/water, adjust the pH to approximately 5, and extract the mixture with EtOAc. Combine the organic extracts and concentrate under reduced pressure to give a residue. Purify the residue by silica gel flash chromatography, eluting with 0-10% MeOH—NH₃/DCM to give the title compound of 50% purity (0.52 g, 115%) which is used without further purification. ES/MS (m/z): 347 (M−H).

Preparation 14 racemic trans Benzyl-3-hydroxy-4-methoxy-pyrrolidine-1-carboxylate

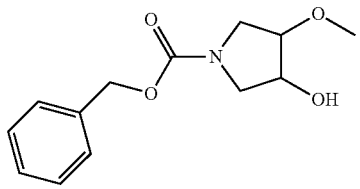 [SMILES: COC1CN(C(=O)OCc2ccccc2)CC1O]

Combine racemic trans-4-methoxypyrrolidin-3-ol; hydrochloride (1.02 g, 6.64 mmol) with sodium carbonate (1.5 g, 14.15 mmol) and a mixture of THF (20 mL, 245.8 mmol) and water (20 mL, 1.11 mmol) and cool the mixture in an ice bath. Add benzyl chloroformate (1.3 mL, 8.81 mmol) and stir the mixture under nitrogen while warming to room temperature. Upon completion, dilute the reaction with water and extract the aqueous mixture with EtOAc. Dry the combined extracts over Na₂SO₄ and concentrate under reduced pressure to give a residue. Purify the residue by silica gel flash chromatography, eluting with 0-5% MeOH/DCM to give the title compound (1.68 g, 100%) as a thick oil. ES/MS (m/z): 252 (M+H).

Preparation 15 racemic cis Benzyl-3-hydroxy-4-methoxy-pyrrolidine-1-carboxylate

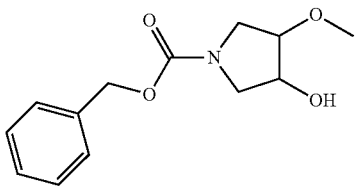 [SMILES: COC1CN(C(=O)OCc2ccccc2)CC1O]

Dissolve racemic cis benzyl-3-methoxy-4-(4-nitrobenzoyl)oxy-pyrrolidine-1-carboxylate (1.80 g, 4.5 mmol) in MeOH (10 mL, 245.8 mmol), add ammonia/MeOH (2 M, 50 mL, 100 mmol) and stir the mixture at room temperature for 6 hours. Concentrate the mixture under reduced pressure to give a residue. Purify the residue by silica gel flash chromatography, eluting with 0-10% THF/DCM to give the title compound (0.945 g, 84%) as a thick oil. ES/MS (m/z): 252 (M+H).

Preparation 16 cis-4-Methoxypyrrolidin-3-ol

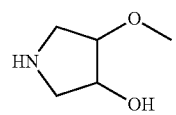

Combine racemic cis benzyl-3-hydroxy-4-methoxy-pyrrolidine-1-carboxylate (0.93 g, 3.7 mmol) with a mixture of palladium black (0.023 g, 0.22 mmol) and 5% palladium on carbon (0.105 g, 0.099 mmol) in THF (20 mL) and MeOH (20 mL) and stir under hydrogen (345 kPa) at room temperature for 4 hours. Filter the reaction mixture through diatomaceous earth and wash with ethanol. Concentrate the filtrate under reduced pressure to give the title compound (0.493 g, 113%) as a thick oil. ES/MS (m/z): 118 (M+H

Preparation 17 cis [4-[(1-tert-Butoxycarbonyl-4-fluoro-pyrrolidin-3-yl]oxycarbonylphenyl]azinate

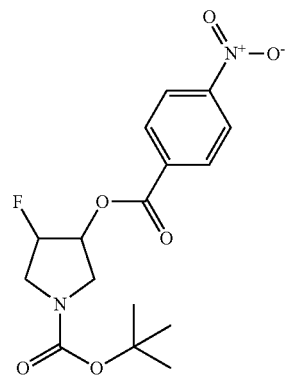 [SMILES: CC(C)(C)OC(=O)N1CC(F)C(OC(=O)c2ccc([N+](=O)[O-])cc2)C1]

Add diisopropyl azodicarboxylate (9.66 mL, 48.7 mmol) to a chilled ice bath (0° C.) solution of tert-butyl (3R,4R)-3-fluoro-4-hydroxy-pyrrolidine-1-carboxylate (5.0 g, 24.4 mmol), 4-nitrobenzoic acid (8.14 g, 48.7 mmol) and triphenylphosphine (12.8 g, 48.7 mmol) in THF (100 mL) and stir for 2 hours. Allow the reaction to warm to room temperature and stir for 18 hours. Add saturated sodium bicarbonate solution to quench the reaction, extract with EtOAc, and dry over magnesium sulfate. Filter and concentrate under reduced pressure to yield an oil. Purify the oil via normal phase silica gel chromatography, eluting with 25% EtOAc-hexanes to give a white solid with impurity carryover (10.7 grams, 124%). LC/MS m/e 299 [M+1]⁺-t-butyl. Although initiated with chiral reactant, chiral purity was not maintained through this or subsequent Preparations or Examples using the compound of Preparation 17.

Prepare the following compound essentially by the method of Preparation 17 using racemic trans benzyl-3-hydroxyl-4-methoxy-pyroolidine-1-carboxylate.

Preparation 20

Cis, meso-tert-Butyl 3,4-dihydroxypyrrolidine-1-carboxylate

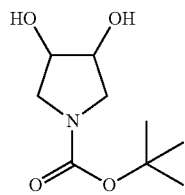

Add N-methylmorpholine-N-oxide (1.98 grams, 14.2 mmol) to a solution of tert-butyl 2,5-dihydropyrrole-1-carboxylate (2.0 grams, 11.8 mmol), osmium tetraoxide (0.04 M, 5.93 mL, 0.47 mmol) in acetone (50 mL), and

TABLE 2

| Prep. No. | Chemical Name | Structure | ES/MS (m/z) (M + 1) |
|---|---|---|---|
| 18 | racemic cis Benzyl-3-methoxy-4-(4-nitrobenzoyl)oxy-pyrrolidine-1-carboxylate | 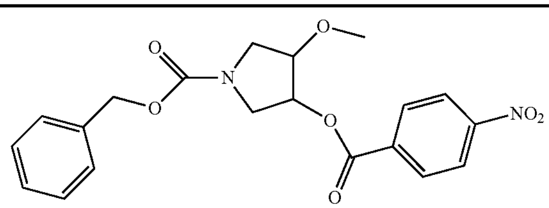 | 401 |

Preparation 19 cis tert-Butyl 3-fluoro-4-hydroxy-pyrrolidine-1-carboxylate

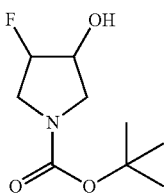

Add sodium hydroxide (2 N, 60 mL) to a chilled ice bath (0° C.) solution of [4-[(3S,4R)-1-tert-butoxycarbonyl-4-fluoro-pyrrolidin-3-yl]oxycarbonylphenyl]azinate (10.7 gr, 30.2 mmol) in THF (50 mL). Stir for 2 hours at 0° C. Concentrate under reduced pressure to an oil. Purify the oil via normal phase silica gel chromatography, eluting with 50% MTBE-hexanes (detection 2 214 nm) to give a clear oil (2.72 g, 43.9%). ¹H NMR (399.81 MHz, d₆-DMSO) δ 5.37 (d, J=6.1 Hz, 1H), 4.95-4.81 (m, 1H), 4.20-4.18 (m, 1H), 3.48-3.41 (m, 3H), 2.99-2.91 (m, 1H), 1.35 (d, J=1.2 Hz, 9H). Although initiated with chiral reactant, chiral purity was not maintained through this or subsequent Preparations or Examples using the compound of Preparation 19.

water (10 mL). Stir for 18 hours at room temperature. Concentrate the reaction under reduced pressure and extract the aqueous phase with EtOAc. Concentrate the organic extracts under reduced pressure. Purify the oil via normal phase chromatography, eluting with hexanes to 80% (5% MeOH-THF)-20% hexanes to give the title compound (0.51 grams, 21.2%). LC/MS m/e 202 [M−H]⁻

Preparation 21

3-(5-Bromo-2-thienyl)cyclopentanone

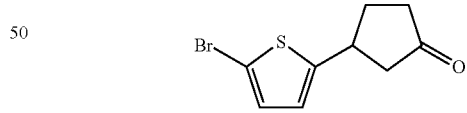

Add 2.5 M butyl lithium (12.2 mL, 17.7 mmol) to a chilled (−78° C.) solution of 2,5-dibromothiophene (2 mL, 97.3 mmol) in THF and maintain the temperature at −70° C. Allow the reaction to warm to −60° C. and then cool back to −78° C. Add zinc bromide (4.98 g, 22.12 mmol) as a solid. Warm the reaction to −10° C. then cool to −78° C. Add 2-cyclopenten-1-one (1.85 mL, 22.12 mmol), drop wise and stir for 5 minutes at −78° C.; then add chlorotrimethylsilane (2.93 mL, 23.0 mmol), drop wise. Allow the reaction to warm to room temperature and stir for 18 hours. Add 1 N HCl (100 mL) to quench the reaction, extract with EtOAc, and dry over magnesium sulfate. Filter and concentrate under reduced pressure to give a red oil. Purify the oil via normal phase chromatography, eluting with 30% THF-hexanes to give a clear oil (2.90 grams, 11.82 mmol, 66.8%). $^1$H NMR (399.81 MHz, d$_6$-DMSO) δ 7.04 (d, J=3.7 Hz, 1H), 6.78 (dd, J=1.0, 3.7 Hz, 1H), 3.62-3.59 (m, 1H), 2.60-2.55 (m, 1H), 2.35-2.32 (m, 4H), 1.93-1.85 (m, 1H).

Prepare the following compound essentially by the method of Preparation 21 using (2-oxocyclopent-3-en-1-yl) acetate instead of 2-clyclopeten-1-one (Preparation 25).

| Prep. No. | Chemical Name | Structure | GC ES/MS (m/z) (M + 1) |
|---|---|---|---|
| 22 | (2-Oxocyclo-pent-3-en-1-yl) acetate | 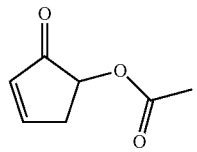 | ($^{79}$Br/$^{81}$Br) 302/304 |

Preparation 23

3-(5-Bromo-2-thienyl)cyclopentanol

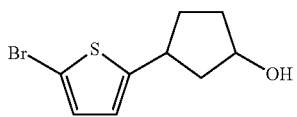 [SMILES: OC1CCC(c2ccc(Br)s2)C1]

Add sodium borohydride (0.254 g, 6.73 mmol) to a suspension of 3-(5-bromo-2-thienyl)cyclopentanone (0.55 g, 2.24 mmol) in dioxane (20 mL). Add MeOH (2 mL), drop wise, and stir for 1 hour. Add MeOH (about 20 mL), drop wise, to quench reaction. Concentrate reaction under reduced pressure. Purify via normal phase silica gel chromatography, eluting with 35% THF-hexanes to give a clear oil (0.325 grams, 58.6%). $^1$H NMR (399.81 MHz, d$_6$-DMSO) δ 6.98-6.96 (m, 1H), 6.68 (td, J=3.6, 0.8 Hz, 1H), 4.62 (d, J=4.1 Hz, 0.7H), 4.55-4.54 (m, 0.3H), 4.23-4.19 (m, 0.3H), 4.17-4.10 (m, 0.7H), 3.47-3.43 (m, 0.3H), 3.21-3.13 (m, 0.7H), 2.32-2.27 (m, 0.7H), 2.15-2.12 (m, 0.3H), 1.99-1.93 (m, 1.3H), 1.75-1.69 (m, 3.9H).

Preparation 24

2-(3-Benzyloxycyclopentyl)-5-bromo-thiophene

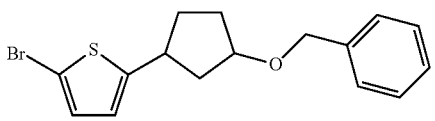

Add benzyl bromide (1.22 mL, 10.2 mmol) and sodium iodide (0.25 g, 1.70 mmol) to a solution of 3-(5-bromo-2-thienyl)cyclopentanol (2.1 g, 8.5 mmol) in THF (100 mL). Cool the reaction to 0° C. After 5 minutes, add sodium hydride (60%, 0.41 grams, 10.2 mmol) to the reaction and warm to room temperature. Add DMF to assist in solubility. Heat to 50° C. for 1 hour, add saturated ammonia chloride to quench reaction and extract with EtOAc and dry over magnesium sulfate. Filter and concentrate under reduced pressure to give an oil. Purify the oil via normal phase silica gel chromatography, eluting with 25% THF-hexanes to give a clear yellow oil (1.3 g, 45.4%). $^1$H NMR (399.81 MHz, d$_6$-DMSO) δ 7.33-7.28 (m, 5H), 6.99-6.97 (m, 1H), 6.72-6.69 (m, 1H), 4.41 (d, J=2.6 Hz, 2H), 4.09-4.05 (m, 1H), 3.45-3.37 (m, 0.3H), 3.25-3.18 (m, 0.7H), 2.42-2.37 (m, 0.7H), 2.20-1.78 (m, 5.3H).

Preparation 25

(2-Oxocyclopent-3-en-1-yl) acetate

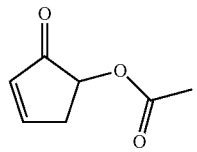

Add lead tetraacetate (11.7 g, 26.4 mmol) to a solution of 2-cyclopenten-1-one (2 mL, 23.9 mmol) in benzene (100 mL), in a sealed vessel. Heat to 80° C. for 72 hours. Cool to room temperature, filter over a pad of silica gel, and wash with DCM. Concentrate under reduced pressure to give a brown oil. Purify the oil via silica gel chromatography, eluting with hexanes to 25% THF-hexanes to give a clear oil (1.42 g, 42.3%). $^1$H NMR (399.80 MHz, CDCl$_3$) δ 7.65 (ddd, J=6.1, 3.0, 2.5 Hz, 1H), 6.25 (dt, J=6.1, 2.1 Hz, 1H), 5.11 (dd, J=3.1, 6.9 Hz, 1H), 3.19-3.16 (m, 1H), 2.63-2.57 (m, 1H), 2.13 (d, J=0.5 Hz, 3H).

Preparation 26

[4-(5-Bromo-2-thienyl)-2,2-difluoro-cyclopentyl] acetate

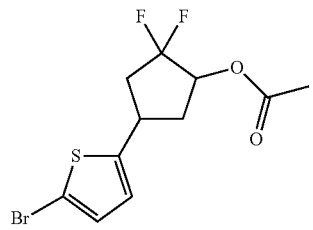 [SMILES: CC(=O)OC1CC(c2ccc(Br)s2)CC1(F)F]

Add bis(2-methoxyethyl)aminosulfur trifluoride (2.6 mL, 11.7 mmol) to a solution of [4-(5-bromo-2-thienyl)-2-oxo-cyclopentyl] acetate (1.18 g, 3.89 mmol) in DCM (50 mL). Stir at room temperature for 18 hours. Add saturated sodium bicarbonate solution to quench the reaction, stir for 15 minutes while reaction evolves gas then extract with DCM and dry over magnesium sulfate. Filter and concentrate under reduced pressure to yield a brown oil. Purify the oil via silica gel chromatography, eluting with 20% THF-hexanes to give a clear oil (0.77 g, 60.8%). GC/MS m/e ($^{79}$Br/$^{81}$Br) 324/326 [M+H]$^+$

Preparation 27

2-(4-Benzyloxy-3,3-difluoro-cyclopentyl)-5-bromo-thiophene

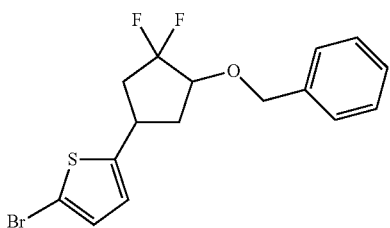 [SMILES: FC1(F)CC(c2ccc(Br)s2)CC1OCc1ccccc1]

Add potassium carbonate (0.85 g, 6.15 mmol) to a solution of [4-(5-bromo-2-thienyl)-2-oxo-cyclohexyl] acetate (1.0 g, 3.06 mmol) in MeOH (100 mL) and stir at room temperature for about 12 hours. Remove the solvent and dry the residue under vacuum. Add benzyl bromide (0.4 mL, 3.4 mmol) to a solution of the residue in THF (100 mL) and stir the reaction at room temperature for 18 hours. Dilute reaction with EtOAc, add saturated ammonium chloride solution to quench the reaction, back extract aqueous phase with DCM and dry combined organic extracts over magnesium sulfate. Filter and concentrate under reduced pressure to yield a brown oil. Purify the oil via silica gel chromatography, eluting with 20% THF-hexanes to give a clear oil (1.0 g, 87.1%). GC/MS m/e ($^{79}$Br/$^{81}$Br) 372/374 [M+H]$^+$.

Preparation 28

5-(4-Benzyloxy-3,3-difluoro-cyclopentyl)-N-(6-fluoro-1-oxo-1,2-dihydroisoquinolin-7-yl)thiophene-2-sulfonamide

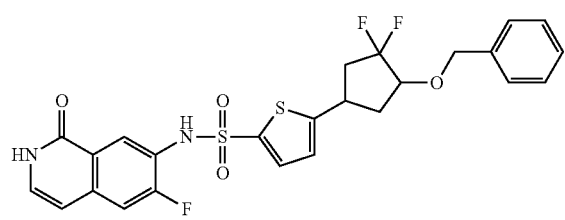 [SMILES: O=c1[nH]ccc2cc(F)c(NS(=O)(=O)c3ccc(C4CC(OCc5ccccc5)C(F)(F)C4)s3)cc12]

Add 2.5 M butyl lithium (2.5 mL, 6.2 mmol) via syringe pump to a chilled (−78° C.) solution of 2-(4-benzyloxy-3,3-difluoro-cyclopentyl)5-bromothiophene (2.1 g, 5.63 mmol) in THF (75 mL) and maintain temperature of at least −70° C. Stir at −78° C. for 1 hour and add to a freshly prepared saturated solution of sulfur dioxide in THF (50 mL) at −78° C. (prepared by bubbling in gas via sparge tube at −78° C.) via canula and maintain temperature of at least −70° C. Stir reaction for 1 hour at −78° C. then add sulfuryl chloride (1.4 mL, 16.9 mmol), drop wise. Allow the reaction to warm to room temperature and stir for 18 hours. Quench the reaction with 2 N HCl (100 mL), add solid sodium chloride to saturate solution and extract with MTBE. Dry the organic extracts over magnesium sulfate. Filter and concentrate under reduced pressure to give a thick brown oil which is dissolved in DCM (50 mL). Via dropping funnel, add brown solution to a 0° C. cooled solution of 7-amino-6-fluoroisoquinolin-1-(2H)-one (1.0 g, 5.63 mmol) in DCM (20 mL) and pyridine (50 mL). Stir the reaction for 36 hours at room temperature. Concentrate under reduced pressure to yield an oil. Purify the oil via silica gel chromatography, eluting with 90% (10% MeOH-EtOAc)-10% hexanes to give an orange solid (1.49 g, 49.5%). MS (m/z): 535 (M+H)

Preparation 29 racemic-4,4-Difluoropiperidin-3-ol

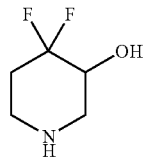

For the preparation of racemic-4,4-difluoropiperidin-3-ol, see Synlett 2009, No. 12, 1933-1936 and references therein.

Preparation 30 racemic, trans-4-Fluoropiperidin-3-ol hydrochloride

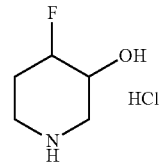

Add HCl (57.0 mL, 228 mmol; 4 M in dioxane) to a solution of racemic, trans-tert-butyl-4-fluoro-3-hydroxy-piperidine-1-carboxylate (5 g, 22.8 mmol) in MeOH (50 mL). Stir for 16 hours at ambient temperature and concentrate under reduced pressure to give the title compound (3.7 g, 100%): $^1$H NMR (400 MHz, d$_6$-DMSO) δ 9.54-9.52 (m, 2H), 6.15-6.14 (m, 1H), 4.66-4.52 (m, 1H), 3.92-3.86 (m, 1H), 3.15 (d, J=12.0 Hz, 2H), 2.97-2.82 (m, 2H), 2.22-2.15 (m, 1H), 1.94-1.85 (m, 1H).

Preparation 31 racemic, cis-tert-Butyl 4-fluoro-3-(4-nitrobenzoyl)oxy-piperidine-1-carboxylate

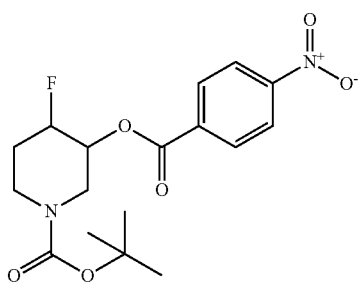 [SMILES: CC(C)(C)OC(=O)N1CCC(F)C(OC(=O)c2ccc([N+](=O)[O-])cc2)C1]

Add diisopropyl azodicarboxylate (8.66 mL, 42.8 mmol) drop wise to a mixture of racemic, trans-4-fluoro-3-hydroxy-piperidine-1-carboxylate (4.84 g, 21.4 mmol), 4-nitrobenzoic acid (7.3 g, 42.8 mmol), and triphenylphosphine (11.3 g, 42.8 mmol) in THF (150 mL) at 0° C. Stir the mixture while gradually warming to ambient temperature for 16 hours. Quench with saturated aqueous sodium bicarbonate and extract with EtOAc.

Combine the organic extracts and wash with water, brine, dry over magnesium sulfate, filter, and concentrate under reduced pressure to give a residue. Purify the residue by silica gel flash chromatography, eluting with 15-25% acetone/hexanes to give the title compound (4.4 g, 56%). ES/MS (m/z): 391 (M+23).

Preparation 32 racemic, cis-tert-Butyl 4-fluoro-3-hydroxypiperidine-1-carboxylate

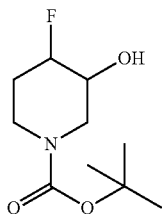

Add 2 N aqueous lithium hydroxide (24 mL, 48 mmol) to a solution of racemic, cis-tert-butyl 4-fluoro-3-(4-nitrobenzoyl)oxy-piperidine-1-carboxylate (4.4 g, 12 mmol) in THF (100 mL). Stir for 1 hour, dilute with water, and extract with EtOAc. Combine the organic extracts and wash with water, dry over magnesium sulfate, filter, and concentrate under reduced pressure to give the title compound (2.78 g, 100%). ES/MS (m/z): 241 (M+23).

Preparation 33 racemic, cis-4-Fluoropiperidin-3-ol hydrochloride

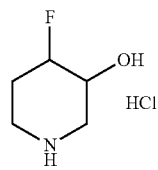

Add HCl (31.7 mL, 127 mmol; 4 N in dioxane) to a solution of racemic, cis-tert-butyl 4-fluoro-3-hydroxypiperidine-1-carboxylate (2.78 g, 12.7 mmol) in MeOH (100 mL) and stir for 16 hours. Concentrate under reduced pressure to give a residue. Triturate the residue from diethyl ether: MeOH (10:1), filter the precipitate, rinse with diethyl ether and dry to give the title compound (1.6 g, 81%). $^1$H NMR (400 MHz, d$_6$-DMSO) δ 9.65-8.99 (m, 2H), 6.17-6.15 (m, 1H), 4.88-4.74 (m, 1H), 4.04-3.97 (m, 1H), 3.08-2.96 (m, 4H), 2.15-2.02 (m, 2H).

Preparation 34 tert-Butyl 3-hydroxy-4,4-dimethoxy-piperidine-1-carboxylate

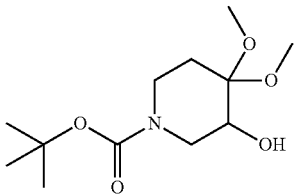 [SMILES: COC1(OC)CCN(C(=O)OC(C)(C)C)CC1O]

Prepare tert-butyl 3-hydroxy-4,4-dimethoxy-piperidine-1-carboxylate according to WO2009033581. Dissolve potassium hydroxide (7.040 g, 125.47 mmol) in MeOH (150 mL) and cool to 0° C. Treat with N-tert-butoxycarbonyl-4-piperidone (10 g, 50.19 mmol) and stir 15 minutes before adding a solution of iodine (15.286 g, 60.23 mmol) in MeOH (200 mL) drop wise. Stir at 0° C. for 1 hour then remove the cooling bath and stir for 1 hour. Concentrate under vacuum. Mix with toluene and filter. Concentrate to dryness to give the title compound (13.1 g (99%) as an oil that is used without further purification.

Preparation 35 tert-Butyl 3-benzyloxy-4,4-dimethoxy-piperidine-1-carboxylate

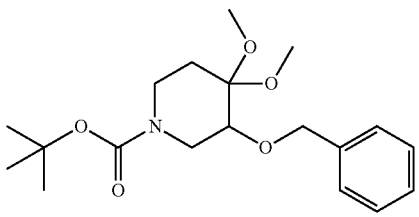 [SMILES: COC1(OC)CCN(C(=O)OC(C)(C)C)CC1OCc1ccccc1]

Mix sodium hydride (612.222 mg, 15.31 mmol) with THF (25 mL) and cool to 0° C. Add a solution of tert-butyl 3-hydroxy-4,4-dimethoxy-piperidine-1-carboxylate (2 g, 7.65 mmol) in THF (10 mL). Stir at 0° C. for 10 minutes before adding benzylbromide (2.618 g, 15.31 mmol). Stir at ambient temp for 2 hours. Add benzyltrimethylammonium iodide (0.2 g, 0.72 mmol) and continue stirring 16 hours. Pour into a mixture of EtOAc (200 mL) and brine (100 mL). Separate the layers, dry the organic layer over MgSO$_4$, and concentrated to 3.5 g oil. Chromatograph on silica gel chromatography eluting with hexanes and EtOAc 70/30 to give the title compound as an oil (2.52 g, 93%). $^1$H NMR (CDCl$_3$) δ 1.43 (s, 9H), 1.67-1.79 (m, 1H), 1.8-1.97 (m, 1H), 2.71-2.89 (m, 1H), 2.9-3.09 (m, 1H), 3.3 (s, 3H), 3.13 (s, 3H), 3.38-3.49 (m, 1H), 4.01-4.3 (m, 2H), 4.37-45 (m 1H), 4.85-4.73 (m, 1H), 7.2-7.4 (m, 5H)

Preparation 36

Benzyl 3-benzyloxy-4-oxo-piperidine-1-carboxylate

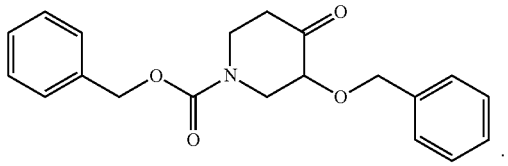 [SMILES: O=C1CCN(C(=O)OCc2ccccc2)CC1OCc1ccccc1]

Mix tert-butyl 3-benzyloxy-4,4-dimethoxy-piperidine-1-carboxylate (14.56 g, 41.43 mmol) with TFA (25 mL) and H$_2$O (0.1 mL). Stir at ambient temperature 50 hours. Concentrate to an oil. Mix with H$_2$O (25 mL) and stir at ambient temp for 1 hour. Concentrate under vacuum with minimal heating to a viscous amber oil. Dilute with DCM (150 mL) and cool to 0° C. Add benzyl chloroformate (10.601 g, 62.14 mmol) followed by DIPEA (16.064 g, 124.29 mmol) drop wise. Stir 16 hours, wash 1 N HCl (3×100 mL), and dry over MgSO$_4$. Concentrate to dryness and purify by silica gel flash chromatography eluting with hexanes and ethylacetate 70/30 to give the title compound as an oil (13.86 g, 98%). ES/MS (m/z): 357 (M+H).

Preparation 37 racemic Benzyl 3-benzyloxy-4-hydroxy-4-(trifluoromethyl)piperidine-1-carboxylate Diastereomer 1

Preparation 38 racemic Benzyl 3-benzyloxy-4-hydroxy-4-(trifluoromethyl)piperidine-1-carboxylate Diastereomer 2

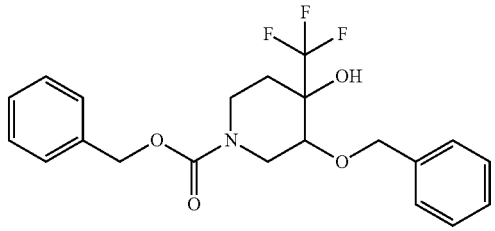 [SMILES: O=C(OCc1ccccc1)N1CCC(O)(C(F)(F)F)C(OCc2ccccc2)C1]

Mix benzyl 3-benzyloxy-4-oxo-piperidine-1-carboxylate (2.6 g, 7.66 mmol) with THF (30 mL) and cool to 10° C. under N$_2$. Add (trifluoromethyl)trimethylsilane (1.634 g, 11.49 mmol) followed by 1 M tetrabutylammonium fluoride (13.835 g, 15.32 mmol) in THF drop wise. Stir at 10° C. for 30 minutes then remove the cooling bath and stir at ambient temp. After 1 hour add 1 M tetrabutylammonium fluoride (4 mL) in THF and stir for 10 minutes. Quench the reaction with brine (50 mL) and separate the layers. Extract the aqueous with EtOAc (50 mL) and combine with the original THF layer. Dry over MgSO$_4$ and concentrate to dryness. Purify the residue by silica gel flash chromatography, eluting with hexanes EtOAc 70/30 to recover the title compounds as oils. Diastereomer 1 (1 g, 31%), ES/MS (m/z): 410 (M+H). Diastereomer 2 (1 g, 31%), ES/MS (m/z): 410 (M+H).

Preparation 39 racemic 4-(Trifluoromethyl)piperidine-3,4-dio, Diastereomer 1

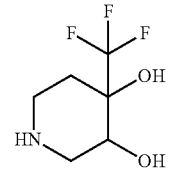

Mix benzyl 3-benzyloxy-4-hydroxy-4-(trifluoromethyl)piperidine-1-carboxylate, Diastereomer 1 (1.5 g, 3.66 mmol), palladium on carbon 10% (1 g), MeOH (25 mL) and acetic acid (10 mL). Stir at ambient temperature while bubbling H$_2$ into the mixture for 16 hours. Filter and concentrate under vacuum. Mix with toluene and re-concentrate to an oil to recover 0.85 g of an oily film. Dissolve in MeOH, elute onto a 10 g SCX cartridge, and wash with 1 column volume of MeOH. Elute product with 2 M NH$_3$ in MeOH. Concentrate to give the title compound as a solid (0.6 g, 88%). $^1$H NMR (d$_6$-DMSO) δ 1.36-1.48 (m, 1H), 1.57-1.65 (m, 1H), 1.8-1.97 (m, 1H), 2.2 (bs, 1H), 2.4-2.5 (m, 1H), 2.52-2.7 (m, 2H), 3.5-3.6 (m, 1H), 4.8 (bs, 1H), 5.3 (bs, 1H)

Prepare the following compounds essentially by the method of Preparation 39.

TABLE 3

| Prep. No. | Chemical Name | Structure | NMR |
|---|---|---|---|
| 40 | racemic, 4-(Trifluoromethyl)-piperidine-3,4-diol, Diastereomer 2 | 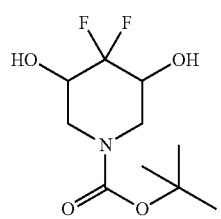 [SMILES: CC(C)(C)OC(=O)N1CC(O)C(F)(F)C(O)C1] | (d$_6$-DMSO) δ 1.3-139 (m, 1H), 1.75-1.89 (m, 1H), 2.53-2.71 (m, 3H), 2.85-2.93 (m, 1H), 3.37 (s, 1H), 3.15 (s, 1H), 4.8 (bs, 1H), 5.8 (bs, 1H) |

Preparation 41 cis, meso-tert-Butyl 4,4-difluoro-3,5-dihydroxy-piperidine-1-carboxylate, Isomer 1

Preparation 42 racemic, trans-tert-Butyl 4,4-difluoro-3,5-dihydroxy-piperidine-1-carboxylate, Isomer 2

Add cesium carbonate (3.13 g, 9.61 mmol) to an ice-cooled solution of cyclohexane-1,3-dione (1.00 g, 4.69 mmol) in ACN (30 mL) at 0° C. and stir. After 15 minutes, add 1-chloromethyl-4-fluoro-1,4-diazoniabicyclo[2.2.2]octane bis(tetrafluoroborate) (Selectfluor™, 3.99 g, 11.26 mmol). After 30 minutes, remove the cooling bath and allow the reaction mixture to warm up to ambient temperature. After 2 hours, filter and concentrate under reduced pressure. Dissolve the residue in EtOAc, extract with 1 N aqueous hydrochloric acid, wash with brine, dry over sodium sulfate, filter, and concentrate under reduced pressure. Dissolve the residue in a mixture of THF (50 mL) and ethanol (25 mL). Cool to 0° C. in an ice bath. Add sodium borohydride (887 mg, 23.5 mmol). After 30 min, remove the cooling bath and allow the reaction mixture to warm up to ambient temperature. After 1.5 hour, quench the reaction with saturated aqueous ammonium chloride solution. Remove most of the solvents under reduced pressure. Dissolve the residue with EtOAc, extract with water and brine, dry over sodium sulfate, filter, and concentrate under reduced pressure. Purify the residue by silica gel flash chromatography, eluting with 0-100% EtOAc/hexanes to give a 3:1 mixture of isomer 1 and isomer 2 (0.43 g, 36%) (27% yield of isomer 1 and 9% yield of isomer 2). $^{19}$F NMR (376 MHz, d$_4$-CD$_3$OD) δ−121.8 (d, 1F, J=240 Hz, isomer 1), −126.5 (dd, 2F, J=570, 240 Hz, Isomer 2), −142.0 (d, 1F, J=240 Hz, Isomer 1). Use without further purification.

Preparation 43 racemic, trans tert-Butyl 3-fluoro-4-hydroxypiperidine-1-carboxylate

Preparation 44 racemic, cis-tert-Butyl 3-fluoro-4-hydroxypiperidine-1-carboxylate

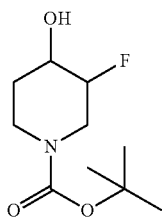

Add sodium borohydride (1.20 g, 31.7 mmol) to an ice cooled solution of tert-butyl 3-fluoro-4-oxopiperidine-1-carboxylate (4.5 g, 19.68 mmol) in MeOH (50 mL) at 0° C. After 15 minutes, remove the cooling bath and allow the reaction mixture to warm up to ambient temperature. After 45 minutes, quench the reaction with saturated aqueous ammonium chloride solution. Remove most of the solvents under reduced pressure. Dissolve the residue with EtOAc, extract with brine, dry over sodium sulfate, filter, and concentrate under reduced pressure. Purify the residue by silica gel flash chromatography, eluting with 20-100% EtOAc/hexanes to give racemic, trans-tert-butyl 3-fluoro-4-hydroxypiperidine-1-carboxylate (0.75 g, 17%): $^1$H NMR (400 MHz, CDCl$_3$) δ 4.34 (ddd, 0.5H), 4.20 (ddd, 0.5H), 4.06 (br s, 1H), 3.86-3.76 (m, 2H), 3.12 (br s, 1H), 3.06 (br s, 1H), 2.98 (ddd, 1H), 2.00-1.92 (m, 1H), 1.56-1.46 (m, 1H), 1.44 (s, 9H); and racemic, cis-tert-butyl 3-fluoro-4-hydroxypiperidine-1-carboxylate (2.55 g, 59%): $^1$H NMR (400 MHz, CDCl$_3$) δ 4.66-4.57 (m, 0.5H), 4.55-4.45 (m, 0.5H), 4.00-3.78 (m, 2H), 3.70 (br s, 1H), 3.32 (br s, 1H), 3.10 (br s, 1H), 2.85 (s, 1H), 1.84-1.74 (m, 1H), 1.71 (br s, 1H), 1.44 (s, 9H).

Preparation 45

Ethyl 4-((tert-butoxycarbonyl)amino)-2,2-difluoro-3-hydroxybutanoate

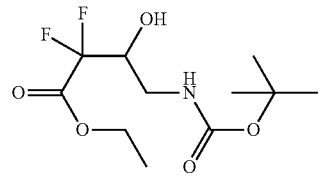 [SMILES: CCOC(=O)C(F)(F)C(O)CNC(=O)OC(C)(C)C]

Add indium (8.66 g, 75.4 mmol) to a solution of ethyl 2-bromo-2,2-difluoroacetate (9.67 mL, 75.4 mmol) and tert-butyl (2-oxoethyl)carbamate (10.0 g, 62.8 mmol) in THF (300 mL). Heat the mixture at 55° C. for 16 hours and cool to ambient temperature. Quench the reaction with saturated aqueous ammonium chloride solution. Remove most of the solvents under reduced pressure. Dissolve the residue in EtOAc, extract with 1 N aqueous HCl solution, water, and brine, dry over sodium sulfate, filter, and concentrate under reduced pressure. Use the crude material (17.8 g, 62.8 mmol) without further purification: $^1$H NMR (400 MHz, CDCl$_3$) δ 5.05 (br s, 1H), 4.37 (q, 2H), 4.25-4.08 (m, 2H), 3.60-3.50 (m, 1H), 3.48-3.33 (m, 1H), 1.46 (s, 9H), 1.37 (t, 3H).

Preparation 46 tert-Butyl 4-((tert-butoxycarbonyl)oxy)-3,3-difluoro-2-oxopyrrolidine-1-carboxylate

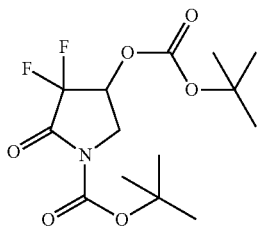 [SMILES: CC(C)(C)OC(=O)OC1CN(C(=O)OC(C)(C)C)C(=O)C1(F)F]

Add 4.0 M HCl solution in dioxane (100 mL) to crude ethyl 4-((tert-butoxycarbonyl)amino)-2,2-difluoro-3-hydroxybutanoate (17.8 g, 62.8 mmol). After 2 hours, remove all the solvents under reduced pressure. Dissolve the residue in ACN (75 mL). Add triethylamine (75 mL). After 17 hours, add DMAP (0.65 g, 5.3 mmol) and di-tert-butyl dicarbonate (30.2 mL, 138 mmol). After 2 hours, remove the solvents under reduced pressure. Add water and brine to the residue. Extract with 1:1 hexanes/EtOAc. Combine the organic extracts, wash with brine, dry over sodium sulfate, filter, and concentrate under reduced pressure. Purify the residue by silica gel flash chromatography, eluting with 0 to 50% EtOAc/hexanes to give the title compound (6.50 g, 31%): $^1$H NMR (400 MHz, CDCl₃) δ 5.28-5.21 (m, 1H), 4.05 (dd, 1H), 3.88-3.80 (m, 1H), 1.57 (s, 9H), 1.53 (s, 9H).

Preparation 47

4,4-Difluoropyrrolidin-3-ol

Add 4.0 M HCl solution in dioxane (200 mL) to tert-butyl 4-((tert-butoxycarbonyl)oxy)-3,3-difluoro-2-oxopyrrolidine-1-carboxylate (6.00 g, 17.8 mmol). After 8 hours, remove the solvents under reduced pressure. Dissolve the residue in THF (150 mL) and cool the reaction mixture to 0° C. in an ice bath. Add 60 wt. % solution of bis(2-methoxyethoxy)aluminum hydride in toluene (Red-Al™, 17.4 mL, 88.9 mmol). After 30 min, remove the cooling bath and allow the reaction mixture to warm up to ambient temperature. After 3 hours, cool the reaction mixture to 0° C. in an ice bath. Quench the reaction with sodium sulfate decahydrate. Remove the cooling bath and allow the reaction mixture to warm up to ambient temperature with vigorous stirring. After 30 minutes, filter off the solids, wash with THF, and concentrate under reduced pressure. Purify the residue by silica gel flash chromatography, eluting with 0 to 10% 7 M ammonia solution in MeOH/DCM to give the title compound (1.80 g, 82%). ¹H NMR (400 MHz, CD₃OD) δ 4.12-3.98 (m, 1H), 3.36-3.23 (m, 1H), 3.22-3.02 (m, 2H), 2.90-2.75 (m, 1H).

Preparation 48

2,2-Dimethyl-4-oxo-4-(2-thienyl)butanoic acid

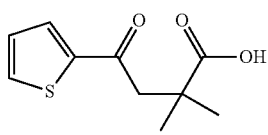

Add aluminum trichloride (3.12 g, 23.4 mmol) to an ice cooled solution of thiophene (7.77 mL, 97.56 mmol) and 3,3-dimethyltetrahydrofuran-2,5-dione (2.50 g, 19.5 mmol) in DCM (60 mL) at 0° C. Allow the reaction mixture to warm up to ambient temperature slowly. After 16 hours, cool the reaction mixture to 0° C. in an ice bath. Quench with 2N aqueous HCl solution. Extract with DCM. Combine all the organic layers, wash with water and brine, dry over sodium sulfate, filter and concentrate under reduced pressure to give the title compound (4.15 g, 19.5 mmol) which is used without further purification. ES/MS (m/z): 214 (M+H).

Preparation 49

5,5-Dimethyl-3-(2-thienyl)-1,4-dihydropyridazin-6-one

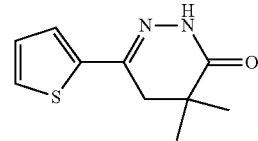

Add hydrazine (15 mL, 468 mmol) to solution of crude 2,2-dimethyl-4-oxo-4-(2-thienyl)butanoic acid (4.15 g, 19.5 mmol) in IPA (60 mL). Heat the mixture at 110° C. for 17 hours and cool to ambient temperature. Remove solvents under reduced pressure to give a residue. Purify the residue by silica gel flash chromatography, eluting with 0 to 100% EtOAc/hexanes to give the title compound (0.65 g, 16%): ¹H NMR (400 MHz, d₆-DMSO) δ 10.8 (s, 1H), 7.61 (dd, 1H), 7.46 (dd, 1H), 7.11 (dd, 1H), 2.86 (s, 2H), 1.09 (s, 6H).

Preparation 49a

2-Benzylsulfanyl-5-bromo-thiophene

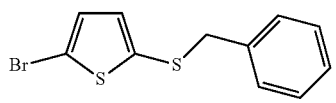 [SMILES: Brc1ccc(SCc2ccccc2)s1]

Add N-bromosuccinimide (232.6 g, 1.30 mol) in one portion to a solution of 2-benzylsulfanylthiophene (321 g, 1.48 mol) in DCM (1.9 L) at 0° C. Remove the cooling bath and stir at room temperature for 30 minutes. Filter the mixture and rinse the solid with MTBE (2×50 mL). Concentrate filtrate in vacuo. Slurry the residue in MTBE (1 L) for 30 minutes. Filter the solid and rinse with MTBE (2×100 mL). Wash the filtrate with ice/water (200 mL) and brine (200 mL). Dry the organic phase (MgSO₄), filter, and concentrate in vacuo to give the title compound (390 g, 99%). ¹H-NMR (CDCl₃) δ 7.3-7-2 (3H, m), 7.2-7.1 (2H, m), 6.86 (1H, d, J=3.9 Hz), 6.67 (1H, d, J=3.9 Hz), 3.92 (2H, s).

Preparation 49b

6-[5-(Benzylsulfanyl)thiophene-2-yl]-4,4-dimethyl-4,5-dihydropyridazin-3 (2H)-one

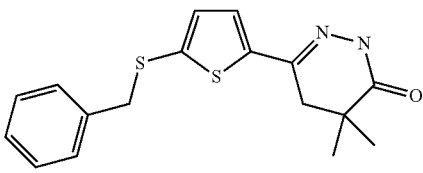 [SMILES: CC1(C)CC(c2ccc(SCc3ccccc3)s2)=NNC1=O]

Add isopropylmagnesium chloride (44 mL, 88.3 mmol, 2.0 M in THF) drop wise to a solution of 2-benzylsulfanyl-5-bromo-thiophene (22.9 g, 80.3 mmol) in THF (230 mL) at room temperature and stir for 30 minutes. Add the solution via cannula to a solution of 2,2-dimethylsuccinic anhydride (11.5 g, 88.3 mmol) in THF (115 mL) at −78° C. Stir at −78° C. for 15 minutes and allow the mixture to gradually warm to room temperature. Remove the cooling bath and stir at room temperature for 30 minutes. Add MTBE (200 mL) and wash with 1 N HCl (100 mL). Separate the two phases and extract the aqueous with MTBE (2×50 mL). Dry the combined organic extracts (MgSO₄), filter, and concentrate in vacuo to a brown solid. Suspend the solid in a 4:1 hexane/MTBE mixture, triturate, and filter the solid. Wash the grey solid with hexane, dry and collect to get the intermediate 4-(5-benzylsulfanyl-2-thienyl)-2,2-dimethyl-4-oxo-butanoic acid (18.7 g, 70%). ES/MS (m/z): 335 (M+H).

Dissolve 4-(5-benzylsulfanyl-2-thienyl)-2,2-dimethyl-4-oxo-butanoic acid (18.7 g, 55.9 mmol) in 2-propanol (187 mL) and add hydrazine monohydrate (4.15 mL, 83.9 mmol). Stir the mixture at 80° C. overnight. Allow the mixture to warm to room temperature and evaporate the solvent to dryness. Suspend the yellow residue in MTBE. Filter the bright yellow solid, wash with MTBE and dry to give the title compound (16 g, 87%). ES/MS (m/z): 331 (M+H).

Preparation 50

N-Allyl-2,2-dimethyl-pent-4-enamide

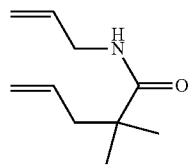

Add DIPEA (4.08 mL, 23.4 mmol) to a solution of 2,2-dimethylpent-4-enoic acid (2.00 g, 15.6 mmol), prop-2-en-1-amine (1.76 mL, 23.4 mmol), 1-ethyl-3-(3-dimethylaminopropyl) carbodiimide hydrochloride (4.49 g, 23.4 mmol), 1-hydroxybenzotriazole hydrate (12% water, 3.16 g, 23.4 mmol) in DCM (150 mL). After 5 hours, add EtOAc. Extract with 1 N aqueous HCl solution and brine. Dry over sodium sulfate, filter, and concentrate under reduced pressure to give a residue. Purify the residue by silica gel flash chromatography, eluting with 0 to 50% EtOAc/hexanes to give the title compound (2.20 g, 90%). ¹H NMR (400 MHz, CDCl₃) δ 5.90-5.67 (m, 3H), 5.20-5.01 (m, 4H), 3.88 (t, 2H), 2.29 (d, 2H), 1.19 (s, 6H).

Preparation 51

3,3-Dimethyl-1,4-dihydropyridin-2-one

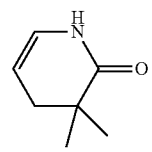

Add (1,3-bis(2,4,6-trimethylphenyl)-2-imidazolidinylidene)dichloro(phenylmethyl-ene)(tricyclohexylphosphine)ruthenium (Grubbs catalyst, 2ⁿᵈ generation, 0.51 g, 0.60 mmol) to a solution of N-allyl-2,2-dimethyl-pent-4-enamide (2.00 g, 12.0 mmol) in toluene (50 mL). Degas the reaction mixture by sparging with nitrogen for 10 min. Heat the mixture at 105° C. for 5 hours and cool to ambient temperature. Concentrate under reduced pressure to give a residue. Purify the residue by silica gel flash chromatography, eluting with 0 to 50% EtOAc/hexanes to give the title compound (1.05 g, 70%). ES/MS (m/z): 126 (M+H).

Preparation 52 tert-Butyl 3,3-dimethyl-2-oxo-3,4-dihydropyridine-1(2H)-carboxylate

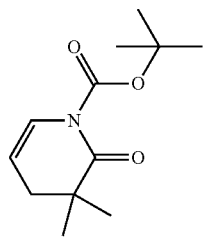 [SMILES: CC(C)(C)OC(=O)N1C=CCC(C)(C)C1=O]

Add DMAP (0.10 g, 0.84 mmol) and di-tert-butyl dicarbonate (3.85 mL, 16.8 mmol) to a solution of 3,3-dimethyl-1,4-dihydropyridin-2-one (1.05 g, 8.39 mmol) in ACN (40 mL). After 1 hour, remove solvents under reduced pressure to give a residue. Purify the residue by silica gel flash chromatography, eluting with 0 to 25% EtOAc/hexanes to give the title compound (1.80 g, 95%). ¹H NMR (400 MHz, CDCl₃) δ 6.78-6.70 (m, 1H), 5.18-5.09 (m, 1H), 2.20-2.15 (m, 2H), 1.53 (s, 9H), 1.22 (s, 6H).

Preparation 53 tert-Butyl 5-iodo-3,3-dimethyl-2-oxo-3,4-dihydropyridine-1(2H)-carboxylate

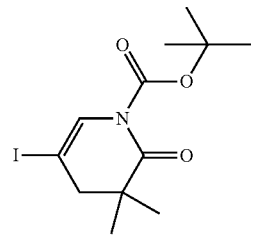 [SMILES: CC(C)(C)OC(=O)N1C=C(I)CC(C)(C)C1=O]

Add N-iodosuccinimide (1.45 g, 6.46 mmol) to a solution of tert-butyl 3,3-dimethyl-2-oxo-3,4-dihydropyridine-1 (2H)-carboxylate (0.97 g, 4.31 mmol) in dimethylformamide (21.5 mL). After 17 hours, quench the reaction with saturated aqueous sodium thiosulfate solution and water. Extract with ether. Combine the organic extracts and wash with water and brine. Dry over sodium sulfate, filter, and concentrate under reduced pressure to give a residue. Purify the residue by silica gel flash chromatography, eluting with 0 to 50% EtOAc/hexanes to give the title compound (0.95 g, 63%). ¹H NMR (400 MHz, CDCl₃) δ 7.20-7.17 (m, 1H), 2.61 (d, 2H), 1.55 (s, 9H), 1.27 (s, 6H).

Preparation 54

3,3-Dimethyl-5-(thiophen-2-yl)-3,4-dihydropyridin-2(1H)-one

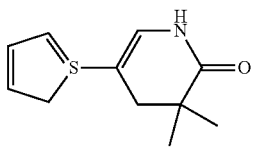

Add 0.5 M 2-thienylzinc bromide solution in THF (10.8 mL, 5.4 mmol) to a solution of tert-butyl 5-iodo-3,3-dimethyl-2-oxo-3,4-dihydropyridine-1(2H)-carboxylate (950 mg, 2.71 mmol) and [1,1'-Bis(diphenylphosphino)ferrocene]dichloropalladium(II), complex with DCM (221 mg, 0.27 mmol) in THF (20 mL). Degas the reaction mixture by sparging with nitrogen for 10 minutes. Heat the mixture at 60° C. for 17 hours and cool to ambient temperature. Quench with 2 N aqueous HCl solution and stir vigorously. Dilute with EtOAc. Separate the organic layer and wash with 1 N aqueous HCl solution, water, and brine, dry over sodium sulfate, filter, and concentrate under reduced pressure to give a residue. Purify the residue by silica gel flash chromatography, eluting with 0 to 50% EtOAc/hexanes to give the title compound (450 mg, 80%). $^1$H NMR (400 MHz, CDCl$_3$) δ 8.41 (br s, 1H), 7.12 (dd, 1H), 6.99 (dd, 1H), 6.91 (dd, 1H), 6.59 (d, 1H), 2.60 (d, 2H), 1.28 (s, 6H).

Preparation 55 racemic 2-Ethyl-2-methylpent-4-enoic acid

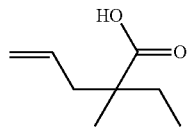

Add 2.5 M n-butyllithium solution in hexanes (28.8 mL, 72.0 mmol) to a dry-ice/acetone cooled solution of diisopropylamine (10.56 mL, 75 mmol) in THF (100 mL) at −78° C. After 15 min, warm the reaction mixture to 0° C. in an ice bath. After 30 min, add 2-methylbutanoic acid (3.28 mL, 30 mmol). After 15 min, remove the cooling bath and warm the reaction mixture to ambient temperature. After 1 hour, cool the reaction mixture to 0° C. in an ice bath. Add allyl iodide (3.01 mL, 33 mmol) and hexamethylphosphoramide (3.00 mL, 17.2 mmol). Allow the reaction mixture to warm up to ambient temperature slowly overnight. After 16 hours, quench the reaction with saturated aqueous ammonium chloride solution. Remove most of the solvents under reduced pressure. Dissolve the residue in EtOAc, extract with 1 N aqueous HCl solution, water, and brine, dry over sodium sulfate, filter, and concentrate under reduced pressure to give the title product (6.09 g, 30 mmol) which is used without further purification: $^1$H NMR (400 MHz, d$_6$-DMSO) δ 12.10 (br s, 1H), 5.78-5.64 (m, 1H), 5.10-5.00 (m, 2H), 2.33-2.08 (m, 2H), 1.60-1.33 (m, 2H), 1.01 (s, 3H), 0.80 (t, 3H).

Preparation 56 racemic N-Allyl-2-ethyl-2-methyl-pent-4-enamide

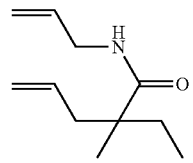

Add 1-ethyl-3-(3-dimethylaminopropyl) carbodiimide hydrochloride (8.63 g, 45.0 mmol), 1-hydroxybenzotriazole hydrate (12% water, 6.08 g, 45.0 mmol) to a solution of crude racemic 2-ethyl-2-methylpent-4-enoic acid (6.09 g, 30 mmol) in DCM (200 mL). Add prop-2-en-1-amine (3.38 mL, 45.0 mmol) and DIPEA (7.85 mL, 45.0 mmol). After 4 hours, add more DCM. Extract with 1 N aqueous HCl solution and brine. Dry over sodium sulfate, filter, and concentrate under reduced pressure to give a residue. Purify the residue by silica gel flash chromatography, eluting with 0 to 50% EtOAc/hexanes to give the title compound (2.20 g, 40%). $^1$H NMR (400 MHz, CDCl$_3$) δ 5.93 (br s, 1H), 5.85-5.59 (m, 2H), 5.17-4.94 (m, 4H), 3.86-3.80 (m, 2H), 2.37 (dd, 1H), 2.09 (dd, 1H), 1.73-1.59 (m, 1H), 1.45-1.34 (m, 1H), 1.08 (s, 3H), 0.80 (t, 3H).

Preparation 57 racemic 3-Ethyl-3-methyl-1,4-dihydropyridin-2-one

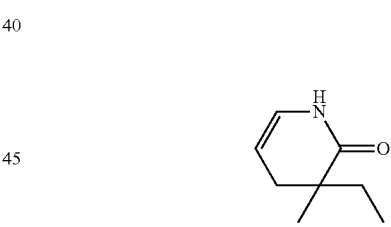

Add (1,3-bis(2,4,6-trimethylphenyl)-2-imidazolidinylidene)dichloro(phenylmethyl-ene)(tricyclohexylphosphine)ruthenium (Grubbs catalyst, 2$^{nd}$ generation, 0.47 g, 0.55 mmol) to a solution of N,4-diallyltetrahydropyran-4-carboxamide (2.00 g, 11.0 mmol) in toluene (60 mL). Degas the reaction mixture by sparging with nitrogen for 5 minutes. Heat the mixture at 100° C. for 5 hours and cool to ambient temperature. Concentrate under reduced pressure to give a residue. Purify the residue by silica gel flash chromatography, eluting with 0 to 50% EtOAc/hexanes to give the title compound (1.10 g, 72%). $^1$H NMR (400 MHz, CDCl$_3$) δ 7.71 (br s, 1H), 6.10-5.98 (m, 1H), 5.07-5.00 (m, 1H), 2.31-2.20 (m, 1H), 2.16-2.07 (m, 1H), 1.70-1.52 (m, 2H), 1.14 (s, 3H), 0.90 (t, 3H).

Preparation 58 racemic tert-Butyl 3-ethyl-3-methyl-2-oxo-3,4-dihydropyridine-1(2H)-carboxylate

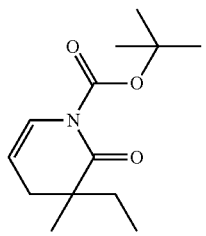 [SMILES: CCC1(C)CC=CN(C(=O)OC(C)(C)C)C1=O]

Add DMAP (100 mg, 0.79 mmol) and di-tert-butyl dicarbonate (3.63 mL, 15.8 mmol) to a solution of 3-ethyl-3-methyl-1,4-dihydropyridin-2-one (1.10 g, 7.90 mmol) in ACN (40 mL). After 2 hours, remove solvents under reduced pressure to give a residue. Purify the residue by silica gel flash chromatography, eluting with 0 to 50% EtOAc/hexanes to give the title compound (2.00 g, 95%). $^1$H NMR (400 MHz, CDCl$_3$) δ 6.76-6.69 (m, 1H), 5.14-5.06 (m, 1H), 2.24-2.18 (m, 2H), 1.82-1.68 (m, 2H), 1.54 (s, 9H), 1.18 (s, 3H), 0.89 (t, 3H).

Preparation 59 racemic tert-Butyl 3-ethyl-5-iodo-3-methyl-2-oxo-3,4-dihydropyridine-1(2H)-carboxylate

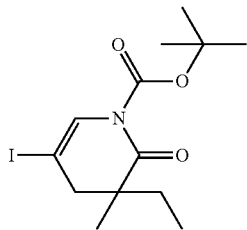 [SMILES: CCC1(C)CC(I)=CN(C(=O)OC(C)(C)C)C1=O]

Add N-iodosuccinimide (1.52 g, 6.77 mmol) to a solution of tert-butyl 3-ethyl-3-methyl-2-oxo-3,4-dihydropyridine-1 (2H)-carboxylate (1.20 g, 4.51 mmol) in dimethylformamide (23 mL). After 17 hours, quench the reaction with saturated aqueous sodium thiosulfate solution and water. Extract four times with ether. Combine all the organic extracts and wash with water and brine. Dry over sodium sulfate, filter, and concentrate under reduced pressure to give a residue. Purify the residue by silica gel flash chromatography, eluting with 0 to 20% EtOAc/hexanes to give the title compound (1.15 g, 70%). ES/MS (m/z): 366 (M+H).

Preparation 60 racemic 3-Ethyl-3-methyl-5-(2-thienyl)-1,4-dihydropyridin-2-one

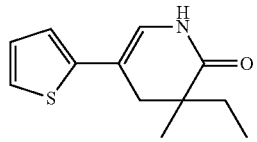

Add 0.5 M 2-thienylzinc bromide solution in THF (4.38 mL, 2.19 mmol) to a solution of tert-butyl 3-ethyl-5-iodo-3-methyl-2-oxo-3,4-dihydropyridine-1(2H)-carboxylate (400 mg, 1.10 mmol) and [1,1'-bis(diphenylphosphino)ferrocene]dichloropalladium(II), complex with DCM (89 mg, 0.11 mmol) in THF (11 mL). Degas the reaction mixture by sparging with nitrogen for 10 minutes. Heat the mixture at 60° C. for 18 hours and cool to ambient temperature. Quench with 2 N aqueous HCl solution and stir vigorously. Dilute with EtOAc. Separate the organic layer and wash with 1 N aqueous HCl solution, water, and brine, dry over sodium sulfate, filter, and concentrate under reduced pressure to give a residue. Purify the residue by silica gel flash chromatography, eluting with 0 to 50% EtOAc/hexanes to give the title compound (180 mg, 74%). ES/MS (m/z): 222 (M+H).

Preparation 61 tert-Butyl-cyclopent-3-en-1-yloxy-diphenyl-silane

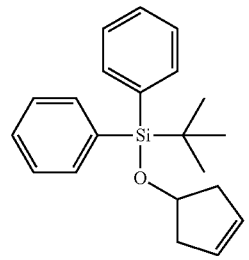 [SMILES: CC(C)(C)[Si](OC1CC=CC1)(c1ccccc1)c1ccccc1]

Add tert-butylchlorodiphenylsilane (36.66 g, 133.38 mmol) to 3-cyclopenten-1-ol (10.2 g, 121.26 mmol) and 1H-imidazole (18.16 g, 266.77 mmol) in dry DMF (100 mL) drop wise at −20° C. After complete addition, allow the reaction temperature to gradually warm to ambient temperature and stir under nitrogen overnight. Add water, ammonium chloride, and EtOAc to the reaction mixture and stir the mixture for 1 hour. Separate the organic layer and wash with ammonium chloride (5×) until pH is acidic, water (2×), and brine, dry over sodium sulfate, filter, and concentrate under reduced pressure to give the title compound (40.22 g, 93%). ES/MS (m/z): 405.2 (M+2 MeCN+H).

Preparation 62 racemic, trans, tert-Butyl-(3,4-dibromocyclopentoxy)-diphenyl-silane

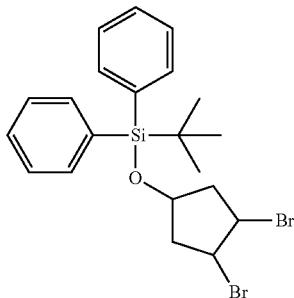 [SMILES: CC(C)(C)[Si](OC1CC(Br)C(Br)C1)(c1ccccc1)c1ccccc1]

Add a solution of bromine (22.23 g, 7.15 mL, 139.10 mmol) in carbon tetrachloride (10 mL) drop wise over 20 minutes to a stirred solution of tert-butyl-cyclopent-3-en-1-yloxy-diphenyl-silane (40.2 g, 115.92 mmol) in carbon tetrachloride (200 mL) and ethanol (0.1 mL) at −20° C. Continue to stir in cooling bath for another hour. Pour the reaction mixture into saturated sodium bicarbonate. Separate the organic layer. Wash the organic extract with brine, dry over sodium sulfate, filter, and concentrate under reduced pressure to give the title compound (55.19 g, 106.41 mmol, 93%). GCMS 425 (M−56).

Preparation 63 racemic (3-Bromocyclopent-3-en-1-yl)oxy-tert-butyl-diphenyl-silane

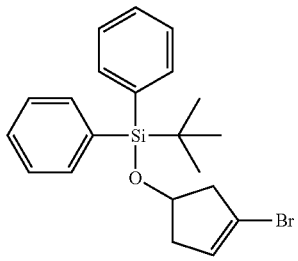 [SMILES: CC(C)(C)[Si](OC1CC=C(Br)C1)(c1ccccc1)c1ccccc1]

Prepare a stock solution of trans, racemic tert-butyl-(3,4-dibromocyclopentoxy)-diphenyl-silane (50.44 g, 104.58 mmol) in dry THF (500 mL) and split in two portions. Add solid sodium amide (5.2 g, 130.5 mmol) and solid sodium tert-butoxide (18 g, 188 mmol). Stir resulting cream colored mixtures of each vessel at room temperature for 29 hours. GCMS shows 85:15 product/starting material in flask one and completion in flask two. Add additional 0.5 equivalent of sodium amide to flask one and let it stir for another 24 hours. Quench flask two with saturated ammonium chloride, extract with ether (3×). Combine organic extracts and wash with brine, dry over sodium sulfate, filter, and concentrate under reduced pressure to give a brown oil. Complete the same work-up for each reaction. Combine both portions and purify the residue by silica gel flash chromatography eluting with hexane: 5% DCM in hexane with a gradient of 20-50% to give the title compound (18.45 g, 43.95%). GCMS (M−56) 345.1.

Preparation 64 racemic 5-[4-[tert-Butyl(diphenyl)silyl]oxycyclopenten-1-yl]-N-(6-fluoro-1-oxo-1,2-dihydroisoquinolin-7-yl)thiophene-2-sulfonamide

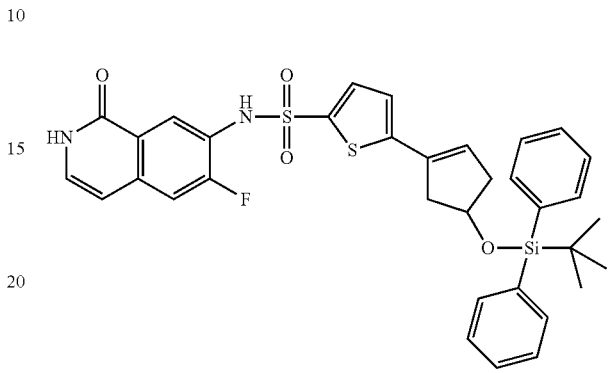

Add racemic (3-bromocyclopent-3-en-1-yl)oxy-tert-butyl-diphenyl-silane (2.71 g, 6.75 mmol), bis(pinocolato)diboron (5.14 g, 20.25 mmol), (1,1'-bis(diphenylphosphino)ferrocene)palladium (II) chloride (330.79 mg, 0.405 mmol), potassium acetate (4.64 g, 47.26 mmol) to 1,4-dioxane (60 mL). Heat the reaction mixture at 100° C. for 2 hours. Let the reaction mixture cool to room temperature. Add water and extract with EtOAc. Dry the organic layer over sodium sulfate, filter, and concentrate under reduced pressure. Purify the crude by silica gel flash chromatography eluting with DCM:MeOH (90:10) to give the intermediate boronate. Combine 5-bromo-N-(6-fluoro-1-oxo-1,2-dihydroisoquinolin-7-yl)thiophene-2-sulfonamide (2.1 g, 5.21 mmol), tert-butyl-diphenyl-[3-(4,4,5,5-tetramethyl-1,3,2-dioxaborolan-2-yl)cyclopent-3-en-1-yl]oxy-silane (3.50 g, 7.81 mmol), tetrakis(triphenylphosphine)palladium (481.43 mg, 0.416 mmol), and potassium phosphate, tribasic, N-hydrate (3.57 g, 16.82 mmol) with 1,4-dioxane (10 mL) and water (5 mL) in a microwave vial. Place the vial in Biotage initiator and heat to 140° C. for 20 minutes. Add water and then 1 N HCl to make solution acidic. Extract the mixture with EtOAc (3×). Combine the organic extracts and dry over sodium sulfate, filter, and concentrate under reduced pressure. Purify the crude material by silica gel flash chromatography eluting with DCM:MeOH (90:10) to give the title compound (210 mg, 7%). ES/MS (m/z): 643.0 (M−H).

Preparation 65 racemic 5-(4-{[tert-Butyl(dimethyl)silyl]oxy}cyclohex-1-en-1-yl)-N-(6-fluoro-1-oxo-1,2-dihydroisoquinolin-7-yl)thiophene-2-sulfonamide

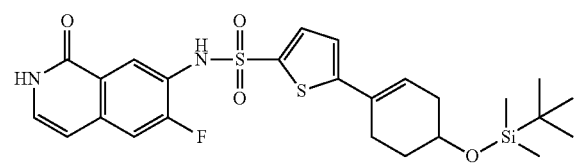 [SMILES: CC(C)(C)[Si](C)(C)OC1CC=C(c2ccc(S(=O)(=O)Nc3cc4c(=O)[nH]ccc4cc3F)s2)CC1]

Combine 5-bromo-N-(6-fluoro-1-oxo-1,2-dihydroisoquinolin-7-yl)thiophene-2-sulfonamide (0.6 g, 1.49 mmol), tert-butyl-dimethyl-[4-(4,4,5,5-tetramethyl-1,3,2-dioxaborolan-2-yl)cyclohex-3-en-1-yl]oxy-silane (1.01 g, 2.98 mmol), tetrakis(triphenylphosphine)palladium (0.138 g, 0.119 mmol), and potassium phosphate, tribasic, N-hydrate (1.02 g, 4.81 mmol) with 1,4-dioxane (8 mL) and water (4 mL) in a microwave vial. Place the vial in Biotage initiator and heat to 140° C. for 20 minutes. Add water and then 1 N hydrochloric acid to make solution acidic. Extract the mixture with EtOAc (3×). Combine the organic extracts and dry over sodium sulfate, filter, and concentrate under reduced pressure to give dark brown grease. Add DCM to the grease. After a few minutes, a solid precipitates out from solution. Filter the solid to give the title compound (0.513 g, 64.5%). ES/MS (m/z): 535.2 (M+H).

Preparation 66

5-(4-{[tert-Butyl(dimethyl)silyl]oxy}cyclohex-1-en-1-yl)-N-(6-fluoro-1-oxo-1,2-dihydroisoquinolin-7-yl)thiophene-2-sulfonamide, Isomer 1

Preparation 67

5-(4-{[tert-Butyl(dimethyl)silyl]oxy}cyclohex-1-en-1-yl)-N-(6-fluoro-1-oxo-1,2-dihydroisoquinolin-7-yl)thiophene-2-sulfonamide, Isomer 2

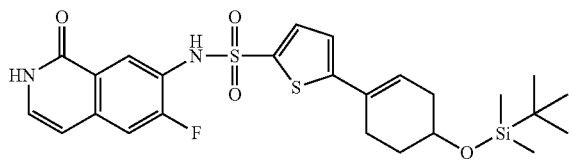 [SMILES: CC(C)(C)[Si](C)(C)OC1CC=C(c2ccc(S(=O)(=O)Nc3cc4c(=O)[nH]ccc4cc3F)s2)CC1]

Beginning with racemic 5-(4-{[tert-butyl(dimethyl)silyl]oxy}cyclohex-1-en-1-yl)-N-(6-fluoro-1-oxo-1,2-dihydroisoquinolin-7-yl)thiophene-2-sulfonamide (0.575 g, 1.08 mmol), separate the enantiomers with chiral chromatography using Chiralpak AD-H, 21×250 mm column eluting with 30% IPA:70% $CO_2$ at flow rate of 70 g/min to give Preparation 66, Isomer 1 (0.222 g, 38%, >99% ee), ES/MS (m/z): 535.0 (M+H) and Preparation 67, Isomer 2 (0.216 g, 38%, 99% ee), ES/MS (m/z): 535.0 (M+H).

Example 1

N-(6-Fluoro-1-oxo-1,2-dihydroisoquinolin-7-yl)-5-[(3R)-3-hydroxypyrrolidin-1-yl]thiophene-2-sulfonamide

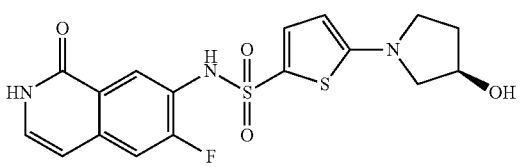 [SMILES: O=c1[nH]ccc2cc(F)c(NS(=O)(=O)c3ccc(N4CC[C@@H](O)C4)s3)cc12]

Combine 5-bromo-N-(6-fluoro-1-oxo-1,2-dihydroisoquinolin-7-yl)thiophene-2-sulfonamide (0.59 g, 1.47 mmol), (R)-3-pyrrolidinol (0.265 g, 3.04 mmol), copper(I)bromide (0.052 g, 0.36 mmol), hydroxyproline (0.10 g, 0.8 mmol) and cesium carbonate (1.03 g, 3.16 mmol) with DMSO (8 mL) in a sealed vial and heat the resulting mixture overnight at 100° C. Dilute the reaction mixture with water and adjust the pH to approximately 5. Extract the aqueous mixture with EtOAc and followed by DCM containing a small amount of MeOH. Decant water away from any product containing solids and take solids up in 50/50 DCM/MeOH. Combine and concentrate all organics under reduced pressure to give a residue. Purify the resulting residue on silica gel flash chromatography, eluting with 0-10% MeOH/DCM. Concentrate the appropriate material from EtOAc/hexanes and dry to give the title compound (0.16 g, 27%) as a tan solid. ES/MS (m/z): 410 (M+H).

The following compounds are prepared essentially by the procedure described for Example 1.

TABLE 4

| Ex No. | Chemical Name | Structure | ES/MS (m/z) (M + 1) |
|---|---|---|---|
| 2 | racemic N-(6-Fluoro-1-oxo-1,2-dihydroisoquinolin-7-yl)-5-[3-hydroxypiperidin-1-yl]thiophene-2-sulfonamide | 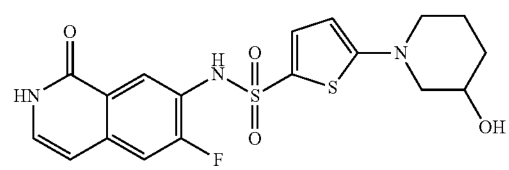 [SMILES: O=c1[nH]ccc2cc(F)c(NS(=O)(=O)c3ccc(N4CCCC(O)C4)s3)cc12] | 424 |
| 3 | N-(6-Fluoro-1-oxo-1,2-dihydroisoquinolin-7-yl)-5-[(3S)-3-hydroxypiperidin-1-yl]thiophene-2-sulfonamide | 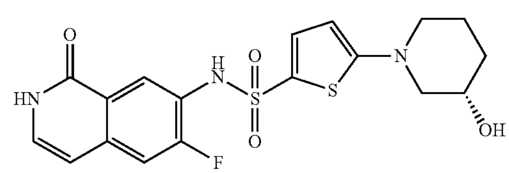 [SMILES: O=c1[nH]ccc2cc(F)c(NS(=O)(=O)c3ccc(N4CCC[C@H](O)C4)s3)cc12] | 424 |

TABLE 4-continued

| Ex No. | Chemical Name | Structure | ES/MS (m/z) (M + 1) |
|---|---|---|---|
| 4 | N-(6-Fluoro-1-oxo-1,2-dihydroisoquinolin-7-yl)-5-[(3R)-3-hydroxypiperidin-1-yl]thiophene-2-sulfonamide | 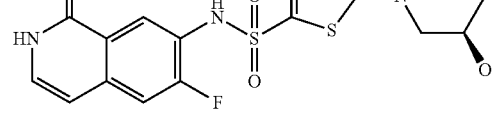 | 424 |
| 5 | N-(6-Fluoro-1-oxo-1,2-dihydroisoquinolin-7-yl)-5-(4-hydroxypiperidin-1-yl)thiophene-2-sulfonamide | 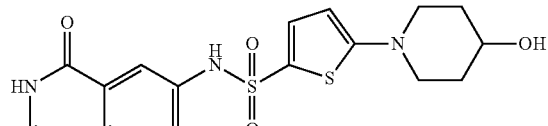 | 424 |
| 6 | N-(6-fluoro-1-oxo-1,2-dihydroisoquinolin-7-yl)-5-[4-hydroxy-4-(trifluoromethyl)piperidin-1-yl]thiophene-2-sulfonamide | 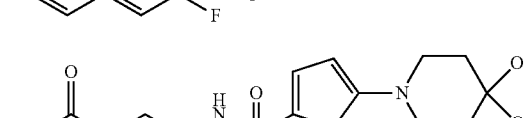 | 492 |
| 7 | racemic N-(6-Fluoro-1-oxo-1,2-dihydroisoquinolin-7-yl)-5-[3-hydroxypyrrolidin-1-yl]thiophene-2-sulfonamide | 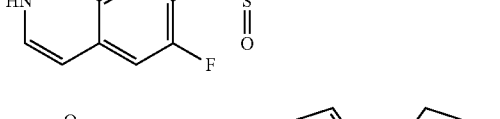 | 410 |
| 8 | N-(6-Fluoro-1-oxo-1,2-dihydroisoquinolin-7-yl)-5-[(3S)-3-hydroxypyrrolidin-1-yl]thiophene-2-sulfonamide | 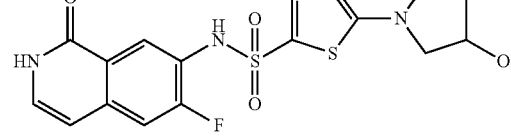 | 410 |
| 9 | cis meso-5-(3,5-Dihydroxypiperidin-1-yl)-N-(6-fluoro-1-oxo-1,2-dihydroisoquinolin-7-yl)thiophene-2-sulfonamide | 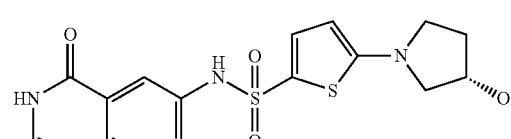 | 440.0 |
| 10 | racemic N-(6-Fluoro-1-oxo-1,2-dihydroisoquinolin-7-yl)-5-[4-hydroxy-3,3-dimethylpyrrolidin-1-yl]thiophene-2-sulfonamide | 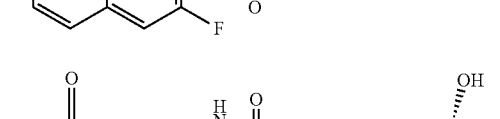 | 438.2 |
| 11 | racemic trans N-(6-Fluoro-1-oxo-1,2-dihydroisoquinolin-7-yl)-5-[3-hydroxy-4-methoxypyrrolidin-1-yl]thiophene-2-sulfonamide | 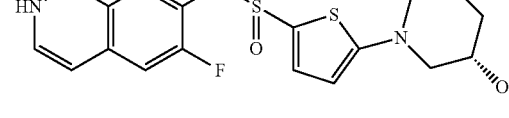 | 440.0 |

TABLE 4-continued

| Ex No. | Chemical Name | Structure | ES/MS (m/z) (M + 1) |
|---|---|---|---|
| 12 | trans N-(6-Fluoro-1-oxo-1,2-dihydroisoquinolin-7-yl)-5-[3-hydroxy-4-methoxypyrrolidin-1-yl]thiophene-2-sulfonamide, Isomer 1 | 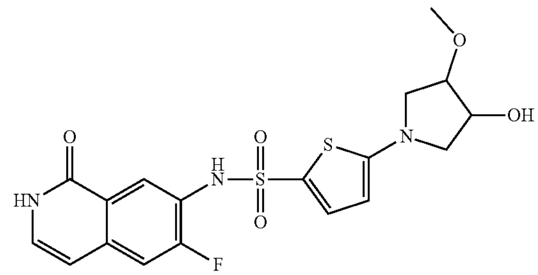 [SMILES: COC1CN(c2ccc(S(=O)(=O)Nc3cc4c(=O)[nH]ccc4cc3F)s2)CC1O] | 440.1 |
| 13 | trans N-(6-Fluoro-1-oxo-1,2-dihydroisoquinolin-7-yl)-5-[-3-hydroxy-4-methoxy pyrrolidin-1-yl]thiophene-2-sulfonamide, Isomer 2 | 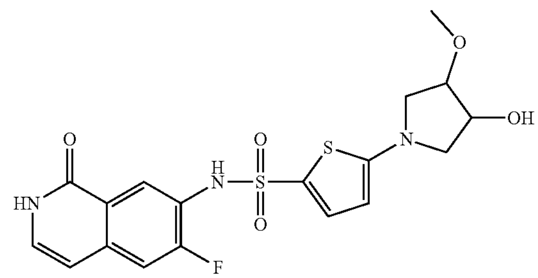 [SMILES: COC1CN(c2ccc(S(=O)(=O)Nc3cc4c(=O)[nH]ccc4cc3F)s2)CC1O] | 440.1 |
| 14 | N-(6-Fluoro-1-oxo-1,2-dihydroisoquinolin-7-yl)-5-[(4S)-4-hydroxy-3,3-dimethylpyrrolidin-1-yl]thiophene-2-sulfonamide | 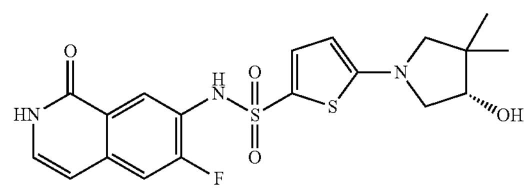 [SMILES: CC1(C)CN(c2ccc(S(=O)(=O)Nc3cc4c(=O)[nH]ccc4cc3F)s2)C[C@H]1O] | 438.1 |
| 15 | N-(6-Fluoro-1-oxo-1,2-dihydroisoquinolin-7-yl)-5-[(4R)-4-hydroxy-3,3-dimethylpyrrolidin-1-yl]thiophene-2-sulfonamide | 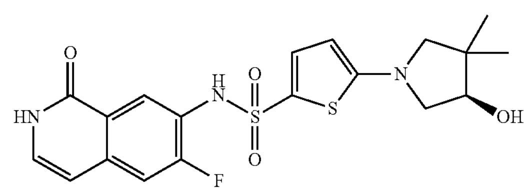 | 438.2 |
| 16 | racemic trans 5-[3,4-Dihydroxypyrrolidin-1-yl]-n-(6-fluoro-1-oxo-1,2-dihydroisoquinolin-7-yl)thiophene-2-sulfonamide | 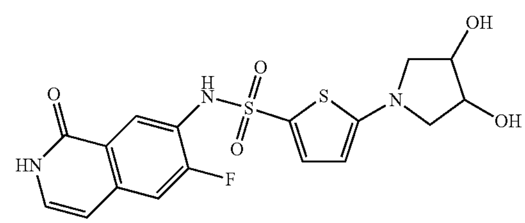 [SMILES: O=c1[nH]ccc2cc(F)c(NS(=O)(=O)c3ccc(N4CC(O)C(O)C4)s3)cc12] | 425.9 |
| 17 | 5-[(3S,4S)-3,4-Dihydroxypyrrolidin-1-yl]-N-(6-fluoro-1-oxo-1,2-dihydroisoquinolin-7-yl)thiophene-2-sulfonamide | 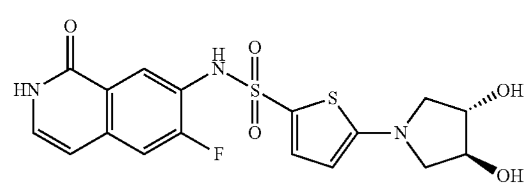 [SMILES: O=c1[nH]ccc2cc(F)c(NS(=O)(=O)c3ccc(N4C[C@H](O)[C@@H](O)C4)s3)cc12] | 426.0 |
| 18 | 5-[(3S,4S)-3-(Dimethylamino)-4-hydroxypyrrolidin-1-yl]-N-(6-fluoro-1-oxo-1,2-dihydroisoquinolin-7-yl)thiophene-2-sulfonamide | 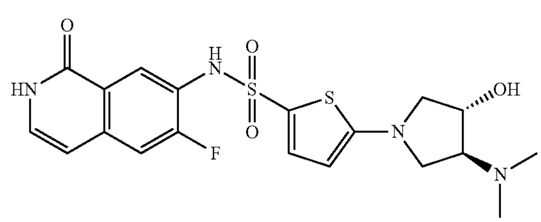 [SMILES: CN(C)[C@H]1CN(c2ccc(S(=O)(=O)Nc3cc4c(=O)[nH]ccc4cc3F)s2)C[C@@H]1O] | 453.0 |

TABLE 4-continued

| Ex No. | Chemical Name | Structure | ES/MS (m/z) (M + 1) |
|---|---|---|---|
| 19 | 5-[(3R,4R)-3,4-Dihydroxypyrrolidin-1-yl]-N-(6-fluoro-1-oxo-1,2-dihydroisoquinolin-7-yl)thiophene-2-sulfonamide | 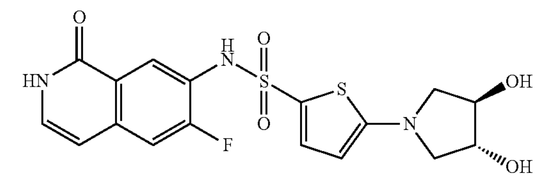 [SMILES: O=c1[nH]ccc2cc(F)c(NS(=O)(=O)c3ccc(N4C[C@@H](O)[C@H](O)C4)s3)cc12] | 426.0 |
| 20 | racemic trans 5-[3,4-Dihydroxypiperidin-1-yl]-N-(6-fluoro-1-oxo-1,2-dihydroisoquinolin-7-yl)thiophene-2-sulfonamide | 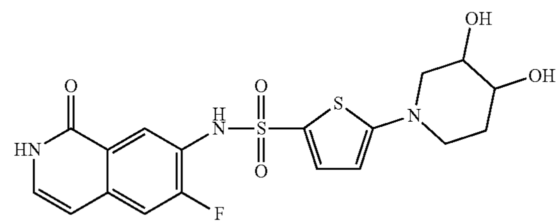 [SMILES: O=c1[nH]ccc2cc(F)c(NS(=O)(=O)c3ccc(N4CCC(O)C(O)C4)s3)cc12] | 440 |
| 21 | N-(6-Fluoro-1-oxo-1,2-dihydroisoquinolin-7-yl)-5-[(3S,4S)-3-hydroxy-4-(morpholin-4-yl) pyrrolidin-1-yl]thiophene-2-sulfonamide | 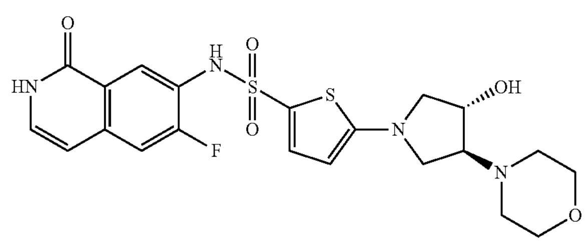 [SMILES: O=c1[nH]ccc2cc(F)c(NS(=O)(=O)c3ccc(N4C[C@H](O)[C@@H](N5CCOCC5)C4)s3)cc12] | 495 |

Alternate Preparation, Example 1

Add (R)-3-pyrrolidinol (23.5 g, 269.9 mmol) and DIPEA (126 mL; 719.8 mmol) to a solution of 5-bromo-N-(6-fluoro-1-oxo-1,2-dihydroisoquinolin-7-yl)thiophene-2-sulfonamide (70 g, 180 mmol, 88% purity) in pyridine (430 mL) and heat the resulting mixture at 105° C. (internal temperature) for 5 hours. Concentrate the mixture under high vacuum at 40° C. Purify the residue through a pad of silica gel eluting with acetone/hexane 1:1 to acetone 100%. Slurry the material obtained in CH₂Cl₂ (200 mL) for 30 minutes. Filter the precipitated solid, wash with CH₂Cl₂ (2×100 mL), dry, and collect to give the title compound (32 g, 43%) as a beige solid. ES/MS (m/z): 410 (M+H).

Example 22

5-[(1E)-N-Hydroxyethanimidoyl]-N-(1-oxo-1,2-dihydroisoquinolin-7-yl)thiophene-2-sulfonamide

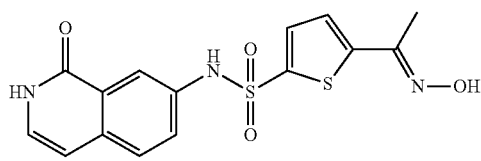 [SMILES: C/C(=N\O)c1ccc(S(=O)(=O)Nc2ccc3cc[nH]c(=O)c3c2)s1]

Combine 5-acetyl-N-(6-fluoro-1-oxo-1,2-dihydroisoquinolin-7-yl)thiophene-2-sulfonamide (0.5 g, 1.4 mmol) with hydroxylamine hydrochloride (0.21 g, 3.0 mmol) in ethanol (20 mL, 343.5 mmol) and heat the mixture overnight at 80° C. under nitrogen. Concentrate the reaction mixture under reduced pressure to give a residue. Dilute the residue with water, adjust the pH to approximately 5, and extract the mixture with EtOAc. Dry the combined extracts over Na₂SO₄ and concentrate the solution under reduced pressure to a residue. Purify the residue by silica gel flash chromatography, eluting with 0-10% MeOH/DCM. Concentrate eluting fractions which are predominantly enriched in the oxime isomer (E isomer). Triturate the material in diethyl ether, collect the precipitate, and dry to give the title compound (0.127 g, 24%, 9:1 E/Z mixture). LC/MS (m/z): 364 (M+H).

The following compounds are prepared essentially by the procedure of Example 22 using the appropriate ketone.

TABLE 5

| Ex No. | Chemical Name | Structure | ES/MS (m/z) (M + 1) |
|---|---|---|---|
| 23 | 5-[(1E)-N-Hydroxy-2-methoxyethanimidoyl]-N-(1-oxo-1,2-dihydroisoquinolin-7-yl)thiophene-2-sulfonamide | 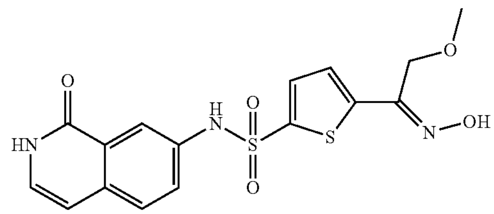 [SMILES: COC/C(=N\O)c1ccc(S(=O)(=O)Nc2ccc3cc[nH]c(=O)c3c2)s1] | 394 |
| 24 | N-(6-Fluoro-1-oxo-1,2-dihydroisoquinolin-7-yl)-5-[(1E)-N-hydroxy-2-methoxyethanimidoyl]thiophene-2-sulfonamide | 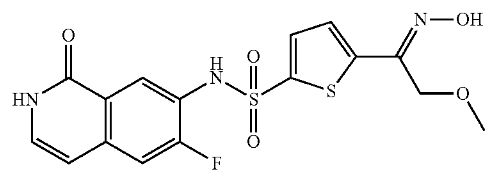 [SMILES: COC/C(=N\O)c1ccc(S(=O)(=O)Nc2cc3c(=O)[nH]ccc3cc2F)s1] | 410 (M − H) |

Example 25 cis N-(6-Fluoro-1-oxo-1,2-dihydroisoquinolin-7-yl)-5-[3-hydroxy-4-methoxypyrrolidin-1-yl]thiophene-2-sulfonamide, Isomer 1

Example 26 cis N-(6-Fluoro-1-oxo-1,2-dihydroisoquinolin-7-yl)-5-[3-hydroxy-4-methoxypyrrolidin-1-yl]thiophene-2-sulfonamide, Isomer 2

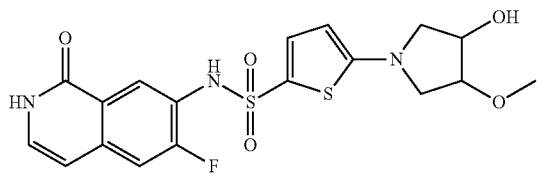 [SMILES: COC1CN(c2ccc(S(=O)(=O)Nc3cc4c(=O)[nH]ccc4cc3F)s2)CC1O]

Prepare Examples 25 and 26 essentially as described in Example 1 except potassium carbonate is used instead of cesium carbonate and the pH is adjusted to 4 instead of pH 5. Purify the crude material and then repurify the residue by reverse phase flash chromatography (H$_2$O with 10% TFA: ACN with 10% TFA), gradient: 15% ACN with 10% TFA isocratic for 3 minutes 15-30% for 5 minutes to give a mixture of cis-isomers (66 mg, 0.15 mmol). Separate the enantiomers by chiral chromatography as described by Examples 33 and 34 using the following different parameters: Chiralpak IA, 21×250 mm; BPR Set Point: 10$^3$ kPa. Obtain the first eluting peak as Example 25, Isomer 1 (0.027 g, 4%, R$_t$=3.18 min; >99% ee), MS (m/z): 440 (M+H). Obtain the second eluting peak as Example 26, Isomer 2 (0.023 g, 3%, R$_t$=3.83 min; 97.5% ee), MS (m/z): 440 (M+H).

Example 27 racemic cis 5-[3,4-Dihydroxypiperidin-1-yl]-N-(6-fluoro-1-oxo-1,2-dihydroisoquinolin-7-yl)thiophene-2-sulfonamide

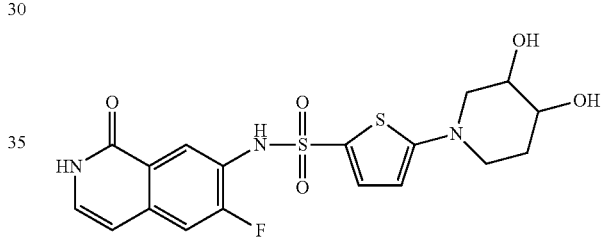

Combine 5-fluoro-N-(6-fluoro-1-oxo-1,2-dihydroisoquinolin-7-yl)thiophene-2-sulfonamide (100 mg, 0.29 mmol), cis-piperidine-3,4-diol hydrochloride (mixture of enantiomers 53.9 mg, 0.35 mmol), dimethylformamide (0.3M, 1 mL) and diisopropylamine (200 µL) and heat in a sealed vial at 100° C. for 18 hours. Cool to ambient temperature and evaporate. Purify by silica gel chromatography with a 1-10% MeOH/DCM gradient to give the title compound as a mixture of cis enantiomers (83.5 mg, 65%). ES/MS (m/z): 440 (M+1).

Example 28

Sodium (6-fluoro-1-oxo-1,2-dihydroisoquinolin-7-yl){[5-(4-hydroxypiperidin-1-yl)thiophen-2-yl]sulfonyl}azanide

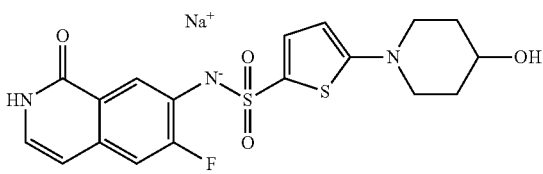 [SMILES: O=c1[nH]ccc2cc(F)c([N-]S(=O)(=O)c3ccc(N4CCC(O)CC4)s3)cc12 ; [Na+]]

Combine N-(6-fluoro-1-oxo-1,2-dihydroisoquinolin-7-yl)-5-(4-hydroxypiperidin-1-yl)thiophene-2-sulfonamide (Example 5) (1 g, 2.4 mmol), 2-propanol (10 mL, 131 mmol), and 1 N aqueous sodium hydroxide solution (2.4 mL, 2.4 mmol). Heat the mixture to dissolve all solids and filter warm through a 0.45 μM syringe filter. Heat to dissolve any resulting precipitate, and then stir the mixture at room temperature to allow crystallization. Filter the solid, wash with 2-propanol, and dry under vacuum at 50° C. to give the title compound (920 mg, 2.1 mmol). ES/MS (m/z): 424 (M+H for the free acid).

The following compound is prepared essentially by the procedure for Example 28.

TABLE 6

| Ex No. | Chemical Name | Structure | ES/MS (m/z) |
|---|---|---|---|
| 29 | Sodium (6-fluoro-1-oxo-1,2-dihydroisoquinolin-7-yl)({5-[(3R)-3-hydroxypyrrolidin-1-yl]thiophen-2-yl}sulfonyl)azanide | 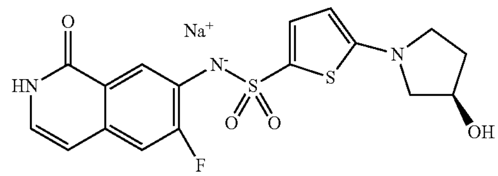 [SMILES: O=c1[nH]ccc2cc(F)c([N-]S(=O)(=O)c3ccc(N4CC[C@@H](O)C4)s3)cc12 ; [Na+]] | 410 |

Example 30 racemic cis 5-(3-Fluoro-4-hydroxypyrrolidin-1-yl-N-(6-fluoro-1-oxo-1,2-dihydroisoquinolin-7-yl)thiophene-2-sulfonamide

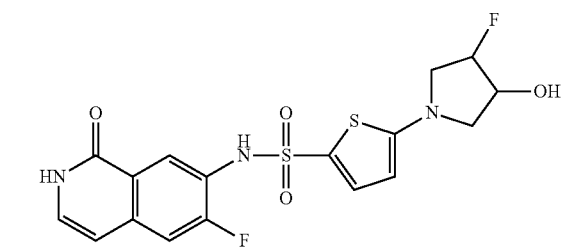

Add TFA (6 mL, 79 mmol) to a solution of tert-butyl (3R,4S)-3-fluoro-4-hydroxy-pyrrolidine-1-carboxylate (1.0 g, 4.87 mmol) in DCM (12 mL). Stir for 1 hour. Concentrate under reduced pressure and dry overnight on high vacuum. Combine with 5-bromo-N-(6-fluoro-1-oxo-1,2-dihydroisoquinolin-7-yl)thiophene-2-sulfonamide (1.0 g, 2.48 mmol), copper bromide (0.11 g, 0.74 mmol) hydroxyproline (0.2 g, 1.5 mmol) and potassium carbonate (1.37 g, 9.92 mmol) in DMSO (12 mL). Microwave for 2 hours at 110° C. Purify the oil via reverse phase chromatography. $H_2O$ with 0.1% formic acid 5% isocratic for 5 min, then 5-50% ACN with 0.1% formic acid. Concentrate under reduced pressure to an oil to give the title compound (244 mg, 23.0%). LC/MS m/e 428 [M+H]$^+$ The following compounds are prepared essentially by the procedures of Example 30.

TABLE 7

| Ex. No. | Chemical Name | Structure | ES/MS (m/z) (M + 1) |
|---|---|---|---|
| 31 | racemic trans 5-(3-Fluoro-4-hydroxypyrrolidin-1-yl-N-(6-fluoro-1-oxo-1,2-dihydroisoquinolin-7-yl)thiophene-2-sulfonamide | 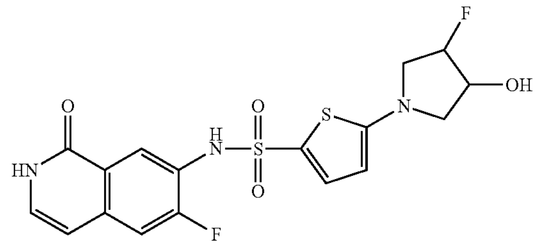 [SMILES: O=c1[nH]ccc2cc(F)c(NS(=O)(=O)c3ccc(N4CC(O)C(F)C4)s3)cc12] | 428 |
| 32 | cis meso 5-[(3R,4S)-3,4-Dihydroxypyrrolidin-1-yl]-N-(6-fluoro-1-oxo-1,2-dihydroisoquinolin-7-yl)thiophene-2-sulfonamide | 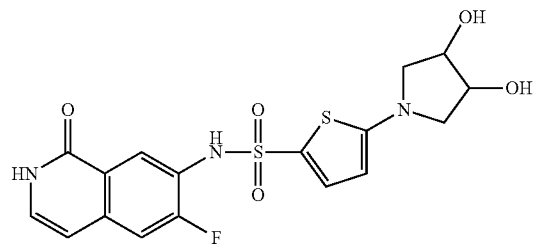 [SMILES: O=c1[nH]ccc2cc(F)c(NS(=O)(=O)c3ccc(N4CC(O)C(O)C4)s3)cc12] | 426 |

Example 33

5-[(3S,4R)-3-fluoro-4-hydroxypyrrolidin-1-yl]-N-(6-fluoro-1-oxo-1,2-dihydroisoquinolin-7-yl)thiophene-2-sulfonamide

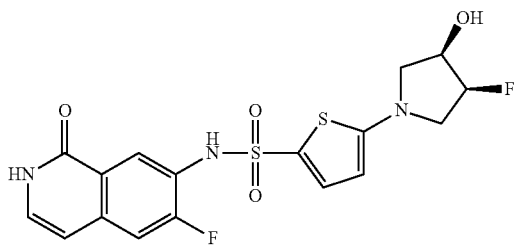 [SMILES: O=c1[nH]ccc2cc(F)c(NS(=O)(=O)c3ccc(N4C[C@@H](O)[C@@H](F)C4)s3)cc12]

Dissolve racemic, cis 5-(3-fluoro-4-hydroxypyrrolidin-1-yl-N-(6-fluoro-1-oxo-1,2-dihydroisoquinolin-7-yl)thiophene-2-sulfonamide (244 mg, 0.57 mmol) in 2.5 mL of MeOH and 0.5 mL of DCM and a few drops of isopropylamine and purify by chiral chromatography using the following parameters—Column: Chiralpak AD-H, 150× 21.2 mm; Flow Rate: 70 mL/min; Detection: 320 nm; Mobile Phase: 40% MeOH/60% $CO_2$; Column Temperature: 35° C.; BPR Set Point: 100 bar; BPR Temperature: 40° C. Collect the first eluting peak as title compound Example 33 (75 mg, 30.8%, $R_t$=2.20 min; 96.8% ee), ES/MS (m/z): 428 (M+H). Collect the second eluting peak as title compound Example 34 (71 mg, 29.2%, $R_t$=3.31 min, 99% ee), ES/MS (m/z): 428 (M+H).

Example 34

5-[(3R,4S)-3-fluoro-4-hydroxypyrrolidin-1-yl]-N-(6-fluoro-1-oxo-1,2-dihydroisoquinolin-7-yl)thiophene-2-sulfonamide

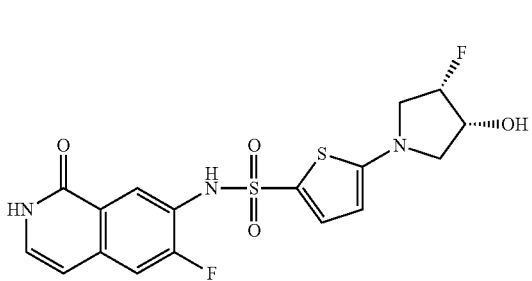

Example 35

5-[(3S,4S)-3-Fluoro-4-hydroxypyrrolidin-1-yl]-N-(6-fluoro-1-oxo-1,2-dihydroisoquinolin-7-yl)thiophene-2-sulfonamide

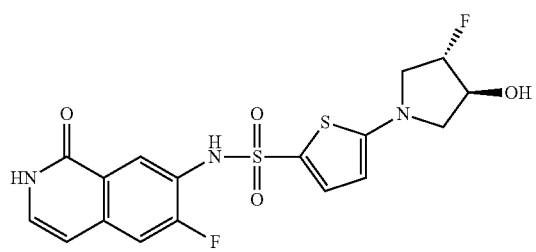

Example 36

5-[(3R,4R)-3-Fluoro-4-hydroxypyrrolidin-1-yl]-N-(6-fluoro-1-oxo-1,2-dihydroisoquinolin-7-yl)thiophene-2-sulfonamide

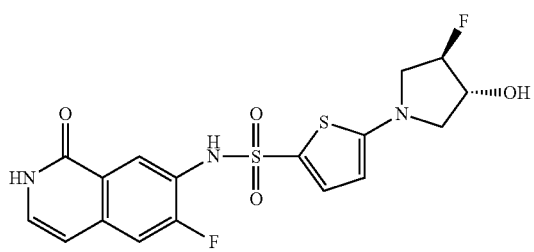

Resolve enantiomers from the racemic mixture as described in Examples 33 and 34 using the following parameters: Column: Chiralpak AD-H, 21.2×250 mm; Detection: 225 nm; Obtain the first eluting peak as the title compound Example 35, (46 mg; $R_t$=1.58 min; 99% ee), ES/MS (m/z): 428 (M+H). Repeat the chiral purification with (293 mg, 0.69 mmol) to obtain the second eluting peak as Example 36 (129 mg, $R_t$=2.9 min; 96.8% ee), ES/MS (m/z): 428 (M+H).

Example 37 racemic 5-(3,3-Difluoro-4-hydroxypyrrolidin-1-yl)-N-(6-fluoro-1-oxo-1,2-dihydroisoquinolin-7-yl)thiophene-2-sulfonamide

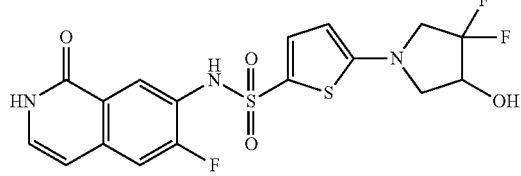

Heat a solution of 5-fluoro-N-(6-fluoro-1-oxo-1,2-dihydroisoquinolin-7-yl)thiophene-2-sulfonamide (2.50 g, 7.30 mmol) and 4,4-difluoropyrrolidin-3-ol (1.90 g, 15.4 mmol) in pyridine (50 mL) at 110° C. for 40 hours and cool to ambient temperature. Remove the solvents under reduced pressure. Purify the residue by reverse phase chromatography, mobile phase A: 0.1% TFA in water, mobile phase B: 0.1% TFA in ACN. Elute with 10 to 45% B in A. Further purify the residue by silica gel flash chromatography, eluting with 2.5 to 7.5% MeOH/DCM to give the title compound (1.70 g, 52%). ES/MS m (m/z): 446 (M+H).

Example 38

5-[(4S)-3,3-Difluoro-4-hydroxypyrrolidin-1-yl]-N-(6-fluoro-1-oxo-1,2-dihydroisoquinolin-7-yl)thiophene-2-sulfonamide; propan-2-amine

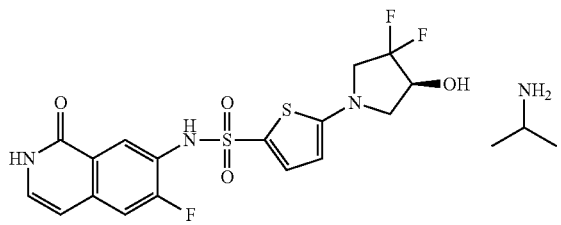

Example 39

5-[(4R)-3,3-Difluoro-4-hydroxypyrrolidin-1-yl]-N-(6-fluoro-1-oxo-1,2-dihydroisoquinolin-7-yl)thiophene-2-sulfonamide-propan-2-amine

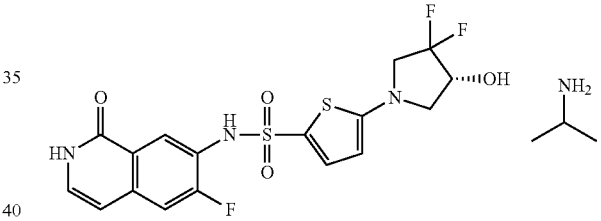

Resolve the enantiomers from the racemic mixture (Example 37) as described in Examples 33 and 34 using the following parameters: Column: Lux Amylose-2, 21.2×250 mm; Detection: 225 nm; Mobile Phase: 30% MeOH (0.2% IPA)/70% $CO_2$. Obtain the first eluting peak as the title compound Example 38 (54 mg, $R_t$=3.22 min; 99% ee), ES/MS (m/z): 446 (M+H). Obtain the second eluting peak as the title compound Example 39 (48 mg, $R_t$=4.43 min; 99% ee), ES/MS (m/z): 446 (M+H).

The following compounds are prepared essentially as described for Examples 38 and 39.

TABLE 8

| Ex. No. | Chemical Name | Structure | ES/MS (m/z) (M + 1) |
|---|---|---|---|
| 40* | 5-[(4S)-3,3-difluoro-4-hydroxypyrrolidin-1-yl]-N-(6-fluoro-1-oxo-1,2-dihydroisoquinolin-7-yl)thiophene-2-sulfonamide | 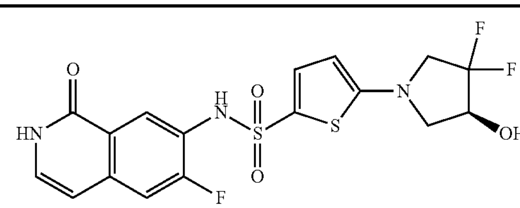 | 446 |

TABLE 8-continued

| Ex. No. | Chemical Name | Structure | ES/MS (m/z) (M + 1) |
|---|---|---|---|
| 41* | 5-[(4R)-3,3-difluoro-4-hydroxypyrrolidin-1-yl]-N-(6-fluoro-1-oxo-1,2-dihydroisoquinolin-7-yl)thiophene-2-sulfonamide | 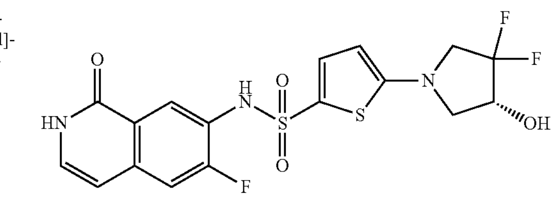 | 446 |

*Dissolve the optically pure compounds in 4:1 DCM/IPA and extract with 0.1N aqueous HCl solution and brine, dry over magnesium sulfate, filter, and concentrate under reduced pressure to give the examples above.

Example 42 racemic trans N-(6-Fluoro-1-oxo-1,2-dihydroisoquinolin-7-yl)-5-(3-hydroxycyclopentyl)thiophene-2-sulfonamide

Example 43 racemic cis N-(6-Fluoro-1-oxo-1,2-dihydroisoquinolin-7-yl)-5-(3-hydroxycyclopentyl)thiophene-2-sulfonamide

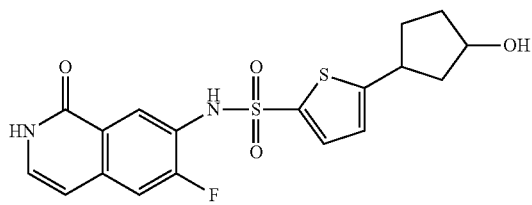 [SMILES: O=c1[nH]ccc2cc(F)c(NS(=O)(=O)c3ccc(C4CCC(O)C4)s3)cc12]

Add palladium hydroxide (20% on carbon, 0.83 g) to a reaction vessel and purge the vessel with nitrogen. Wet the catalyst with ethanol (25 mL) then add a solution of 5-(3-benzyloxycyclopentyl)-N-(6-fluoro-1-oxo-1,2-dihydroisoquinolin-7-yl)thiophene-2-sulfonamide (0.644 g, 1.29 mmol) in ethanol (25 mL) to the catalyst. Shake the reaction in a Parr shaker at room temperature under hydrogen atmosphere (30 psig) for 18 hours. Add more catalyst (0.844 g) and shake the reaction for 24 hours under hydrogen (30 psig). Add further catalyst (1.23 g) and shake the reaction for 24 hours under hydrogen (30 psig). Filter the suspension and concentrate under reduced pressure to give a clear oil. Purify the oil via reverse phase purification eluting with LC column: Waters Xbridge $C_{18}$ 30×75 mm 5 m; A=10 mM $NH_4HCO_3$ in 5% MeOH/$H_2O$, B=ACN Compound Gradient: 6% B isocratic for 4 min, 6-13.4% B in 3 min, 13.4-30% B in 1 min; Column temp: ambient; Flow rate: 85 mL/min. Isolate the first eluting peak as Example 42 (40 mg, 7.6%, $R_t$=6.63 min) LC/MS (m/z): 409 (M+H). Isolate the second eluting peak as Example 43, (120 mg, 22.9%, $R_t$=7.30 min). LC/MS (m/z): 409 (M+H).

Alternate Preparation Example 42

Alternate Preparation, Example 43

Add boron tribromide (1 M in heptanes, 40 mL) drop wise to an 0° C. solution of 5-(3-benzyloxycyclopentyl)-N-(6-fluoro-1-oxo-1,2-dihydroisoquinolin-7-yl)thiophene-2-sulfonamide (20 g, 40.1 mmol) in DCM (600 mL). Stir the reaction at room temperature until LC/MS (sample in MeOH) shows starting material is consumed (~3 h) Cool the reaction to 0° C. and quench the reaction drop wise with MeOH (200 mL). Concentrate the reaction under reduced pressure to a thick red oil. Purify the oil via reverse phase purification eluting with 4% (0.1% formic acid in ACN)/96% (0.1% formic acid in water) for 5 minutes, then increase ACN amounts from 4-55% ACN during 30 minutes; to give the first eluting peak as racemic trans isomers (1.85 g, 11.3%) LC/MS (m/z): 409 (M+H) and the second eluting peak as racemic cis isomers (2.39 g, 14.6%), LC/MS (m/z): 409 (M+H)).

The following compounds are prepared essentially by the procedures of Alternate Preparation Examples 42 and 43.

TABLE 9

| Ex. No. | Chemical Name | Structure | ES/MS (m/z) (M + 1) |
|---|---|---|---|
| 44* | racemic trans 5(3,3-Difluoro-4-hydroxycyclopentyl)-N-(6-fluoro-1-oxo-1,2-dihydroisoquinolin-7-yl)thiophene-2-sulfonamide | 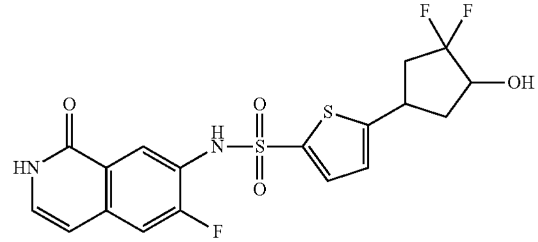 [SMILES: O=c1[nH]ccc2cc(F)c(NS(=O)(=O)c3ccc(C4CC(O)C(F)(F)C4)s3)cc12] | 445 |

TABLE 9-continued

| Ex. No. | Chemical Name | Structure | ES/MS (m/z) (M + 1) |
|---|---|---|---|
| 45* | racemic cis 5(3,3-Difluoro-4-hydroxycyclopentyl)-N-(6-fluoro-1-oxo-1,2-dihydroisoquinolin-7-yl)thiophene-2-sulfonamide | 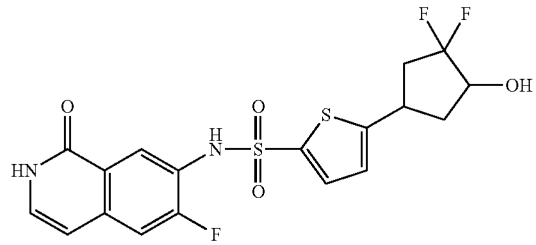 [SMILES: O=c1[nH]ccc2cc(F)c(NS(=O)(=O)c3ccc(C4CC(O)C(F)(F)C4)s3)cc12] | 445 |

*Purify the oil via reverse phase chromatography eluting with 10 mM ammonium bicarbonate solution 5% isocratic for 10 minutes, then 5-30% ACN for 28 min and 30% ACN for 13 minutes to give the first eluting peak as Example 44 and the second eluting peak as Example 45.

Example 46

N-(6-Fluoro-1-oxo-1,2-dihydroisoquinolin-7-yl)-5-[(1R,3R)-3-hydroxycyclopentyl]thiophene-2-sulfonamide

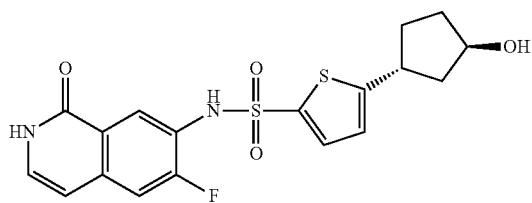 [SMILES: O=c1[nH]ccc2cc(F)c(NS(=O)(=O)c3ccc([C@@H]4CC[C@@H](O)C4)s3)cc12]

Example 47

N-(6-Fluoro-1-oxo-1,2-dihydroisoquinolin-7-yl)-5-[(1S,3S)-3-hydroxycyclopentyl]thiophene-2-sulfonamide

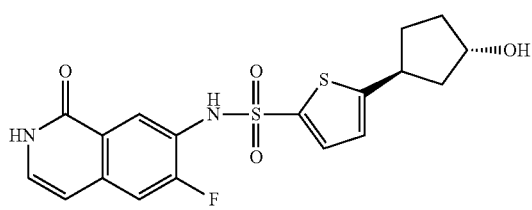 [SMILES: O=c1[nH]ccc2cc(F)c(NS(=O)(=O)c3ccc([C@H]4CC[C@H](O)C4)s3)cc12]

Resolve enantiomers from the racemic mixture as described in Examples 33 and 34 using the following parameters: Column: Chiralpak AD-H, 21×250 mm; Detection: 225 nm; Mobile Phase: 35% MeOH/65% CO₂; Column BPR Set Point: 10³ kPa; Obtain the first eluting peak as title compound Example 46 (14 mg, 35%, R_f=2.45 min; 99% ee), ES/MS (m/z): 409 (M+H). Obtain the second eluting peak as title compound Example 47 (14 mg, 35%, R_f=2.81 min; 95.9% ee), ES/MS (m/z): 409 (M+H).

Example 48 cis N-(6-Fluoro-1-oxo-1,2-dihydroisoquinolin-7-yl)-5-(3-hydroxycyclopentyl)thiophene-2-sulfonamide Isomer 1

Example 49 cis N-(6-Fluoro-1-oxo-1,2-dihydroisoquinolin-7-yl)-5-(3-hydroxycyclopentyl)thiophene-2-sulfonamide Isomer 2

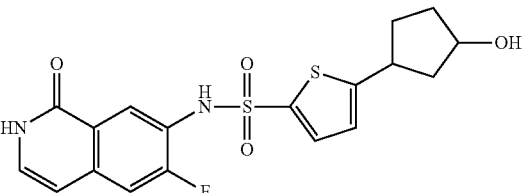

Resolve enantiomers from the racemic mixture as described in Examples 32 and 33 using the following parameters: No isopropylamine is used in dissolution, Column: Chiralpak AD-H, 21×250 mm; Detection: 225 nm; Mobile Phase: 35% MeOH/65% CO₂; BPR Set Point: 10³ kPa; BPR. Obtain the first eluting peak as Example 48, isomer 1 (45 mg, 38%, R_f=2.22 min; 99.2% ee), ES/MS (m/z): 409 (M+H). Obtain the second eluting peak as Example 49, isomer 2 (40 mg, 33%, R_f=2.61 min; 97.6% ee), ES/MS (m/z): 409 (M+H).

Example 50 trans 5-(3,3-Difluoro-4-hydroxycyclopentyl)-N-(6-fluoro-1-oxo-1,2-dihydroisoquinolin-7-yl)thiophene-2-sulfonamide, Isomer 1

Example 51 trans 5-(3,3-Difluoro-4-hydroxycyclopentyl)-N-(6-fluoro-1-oxo-1,2-dihydroisoquinolin-7-yl)thiophene-2-sulfonamide, Isomer 2

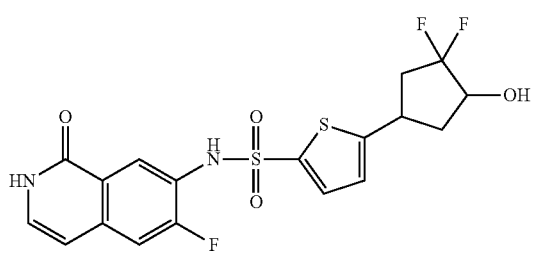

Resolve enantiomers from the racemic mixture as described in Examples 33 and 34 using the following parameters: No isopropylamine is used in dissolution, Column: Chiralpak AD-H, 20×150 mm; Detection: 225 nm; Mobile Phase: 35% IPA/65% $CO_2$; BPR Set Point: $10^3$ kPa; Obtain the first eluting peak as Example 50, Isomer 1 (32 mg, 30%, $R_t$=2.06 min; 99% ee), ES/MS (m/z): 445 (M+H). Obtain the second eluting peak as Example 51, Isomer 2 (44 mg, 41%, $R_t$=2.42 min; 98.7% ee), ES/MS (m/z): 445 (M+H).

Example 52 cis, 5-(3,3-Difluoro-4-hydroxycyclopentyl)-N-(6-fluoro-1-oxo-1,2-dihydroisoquinolin-7-yl)thiophene-2-sulfonamide, Isomer 1

Example 53 cis, 5-(3,3-Difluoro-4-hydroxycyclopentyl)-N-(6-fluoro-1-oxo-1,2-dihydroisoquinolin-7-yl)thiophene-2-sulfonamide, Isomer 2

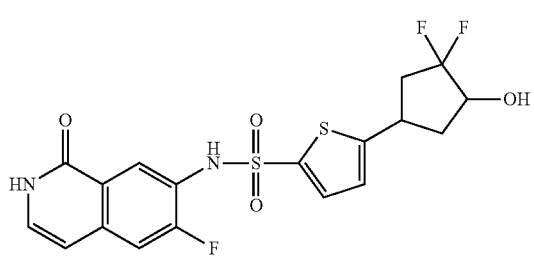

Resolve enantiomers from the racemic mixture as described in Examples 33 and 34 using the following parameters: Column: Chiralpak AD-H, 21×250 mm; Detection: 225 nm; Mobile Phase: 35% IPA/65% $CO_2$. Obtain the first eluting peak as Example 52, Isomer 1 (119 mg, 40%, $R_t$=2.23 min; 99% ee), ES/MS (m/z): 445 (M+H). Obtain the second eluting peak as Example 53, Isomer 2 (119 mg, 40%, $R_t$=2.80 min, 97.6% ee), ES/MS (m/z): 445 (M+H).

Example 54 racemic 5-(4,4-Difluoro-3-hydroxypiperidin-1-yl)-N-(6-fluoro-1-oxo-1,2-dihydroisoquinolin-7-yl)thiophene-2-sulfonamide

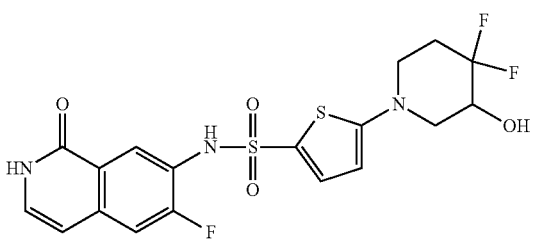 [SMILES: O=c1[nH]ccc2cc(F)c(NS(=O)(=O)c3ccc(N4CCC(F)(F)C(O)C4)s3)cc12]

Add racemic 4,4-difluoropiperidin-3-ol (1.0 g, 7.4 mmol) to a solution of 5-fluoro-N-(6-fluoro-1-oxo-1,2-dihydroisoquinolin-7-yl)thiophene-2-sulfonamide (1.4 g, 4.1 mmol) in pyridine (10 mL). Heat to 100° C. for 20 hours and cool to ambient temperature. Dilute the mixture with water and acidify with concentrated aqueous HCl. Extract with EtOAc. Combine the organic extracts and wash with water, dry over magnesium sulfate, filter, and concentrate under reduced pressure to give a residue. Purify the residue by silica gel flash chromatography eluting with a gradient of 10-45% ACN with 0.1% TFA:$H_2O$ with 0.1% TFA over 20 minutes then hold at 45% for 10 minutes. Subsequently purify by silica gel flash chromatography, eluting with MeOH: DCM (4:6) to give the title compound (0.75 g, 40%). ES/MS (m/z): 460 (M+H).

The following compounds are prepared essentially by the method of Example 54.

TABLE 10

| Ex. No. | Chemical Name | Structure | ES/MS (m/z) (M + 1) |
|---|---|---|---|
| 55 | racemic, trans-5-(4-Fluoro-3-hydroxypiperidin-1-yl)-N-(6-fluoro-1-oxo-1,2-dihydroisoquinolin-7-yl)thiophene-2-sulfonamide | 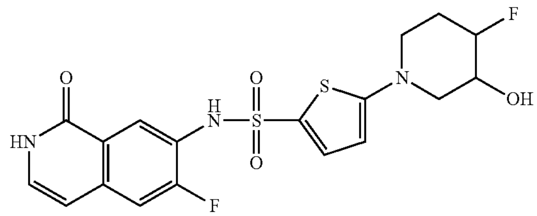 [SMILES: O=c1[nH]ccc2cc(F)c(NS(=O)(=O)c3ccc(N4CCC(F)C(O)C4)s3)cc12] | 442 |
| 56 | racemic 5-(3,3-Difluoro-4-hydroxypiperidin-1-yl)-n-(6-fluoro-1-oxo-1,2-dihydroisoquinolin-7-yl)thiophene-2-sulfonamide | 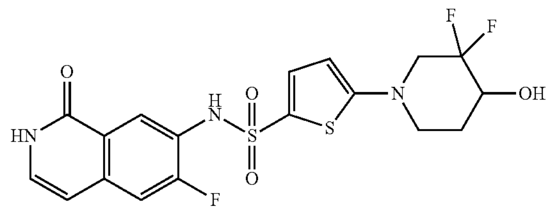 [SMILES: O=c1[nH]ccc2cc(F)c(NS(=O)(=O)c3ccc(N4CCC(O)C(F)(F)C4)s3)cc12] | 460 |

Example 57 racemic, cis-5-(4-Fluoro-3-hydroxypiperidin-1-yl)-N-(6-fluoro-1-oxo-1,2-dihydroisoquinolin-7-yl)thiophene-2-sulfonamide

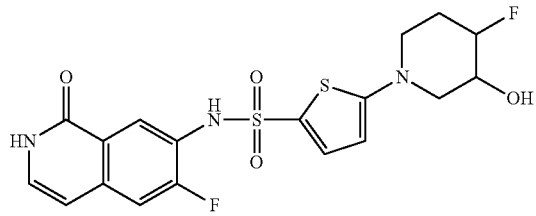 [SMILES: O=c1[nH]ccc2cc(F)c(NS(=O)(=O)c3ccc(N4CCC(F)C(O)C4)s3)cc12]

Dissolve racemic, cis-4-fluoropiperidin-3-ol hydrochloride (1.6 g, 10 mmol) in MeOH, load onto an SCX column and elute with 7 N NH$_3$/MeOH and concentrate to give racemic, cis-4-fluoropiperidin-3-ol (1.2 g, 10 mmol). Add racemic, cis-4-fluoropiperidin-3-ol (0.84 g, 7.0 mmol) to a solution of 5-fluoro-N-(6-fluoro-1-oxo-1,2-dihydroisoquinolin-7-yl)thiophene-2-sulfonamide (1.2 g, 3.5 mmol) in pyridine (10 mL). Heat mixture at 100° C. for 16 hours and concentrate under reduced pressure. Dissolve the residue in EtOAc, acidify with concentrated aqueous HCl and extract with EtOAc. Wash the combined organic layers with water and brine, dry over magnesium sulfate, filter, and concentrate to give a residue. Purify the residue by silica gel flash chromatography, eluting with 10% MeOH/DCM to give the title compound (1.0 g, 65%). ES/MS (m/z): 442 (M+H).

Example 58

5-[(3 S)-(4,4-Difluoro-3-hydroxypiperidin-1-yl)]-N-(6-fluoro-1-oxo-1,2-dihydroisoquinolin-7-yl)thiophene-2-sulfonamide

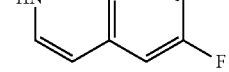

Example 59

5-[(3R)-(4,4-Difluoro-3-hydroxypiperidin-1-yl)]-N-(6-fluoro-1-oxo-1,2-dihydroisoquinolin-7-yl)thiophene-2-sulfonamide

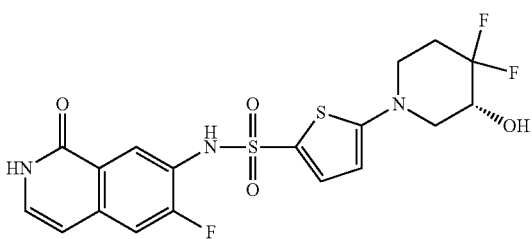 [SMILES: O=c1[nH]ccc2cc(F)c(NS(=O)(=O)c3ccc(N4CCC(F)(F)[C@H](O)C4)s3)cc12]

Resolve enantiomers from the racemic mixture as described in Examples 32 and 33 using the following parameters: No isopropylamine is used in dissolution, Column: Chiralpak AD-H, 150×20 mm; Detection: 225 nm; Mobile Phase: 40% IPA/CO$_2$; Column Temperature: 40° C.; BPR Set Point: 10$^3$ kPa; BPR Temperature: 35° C. Obtain the first eluting peak as Example 58 (0.35 g, 42%, R$_t$=2.39 min, 98% ee), ES/MS (m/z): 460 (M+H). Obtain the second eluting peak as Example 59 (0.34 g, 38%, R$_t$=2.92 min. 98.8% ee), ES/MS (m/z): 460 (M+H).

Example 60 trans-5-(4-Fluoro-3-hydroxypiperidin-1-yl)-N-(6-fluoro-1-oxo-1,2-dihydroisoquinolin-7-yl)thiophene-2-sulfonamide, Isomer 1

Example 61 trans-5-(4-Fluoro-3-hydroxypiperidin-1-yl)-N-(6-fluoro-1-oxo-1,2-dihydroisoquinolin-7-yl)thiophene-2-sulfonamide, Isomer 2

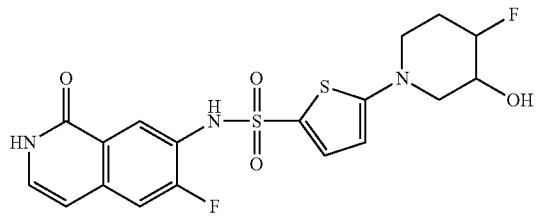 [SMILES: O=c1[nH]ccc2cc(F)c(NS(=O)(=O)c3ccc(N4CCC(F)C(O)C4)s3)cc12]

Resolve enantiomers from the racemic mixture as described in Examples 32 and 33 using the following parameters: Column: Chiralpak AD-H, 21×250 mm; Detection: 225 nm; Mobile Phase: 40% IPA/CO$_2$; BPR Set Point: 10$^3$ kPa. Obtain the first eluting peak as Example 60, Isomer 1 (0.26 g, 32%, R$_t$=2.57 min, 99% ee), ES/MS (m/z): 442 (M+H). Obtain the second eluting peak as Example 61, Isomer 2 (0.31 g, 39%, R$_t$=3.17 min, 97% ee), ES/MS (m/z): 442 (M+H).

Example 62 cis-5-(4-Fluoro-3-hydroxypiperidin-1-yl)-N-(6-fluoro-1-oxo-1,2-dihydroisoquinolin-7-yl)thiophene-2-sulfonamide, Isomer 1

Example 63 cis-5-(4-Fluoro-3-hydroxypiperidin-1-yl)-N-(6-fluoro-1-oxo-1,2-dihydroisoquinolin-7-yl)thiophene-2-sulfonamide, Isomer 2

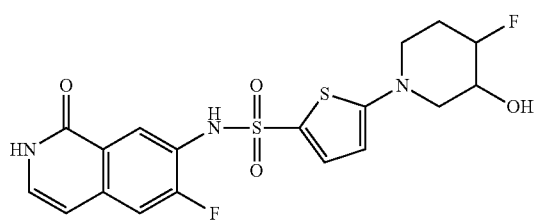 [SMILES: O=c1[nH]ccc2cc(F)c(NS(=O)(=O)c3ccc(N4CCC(F)C(O)C4)s3)cc12]

Resolve enantiomers from the racemic mixture as described in Examples 33 and 34 using the following parameters: Dissolve in MeOH, Column: Chiralpak AD-H, 5×150 mm; Detection: 300 nm; Mobile Phase: 35% EtOH/CO$_2$; Column Temperature: 40° C.; BPR Set Point: 10$^3$ kPa. Obtain the first eluting peak as Example 62, isomer 1 (0.44 g, 45%, R$_t$=4.52 min, >98% ee), ES/MS (m/z): 442 (M+H). Obtain the second eluting peak as Example 63, isomer 2 (0.44 g, 46%, R$_t$=5.29 min, >94% ee), ES/MS (m/z): 442

Example 64 racemic, 5-[3,4-Dihydroxy-4-(trifluoromethyl)piperidin-1-yl]-N-(6-fluoro-1-oxo-1,2-dihydroisoquinolin-7-yl)thiophene-2-sulfonamide, Diastereomer 1

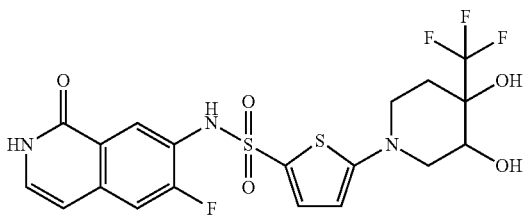 [SMILES: O=c1[nH]ccc2cc(F)c(NS(=O)(=O)c3ccc(N4CCC(O)(C(F)(F)F)C(O)C4)s3)cc12]

Combine potassium carbonate (298.6 mg, 2.16 mmol) with 4-(trifluoromethyl)piperidine-3,4-diol, Diastereomer 1 (0.2 g, 1.08 mmol) and DMSO (12 mL). Add copper(I) bromide (61.98 mg, 0.43 mmol) hydroxyproline (120.4 mg, 0.43 mmol) and 5-bromo-N-(6-fluoro-1-oxo-1,2-dihydroisoquinolin-7-yl)thiophene-2-sulfonamide (435 mg, 1.08 mmol). Replace the atmosphere with N$_2$ and heat at 100° C. for 16 hours. Remove most of the DMSO by distillation using high vacuum. Add saturated aqueous NH$_4$Cl (0.25 mL) and dilute with MeOH (20 mL). Filter and concentrate to an oil. Purify the residue by low-pH reverse phase HPLC using a C18 AXIA packed 30×75 mm column, with mobile phase A: 0.10% TFA in water, and mobile phase B: 0.10% TFA in ACN. Elute with 5% to 42% B in A to give the title compound (187 mg, 34%). ES/MS (m/z): 508 (M+H).

The following compound is prepared essentially by the method of Example 64.

TABLE 11

| Ex. No. | Chemical Name | Structure | ES/MS (m/z) (M + 1) |
|---|---|---|---|
| 65* | racemic 5-[3,4-Dihydroxy-4-(trifluoromethyl)piperidin-1-yl]-N-(6-fluoro-1-oxo-1,2-dihydroisoquinolin-7-yl)thiophene-2-sulfonamide, Diastereomer 2 | 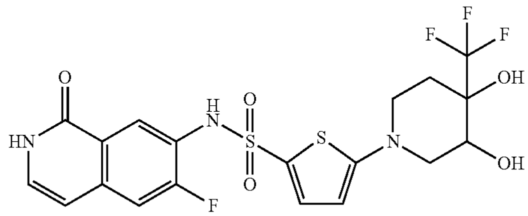 [SMILES: O=c1[nH]ccc2cc(F)c(NS(=O)(=O)c3ccc(N4CCC(O)(C(F)(F)F)C(O)C4)s3)cc12] | 508 |

*Material is further purified by silica gel chromatography eluting with 90/10 CHCl₃/MeOH.

Example 66

5-[3,4-Dihydroxy-4-(trifluoromethyl)piperidin-1-yl]-N-(6-fluoro-1-oxo-1,2-dihydroisoquinolin-7-yl)thiophene-2-sulfonamide, Isomer 1

Example 67

5-[3,4-Dihydroxy-4-(trifluoromethyl)piperidin-1-yl]-N-(6-fluoro-1-oxo-1,2-dihydroisoquinolin-7-yl)thiophene-2-sulfonamide, Isomer 2

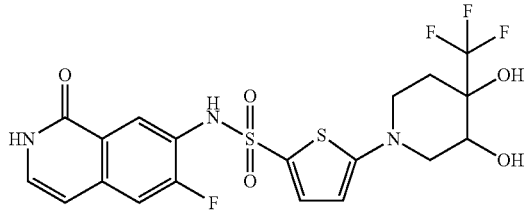 [SMILES: O=c1[nH]ccc2cc(F)c(NS(=O)(=O)c3ccc(N4CCC(O)(C(F)(F)F)C(O)C4)s3)cc12]

Separate the two enantiomers from racemic, 5-[3,4-dihydroxy-4-(trifluoromethyl)piperidin-1-yl]-N-(6-fluoro-1-oxo-1,2-dihydroisoquinolin-7-yl)thiophene-2-sulfonamide, Diastereomer 1 using the chromatography chiral procedure as described in Examples 33 and 34 using the following parameters: Chiralpak AD-H, 20×150 mm column. Collect the first eluting peak to give Example 66, Isomer 1 (47 mg, 26%, >99% ee) ES/MS (m/z): 508 (M+H) and Example 67, Isomer 2 (49 mg, 27%, >99% ee) ES/MS (m/z): 508 (M+H).

Example 68

5-[3,4-Dihydroxy-4-(trifluoromethyl)piperidin-1-yl]-N-(6-fluoro-1-oxo-1,2-dihydroisoquinolin-7-yl)thiophene-2-sulfonamide, Isomer 1

Example 69

5-[3,4-Dihydroxy-4-(trifluoromethyl)piperidin-1-yl]-N-(6-fluoro-1-oxo-1,2-dihydroisoquinolin-7-yl)thiophene-2-sulfonamide, Isomer 2

Separate the two enantiomers from racemic 5-[-3,4-dihydroxy-4-(trifluoromethyl)-1-piperidyl]-N-(6-fluoro-1-oxo-1,2-dihydroisoquinolin-7-yl)thiophene-2-sulfonamide Diastereomer 2 (23 mg) by chiral chromatography using Chiralpak AD-H, 20×150 mm column, eluting with 40% MeOH/CO₂, at flow rate of 70 mL/min, to give Example 68, Isomer 1 (8.8 mg, 38%, >99% ee) ES/MS (m/z): 508 (M+H) and Example 69, Isomer 2 (9.3 mg, 40%, >99% ee) ES/MS (m/z): 508 (M+H).

Example 70

Cis, meso, 5-(4,4-Difluoro-3,5-dihydroxypiperidin-1-yl)-N-(6-fluoro-1-oxo-1,2-dihydroisoquinolin-7-yl)thiophene-2-sulfonamide, Diastereomer 1

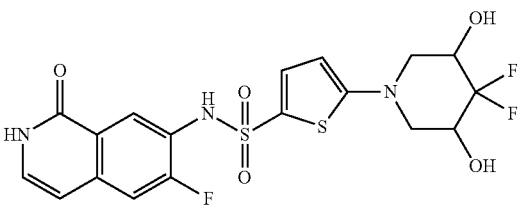 [SMILES: O=c1[nH]ccc2cc(F)c(NS(=O)(=O)c3ccc(N4CC(O)C(F)(F)C(O)C4)s3)cc12]

Example 71 racemic, trans, 5-(4,4-Difluoro-3,5-dihydroxypiperidin-1-yl)-N-(6-fluoro-1-oxo-1,2-dihydroisoquinolin-7-yl)thiophene-2-sulfonamide, Diastereomer 2

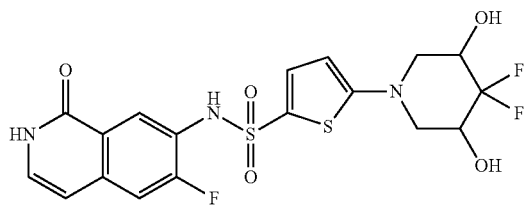

Add DCM (3 mL) and TFA (3 mL) to a 3:1 mixture of cis, meso-tert-butyl 4,4-difluoro-3,5-dihydroxy-piperidine-1-carboxylate and racemic, trans-tert-butyl 4,4-difluoro-3,5-dihydroxy-piperidine-1-carboxylate (0.42 g, 1.66 mmol). After 2 hours, remove the solvents under reduced pressure. Add 5-fluoro-N-(6-fluoro-1-oxo-1,2-dihydroisoquinolin-7-yl)thiophene-2-sulfonamide (0.15 g, 0.44 mmol), DIPEA (3 mL) and pyridine (6 mL). Heat the mixture at 100° C. for 24 hours and cool to ambient temperature. Remove the solvents under reduced pressure. Load onto an SCX column. Elute with MeOH and concentrate the filtrate. Separate the two diastereomers by high-pH reverse phase HPLC using a C18 OBD 30×75 mm column, with mobile phase A: 10 mM aqueous ammonium bicarbonate solution with 5% MeOH, mobile phase B: ACN. Elute with 2% to 12% B in A, flow rate 85 mL/minutes, to give Example 70, Diastereomer 1, (40 mg, 19%), ES/MS (m/z): 476 (M+H); and Example 71, Diastereomer 2, (20 mg, 10%), ES/MS (m/z): 476 (M+H).

Example 72

5-(3,3-Difluoro-4-hydroxypiperidin-1-yl)-n-(6-fluoro-1-oxo-1,2-dihydroisoquinolin-7-yl)thiophene-2-sulfonamide, Isomer 1

Example 73

5-(3,3-Difluoro-4-hydroxypiperidin-1-yl)-n-(6-fluoro-1-oxo-1,2-dihydroisoquinolin-7-yl)thiophene-2-sulfonamide, Isomer 2

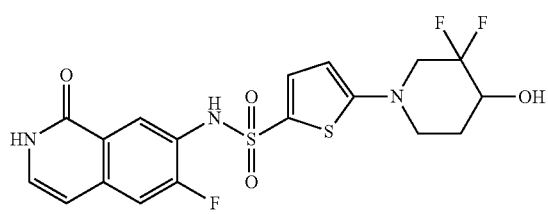 [SMILES: O=c1[nH]ccc2cc(F)c(NS(=O)(=O)c3ccc(N4CCC(O)C(F)(F)C4)s3)cc12]

Resolve enantiomers from the racemic mixture as described in Example 66 and 67 to give Example 72, Isomer 1 (40 mg, 27%, >99% ee), ES/MS (m/z): 460 (M+H); and Example 73, Isomer 2 (40 mg, 27%, >99% ee), ES/MS (m/z): 460 (M+H).

Example 74 racemic, trans 5-(3-Fluoro-4-hydroxypiperidin-1-yl)-N-(6-fluoro-1-oxo-1,2-dihydroisoquinolin-7-yl)thiophene-2-sulfonamide

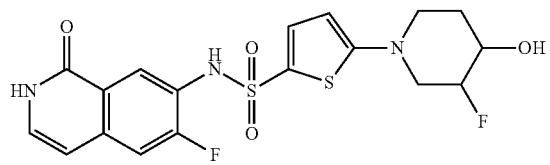 [SMILES: O=c1[nH]ccc2cc(F)c(NS(=O)(=O)c3ccc(N4CCC(O)C(F)C4)s3)cc12]

Add TFA (3 mL) to a solution of racemic, trans-tert-butyl 3-fluoro-4-hydroxypiperidine-1-carboxylate (288 mg, 1.31 mmol) in DCM (3 mL). After 2 hours, remove the solvents under reduced pressure. Add 5-fluoro-N-(6-fluoro-1-oxo-1,2-dihydroisoquinolin-7-yl)thiophene-2-sulfonamide (180 mg, 0.53 mmol) and pyridine (5 mL). Add DIPEA (0.50 mL, 2.87 mmol). Heat the mixture at 100° C. for 18 hours and cool to ambient temperature. Remove the solvents under reduced pressure. Dissolve the residue in 4:1 DCM/IPA, extract with 1 N aqueous HCl solution and brine, dry over sodium sulfate, filter, and concentrate under reduced pressure. Purify the residue by silica gel flash chromatography, eluting with 0 to 10% MeOH/DCM to give the title compound (145 mg, 62%). ES/MS (m/z): 442 (M+H).

The following compound is prepared essentially by the method of Example 74.

TABLE 12

| Ex. No. | Chemical Name | Structure | ES/MS (m/z) (M + 1) |
|---|---|---|---|
| 75 | racemic, cis 5-(3-fluoro-4-hydroxypiperidin-1-yl)-N-(6-fluoro-1-oxo-1,2-dihydroisoquinolin-7-yl)thiophene-2-sulfonamide | 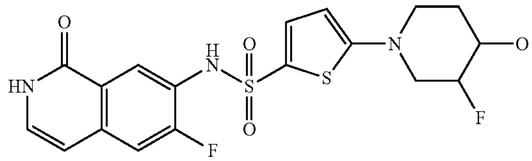 [SMILES: O=c1[nH]ccc2cc(F)c(NS(=O)(=O)c3ccc(N4CCC(O)C(F)C4)s3)cc12] | 442 |

Example 76 trans 5-(3-Fluoro-4-hydroxypiperidin-1-yl)-N-(6-fluoro-1-oxo-1,2-dihydroisoquinolin-7-yl)thiophene-2-sulfonamide, Isomer 1

Example 77 trans 5-(3-Fluoro-4-hydroxypiperidin-1-yl)-N-(6-fluoro-1-oxo-1,2-dihydroisoquinolin-7-yl)thiophene-2-sulfonamide, Isomer 2

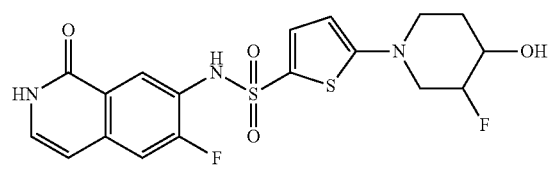 [SMILES: O=c1[nH]ccc2cc(F)c(NS(=O)(=O)c3ccc(N4CCC(O)C(F)C4)s3)cc12]

Separate the two enantiomers from racemic, trans 5-(3-fluoro-4-hydroxypiperidin-1-yl)-N-(6-fluoro-1-oxo-1,2-dihydroisoquinolin-7-yl)thiophene-2-sulfonamide as described in Example 66 and 67 to give Example 76, Isomer 1 (50 mg, 22%, 99.4% ee), ES/MA (m/z): 442 (M+H); and Example 77, Isomer 2 (50 mg, 22%, 98.9% ee), ES/MS (m/z): 442 (M+H).

Example 78 cis 5-(3-Fluoro-4-hydroxypiperidin-1-yl)-N-(6-fluoro-1-oxo-1,2-dihydroisoquinolin-7-yl)thiophene-2-sulfonamide, Isomer 1

Example 79 cis 5-(3-Fluoro-4-hydroxypiperidin-1-yl)-N-(6-fluoro-1-oxo-1,2-dihydroisoquinolin-7-yl)thiophene-2-sulfonamide, Isomer 2

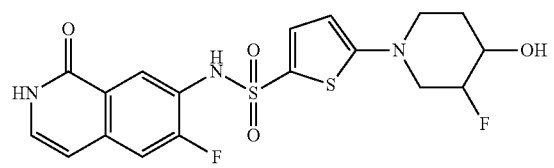 [SMILES: O=c1[nH]ccc2cc(F)c(NS(=O)(=O)c3ccc(N4CCC(O)C(F)C4)s3)cc12]

Separate the two enantiomers from racemic, cis 5-(3-fluoro-4-hydroxypiperidin-1-yl)-N-(6-fluoro-1-oxo-1,2-dihydroisoquinolin-7-yl)thiophene-2-sulfonamide (175 mg, 0.40 mmol) by chiral chromatography using Chiralpak OJ-H, 21×250 mm column, eluting with 25% MeOH/CO$_2$, at flow rate of 70 g/min, to give Example 78, Isomer 1 (30 mg, 17%, 97.5% ee), ES/MS (m/z): 442 (M+H); and Example 79, Isomer 2 (50 mg, 29%, 99.3% ee), ES/MS(m/z): 442 (M+H).

Example 80

N-(6-Fluoro-1-oxo-1,2-dihydroisoquinolin-7-yl)-5-(6-oxo-1,4,5,6-tetrahydropyridin-3-yl)thiophene-2-sulfonamide

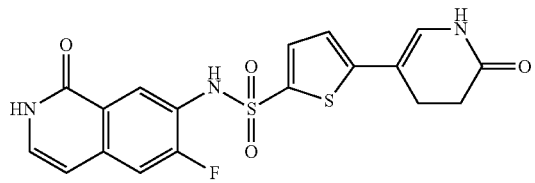 [SMILES: O=C1CCC(c2ccc(S(=O)(=O)Nc3cc4c(=O)[nH]ccc4cc3F)s2)=CN1]

Heat a mixture of 5-bromo-N-(1-oxo-1,2-dihydroisoquinolin-7-yl)thiophene-2-sulfonamide (1.00 g, 2.48 mmol), tert-butyl 2-oxo-5-(4,4,5,5-tetramethyl-1,3,2-dioxaborolan-2-yl)-3,4-dihydropyridine-1(2H)-carboxylate (1.12 g, 3.47 mmol), tetrakis(triphenyl-phosphine)palladium(0) (148 mg, 0.124 mmol) in dioxane (40 mL) and water (10 mL) to 100° C. After 24 hours, cool the reaction mixture to ambient temperature. Remove the solvents under reduced pressure. Dissolve the residue in 4:1 DCM/IPA, extract with 1 N aqueous HCl solution and brine, dry over sodium sulfate, filter, and concentrate under reduced pressure to give a residue. Purify by reverse phase chromatography, mobile phase A: 0.1% TFA in water, mobile phase B: 0.1% TFA in ACN. Elute with 10 to 50% B in A. Further purify by silica gel flash chromatography, eluting with 0 to 10% MeOH/DCM, to give the title compound (180 mg, 17%). ES/MS (m/z): 420 (M+H).

Example 81

5-(5,5-Dimethyl-6-oxo-1,4,5,6-tetrahydropyridin-3-yl)-N-(6-fluoro-1-oxo-1,2-dihydroisoquinolin-7-yl)thiophene-2-sulfonamide

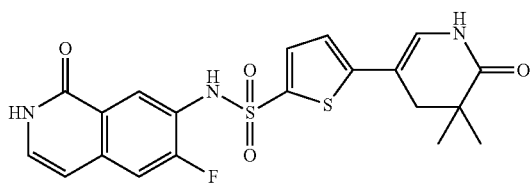 [SMILES: CC1(C)CC(c2ccc(S(=O)(=O)Nc3cc4c(=O)[nH]ccc4cc3F)s2)=CNC1=O]

Add chlorosulfuric acid (0.430 mL, 6.51 mmol) to an ice cooled solution of 3,3-dimethyl-5-(thiophen-2-yl)-3,4-dihydropyridin-2(1H)-one (450 mg, 2.17 mmol) in DCM (60 mL) at 0° C. After 15 minutes, remove the cooling bath and allow the reaction mixture to warm up to ambient temperature. After 1.5 hour, pour the reaction mixture to ice cooled brine. Extract with DCM (4×). Combine the organic extracts, dry over magnesium sulfate, filter, and concentrate under reduced pressure to give a residue. Cool the residue in an ice bath at 0° C. Add 7-amino-6-fluoro-1,2-dihydroisoquinolin-1-one (194 mg, 1.09 mmol) and pyridine (5 mL). Remove the cooling bath after addition and allow the reaction mixture to warm up to ambient temperature. After 16 hours, add 5 N aqueous HCl solution to pH=1. Extract with EtOAc. Combine the organic extracts and wash with 1 N aqueous HCl solution and brine. Dry over sodium sulfate, filter, and concentrate under reduced pressure to give a residue. Purify the residue by silica gel flash chromatography, eluting with 0 to 10% MeOH/DCM to give the title compound (280 mg, 57%). ES/MS (m/z): 448 (M+H).

Example 82

5-(5,5-Dimethyl-6-oxo-1,4,5,6-tetrahydropyridazin-3-yl)-N-(6-fluoro-1-oxo-1,2-dihydroisoquinolin-7-yl)thiophene-2-sulfonamide

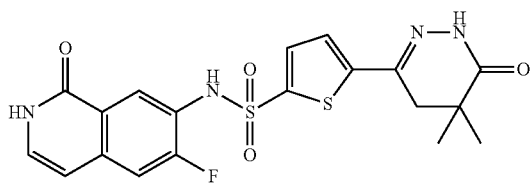

Add phosphorus pentachloride (200 mg, 0.96 mmol) to ice cooled chlorosulfuric acid (0.16 mL, 2.4 mmol) at 0° C. After 15 min, add 5,5-dimethyl-3-(2-thienyl)-1,4-dihydropyridazin-6-one (200 mg, 0.96 mmol). Remove the cooling bath and allow the reaction mixture to warm up to ambient temperature. After 4 hours, pour the reaction mixture to ice cooled brine. Extract with EtOAc. Combine organic layers, dry over magnesium sulfate, filter, and concentrate under reduced pressure to give a residue. Add 7-amino-6-fluoro-1,2-dihydroisoquinolin-1-one (137 mg, 0.77 mmol) and pyridine (5 mL) to the residue. After 17 hours, remove solvents under reduced pressure. Load onto SCX column. Elute with MeOH and concentrate the filtrate. Purify the residue by silica gel flash chromatography, eluting with 0 to 10% MeOH/DCM. Concentrate the fractions containing product under reduced pressure. Further purify by reverse phase chromatography, mobile phase A: 0.1% TFA in water, mobile phase B: 0.1% TFA in ACN. Elute with 10 to 45% B in A, to give the title compound (20 mg, 6%). ES/MS (m/z): 449 (M+H).

The following compound is prepared essentially by the method of Example 82.

TABLE 13

| Ex. No. | Chemical Name | Structure | ES/MS (m/z) (M + 1) |
|---|---|---|---|
| 83 | racemic 5-(5-Ethyl-5-methyl-6-oxo-1,4,5,6-tetrahydropyridin-3-yl)-N-(6-fluoro-1-oxo-1,2-dihydroisoquinolin-7-yl)thiophene-2-sulfonamide | 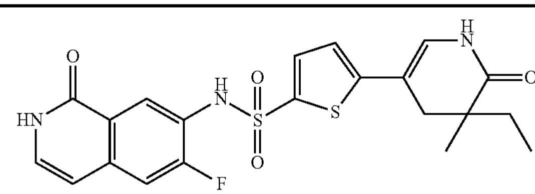 | 462 |

Alternate Preparation Example 82

Add portion wise 1,3-dichloro-5,5-dimethylhydantoin (17 g, 86 mmol) to a suspension of 6-[5-(benzylsulfanyl)thiophen-2-yl]-4,4-dimethyl-4,5-dihydropyridazin-3(2H)-one (19 g, 57 mmol) in ACN (290 mL), acetic acid (9.5 mL) and water (19 mL) at 0° C. keeping the internal temperature<25° C. during the addition. Add MTBE (200 mL) to the reaction mixture and filter the white solid, wash with MTBE, dry, and collect to give an intermediate compound, 5-(5,5-dimethyl-6-oxo-1,4-dihydropyridazin-3-yl)thiophene-2-sulfonyl chloride. Concentrate the filtrate to dryness, dissolve in DCM, and wash with aq. saturated NaHCO₃ until final pH of aqueous phase>5. Dry organic phase (MgSO₄), filter, and concentrate in vacuo to a yellow solid. Suspend both solids in MTBE and triturate. Filter the white solid, wash with MTBE, dry, and collect to give 5-(5,5-dimethyl-6-oxo-1,4-dihydropyridazin-3-yl)thiophene-2-sulfonyl chloride compound with 86% purity (13.1 g, 64%). ES/MS (m/z): 305 (M−H).

Add 5-(5,5-dimethyl-6-oxo-1,4-dihydropyridazin-3-yl)thiophene-2-sulfonyl chloride (13.1 g, 36.7 mmol) in portions at 0° C. to a solution of 7-amino-6-fluoro-1,2-dihydroisoquinolin-1-one (5.89 g, 33 mmol) in pyridine (79 mL). Stir at room temperature for 2.5 hours. Concentrate to dryness. Sonicate residue with DCM (100 mL) until an orange suspension forms. Filter the solid, wash with DCM and MTBE, dry, and to give the title compound (14 g, 80%). ES/MS (m/z): 449 (M+H).

Example 84

5-(5-Ethyl-5-methyl-6-oxo-1,4,5,6-tetrahydropyridin-3-yl)-N-(6-fluoro-1-oxo-1,2-dihydroisoquinolin-7-yl)thiophe2ne-2-sulfonamide, Isomer 1

Example 85

5-(5-Ethyl-5-methyl-6-oxo-1,4,5,6-tetrahydropyridin-3-yl)-N-(6-fluoro-1-oxo-1,2-dihydroisoquinolin-7-yl)thiophene-2-sulfonamide, Isomer 2

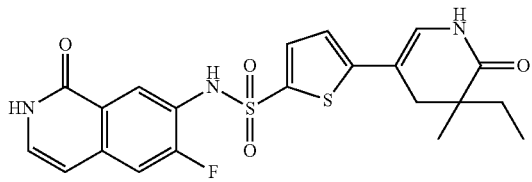 [SMILES: CCC1(C)CC(c2ccc(S(=O)(=O)Nc3cc4c(=O)[nH]ccc4cc3F)s2)=CNC1=O]

Separate the two enantiomers from racemic 5-(5-ethyl-5-methyl-6-oxo-1,4-dihydropyridin-3-yl)-N-(6-fluoro-1-oxo-1,2-dihydroisoquinolin-7-yl)thiophene-2-sulfonamide (190 mg, 0.412 mmol) by chiral chromatography using Chiralpak AD-H, 21.2×150 mm column, eluting with 40% MeOH/$CO_2$, at a flow rate of 70 g/min, to give Example 82, Isomer 1 (85 mg, 45%, >99% ee), ES/MS (m/z): 462 (M+H); and Example 83, Isomer 2 (85 mg, 45%, >99% ee), ES/MS (m/z): 462 (M+H).

Example 86 racemic N-(6-Fluoro-1-oxo-1,2-dihydroisoquinolin-7-yl)-5-(4-hydroxycyclopent-1-en-1-yl)thiophene-2-sulfonamide

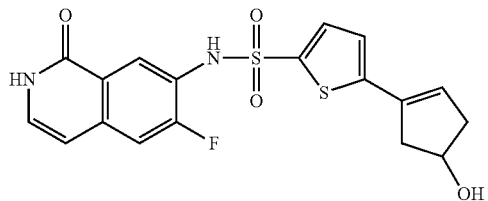 [SMILES: O=c1[nH]ccc2cc(F)c(NS(=O)(=O)c3ccc(C4=CCC(O)C4)s3)cc12]

Add tetra-n-butylammonium fluoride (1 M in THF, 8 mL) to 5-[4-[tert-butyl(dimethyl)silyl]oxycyclohexen-1-yl]-N-(6-fluoro-1-oxo-1,2-dihydroisoquinolin-7-yl)thiophene-2-sulfonamide (0.135 g, 0.252 mmol). Stir at room temperature for 1.5 hours. Add saturated ammonium chloride, then extract with EtOAc, dry over sodium sulfate, and concentrate under reduced pressure. Purify the crude material by silica gel chromatography eluting with DCM:MeOH (95:5) to give colorless grease. Add DCM to the oil and filter the resulting solid to give the title racemic compound (110 mg, 81%). ES/MS (m/z): 407.1 (M+H).

Example 87

N-(6-Fluoro-1-oxo-1,2-dihydroisoquinolin-7-yl)-5-(4-hydroxycyclopent-1-en-1-yl)thiophene-2-sulfonamide, Isomer 1

Example 88

N-(6-Fluoro-1-oxo-1,2-dihydroisoquinolin-7-yl)-5-(4-hydroxycyclopent-1-en-1-yl)thiophene-2-sulfonamide, Isomer 2

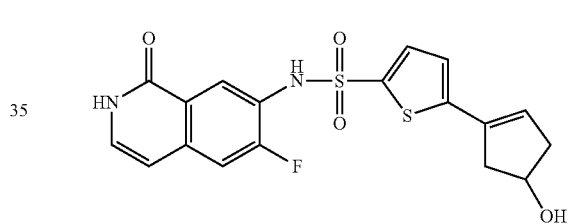

Separate racemic N-(6-fluoro-1-oxo-1,2-dihydroisoquinolin-7-yl)-5-(4-hydroxycyclopent-1-en-1-yl)thiophene-2-sulfonamide with chiral chromatography using Lux 5u Cellulose-2, 21×250 mm column eluting with 40% ethanol:60% $CO_2$ at a flow rate of 70 g/min, with detection at 225 nm to give Example 87, Isomer 1 (22 mg, 16.6%, >99% ee), ES/MS (m/z):407.1 (M+H) and Example 88, Isomer 2 (25 mg, 19%, >99% ee), ES/MS (m/z): 407.1 (M+H).

The following compounds are prepared essentially by the method of Examples 87 and 88.

TABLE 14

| Ex No. | Chemical Name | Structure | ES/MS (m/z) (M + 1) |
|---|---|---|---|
| 89 | racemic, N-(6-Fluoro-1-oxo-1,2-dihydroisoquinolin-7-yl)-5-(4-hydroxycyclohex-1-en-1-yl)thiophene-2-sulfonamide | 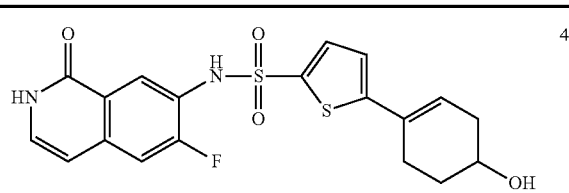 | 421.0 |

TABLE 14-continued

| Ex No. | Chemical Name | Structure | ES/MS (m/z) (M + 1) |
|---|---|---|---|
| 90 | N-(6-Fluoro-1-oxo-1,2-dihydroisoquinolin-7-yl)-5-(4-hydroxycyclohex-1-en-1-yl)thiophene-2-sulfonamide, Isomer 2 | 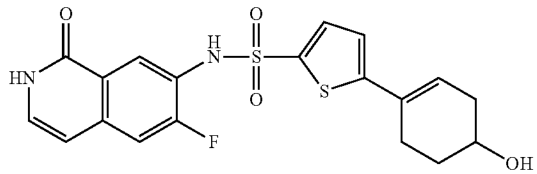 [SMILES: O=c1[nH]ccc2cc(F)c(NS(=O)(=O)c3ccc(C4=CCC(O)CC4)s3)cc12] | 421.0 |
| 91 | N-(6-Fluoro-1-oxo-1,2-dihydroisoquinolin-7-yl)-5-(4-hydroxycyclohex-1-en-1-yl)thiophene-2-sulfonamide, Isomer 1 | 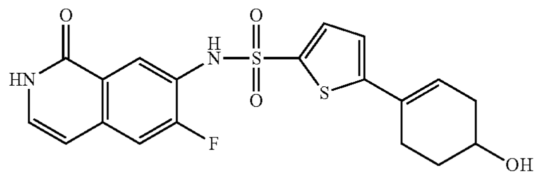 [SMILES: O=c1[nH]ccc2cc(F)c(NS(=O)(=O)c3ccc(C4=CCC(O)CC4)s3)cc12] | 421.0 |

Cancer is increasingly recognized as a heterogeneous collection of diseases whose initiation and progression are induced by the aberrant function of one or more genes that regulate DNA repair, genome stability, cell proliferation, cell death, adhesion, angiogenesis, invasion, and metastasis in cell and tissue microenviroments. Variant or aberrant function of the "cancer" genes may result from naturally occurring DNA polymorphism, changes in genome copy number (through amplification, deletion, chromosome loss, or duplication), changes in gene and chromosome structure (through chromosomal translocation, inversion, or other rearrangement that leads to deregulated gene expression), and point mutations. Cancerous neoplasms may be induced by one aberrant gene function, and maintained by the same aberrant gene function, or maintenance and progression exacerbated by additional aberrant gene functions.

Beyond the genetic chromosomal aberrations mentioned above, each of the cancers may also include epigenetic modifications of the genome including DNA methylation, genomic imprinting, and histone modification by acetylation, methylation, or phosphorylation. An epigenetic modification may play a role in the induction and/or maintenance of the malignancy.

Extensive catalogues of the cytogenetic aberrations in human cancer have been compiled and are maintained and regularly updated online (see The Mitelman Database of Chromosome Aberrations in Cancer at the US National Cancer Institute (NCI) Cancer Genome Anatomy Project (CGAP) Web site: http://cgap.nci.nih.gov). The database includes chromosomal aberrations for at least some of the malignancies of the present invention. The Wellcome Trust Sanger Institute Cancer Genome Project maintains a detailed online "Cancer Gene Census" of all human genes that have been causally linked to tumorigenesis (see http://www.sanger.ac.uk/genetics/CGP/Census) as well as the COSMIC (Catalogue of Somatic Mutations in Cancer) database of somatic mutations in human cancer (see http://www.sanger.ac.uk/genetics/CGP/cosmic). A further source containing abundant information on cytogenetic changes causally linked to various cancers is the Atlas of Genetics and Cytogenetics in Oncology and Haematology (http://atlasgeneticsoncoloy.org//Anomalies/Anomliste.html#MDS). These databases also include chromosomal aberrations for at least some of the malignancies of the present invention.

Diagnosis of cancerous malignancies by biopsy, immunophenotyping and other tests are known and routinely used.

In addition to high resolution chromosome banding and advanced chromosomal imaging technologies, chromosome aberrations in suspected cases of cancer can be determined through cytogenetic analysis such as fluorescence in situ hybridization (FISH), karyotyping, spectral karyotyping (SKY), multiplex FISH (M-FISH), comparative genomic hybridization (CGH), single nucleotide polymorphism arrays (SNP Chips) and other diagnostic and analysis tests known and used by those skilled in the art.

Antifolates interfere with the action of folates through inhibiting one or more targeted enzymes within the folic acid metabolism cycle and deprive cells of the DNA precursors required to proliferate. Cancer cells are fast-growing and thus have a high demand for DNA precursors, making them particularly susceptible to the effects of antifolates. Although acting through selective inhibition of AICARFT in the folic acid metabolism cycle, the compounds of Formula I are anticipated to be active against the same and similar cancers as the known antifolates including methotrexate, ralitrexed, pralatrexate, pemetrexed, as well as 5-fluorouracil. The cancer's against which the compounds of Formula I are anticipated to be active include: glioblastoma, cervical cancer, uterine cancer, breast cancer, triple negative breast cancer, bladder cancer, head and neck cancer, kidney cancer, melanoma, pancreatic cancer, liver cancer, lung cancer (including mesothelioma), colorectal cancer, gastric cancer, osteosarcoma, non-Hodgkin lymphoma (including T-cell lymphoma), fibroblastic sarcoma, chronic myelogenous leukemia, or acute lymphoid leukemia (ALL; including T-ALL, lymphoblast, and monocytic leukemia)

The following in vitro and in vivo studies demonstrate the inhibitory activity and efficacy of exemplified compounds of Formula I, or a pharmaceutically acceptable salt thereof, in inhibiting AICARFT, selectivity for inhibiting AICARFT, and in vivo antitumor activity. These assays are generally recognized by those skilled in the art as indicative of human clinical chemotherapeutic activity. Assays evidencing AICARFT inhibitory activity and efficacy may be carried out substantially as follows or by similar assays affording similar data.

Assays

In Vitro Antiproliferative Assay

Cloning & Enzyme Purification

Human AICARFT (NCBI accession number: NM_004044.6) cDNA is purchased from Openbiosystem Co. (Cat# MHS1011-62310, Clone ID: 4300570, accession: BC008879). The nucleotide sequence encoding full-length human AICARFT is inserted into pET21d (Novagen) vector with an N-terminal HIS tag. Bacterial BL21(DE3) (Novagen) is used as an expression host, and the induction of protein expression is carried out in 2×TY media with 1 mM IPTG at 18° C. overnight. Cell pellets are stored at −80° C. for subsequent protein purification. Protein purification is conducted at 4° C. Frozen cell pellets are lysed by incubation with stirring in 50 mL cold lysis buffer (50 mM Tris-HCl, pH 7.5, 300 mM NaCl, 10% glycerol, 0.1% Triton X-100, 0.5 mg/mL lysozyme, 5 U/mL benzonase, 1 mM DTT, 10 mM imidazole, and Roche complete EDTA-free protease inhibitor) per liter cell pellet and sonication. Cell lysates are clarified by centrifugation in a Bechman JA-18 rotor for 45 min at 16,500 rpm. The supernatant is incubated with Ni-NTA agarose resin (Qiagen) for 3 hours, followed by an initial batch wash with 10 resin volume of buffer A (50 mM Tris-HCl, pH 7.5, 300 mM NaCl, 10% glycerol, 1 mM DTT, 10 mM imidazole) containing 0.1% Triton X-100. The resin is then packed onto a column and washed with buffer A. The HIS-tagged AICARFT protein is eluted with 10-500 mM imidazole gradient in buffer A. Pooled HIS-AICARFT containing fractions are concentrated, loaded onto a HiLoad 26/600 Superdex 200 column (GE Healthcare Biosciences), and eluted with storage buffer (50 mM Tris-HCl, pH7.5, 150 mM NaCl, 1 mM DTT, 10% Glycerol). Fractions containing HIS-AICARFT are pooled and protein concentration determined by the Bradford assay using BSA as standard. The protein is aliquoted and stored at −80° C.

Tetrahydrofolate Substrate Synthesis

One of the substrates of the enzyme reaction, 10-formyltetrahydrofolate (10-F-THFA), has limited chemical stability and is therefore synthesized on the same day that the ATIC enzyme assay is performed. The general synthetic route is described in P. Rowe, Methods Enzymol., 18, 733-735, (1971) and J. Rabinowitz, Methods Enzymol., 6, 814-815, (1963). The first step in this synthesis is the conversion of folinic acid (Sigma CAS 1492-18-8) to 5,10-methenyltetrahydrofolic acid (5,10-M-THFA). This conversion typically takes place the day before the enzyme assay is performed, but can be performed up to 1 week earlier and stored at room temperature. To folinic acid (81.6 mg) is added β-mercaptoethanol (2 mL), and 37% concentrated HCl (80 μL), is added. This reaction incubates a minimum of 3 hours at room temperature, with occasional mixing. The color changes from clear to yellow visually, and the complete conversion of folinic acid to 5,10-M-THFA is monitored by spectral analysis using a quartz cuvette. The UV absorption will change from 266 nm to 356 nm during this step. This results in an 80 mM solution of 5,10-M-THFA. On the morning of the assay, the 80 mM 5,10-M-THFA is diluted to 1.6 mM in 40 μM ammonium bicarbonate (made fresh that day). This reaction incubates 3-5 hours at room temperature. The color changes from yellow to clear visually, and the conversion of 5,10-M-THFA to 10-F-THFA is monitored by spectral analysis using a quartz cuvette. The UV absorption will change from 356 nm to 258 nm during this step. This results in a 1.6 mM solution of 10-F-THFA. Test compounds are prepared in DMSO to make a 10 mM stock solution. The stock solution is serially diluted 3-fold in DMSO to obtain a ten-point dilution curve with final compound concentrations ranging from 100 μM to 5 nM. The final DMSO concentration in the assay is 5%.

Enzyme Assay Procedure

To each well of a 384-well polypropylene assay plate (NUNC 264573), 1 L of DMSO (control wells) or compound in DMSO and 9 μL of 55.56 μM ZMP (Sigma-Aldrich CAS 3031-94-5) in water are added. Then, 10 μL of 200 μM 10-F-THFA and 6 nM ATIC enzyme in 40 μM ammonium bicarbonate is added. Enzyme is omitted from wells used to define 100% inhibition. The final assay conditions are 25 μM ZMP, 100 μM 10-F-THFA, 3 nM ATIC enzyme, and 20 μM ammonium bicarbonate. The assay is incubated for 1 hour at room temperature, after which 40 μL of ACN is added to stop the reaction.

The inhibition of the AICARFT biochemical assay is determined by a liquid chromatography-mass spectrometry (LC-MS) method monitoring the signal from IMP and ZMP. The method utilized an Agilent RapidFire 300 chromatography system and an AB Sciex 6500™ triple quadrupole mass spectrometer with Analyst® 2.1 software. Biochemical samples are loaded onto a custom-packed polymeric weak anion exchange guard column using a sampling time of 0.6 seconds (approximately 30 μL) and loading buffer of 1 mM ammonium acetate in 10% ACN flowing at 1.25 mL/minute. Samples are washed for 1 second, and then eluted for 2 seconds using a 60:40 mixture of 20 mM ammonium acetate, pH 10 and ACN with a total flow rate of 1.25 mL/minute. Following elution, the column is re-equilibrated for 3000 msec with the loading buffer prior to starting the next injection. This system has a total cycle time of approximately 9 seconds/sample.

The mass spectrometer is operated in negative ion TurboIonSpray® multiple reaction monitoring mode with a source temperature of 750° C. The precursor and fragment ions for each analyte are: IMP (347→79) and ZMP (337→79). Peak areas for IMP and ZMP are determined using AB Sciex MultiQuant™ version 2.1. The IMP peak area divided by the sum of the IMP and ZMP peak areas is used to estimate the percent conversion of the reaction. The percent conversion is fit to a four-parameter logistic equation using ACTIVITYBASE 4.0 to determine $IC_{50}$ values. Specific values of activity representative of exemplified compounds tested in this assay are provided in Table 15.

TABLE 15

| Enzyme Assay | |
|---|---|
| Example # | $IC_{50}$ (nM) |
| 1 | 15.0 (±10.9, n = 9) |
| 8 | 13.8 (±7.0, n = 4) |
| 33 | 7.75 (±1.15, n = 3) |
| 41 | 10.6 (±3.1, n = 4) |
| 46 | 29.1 (±28.8, n = 6) |
| 81 | <5.08 |
| 84 | <5.08 |

Mean ± SEM;
SEM = standard error of the mean

The data in Table 15 demonstrates that the compounds of Examples 1, 8, 33, 41, 46, 81, and 84 inhibit AICARFT in this assay.

Low Folate Media

Supplement 500 mL Gibco folate free RPMI media (Gibco #27016-021) with 1 M Hepes (5 mL), 100 mM Na pyruvate (5 mL) and 0.5 g/mL glucose (2.5 mL) to match high folate ATCC RPMI media (ATCC #30-2001). To make complete media, both regular and folate free RPMI medias are supplemented with 10% FBS. The addition of FBS to folate free media adds low levels of folate and is now considered to be low folate media.

MS Detection of ZMP in Low Folate Media Cultured NCI H460 Cell

Grow NCI-H460 cells in complete high folate RPMI media (ATCC #30-2001) until cellular confluence reaches ~80%. Wash cells with PBS, trypsinize, resuspend cells in complete low folate RPMI media (Gibco #27016-021) and perform a cell count. Transfer $1.25 \times 10^6$ cells to a T225 flask containing complete low folate RPMI media (40 mL). Grow for seven days. Split cells again with complete low folate media if confluence surpasses 80%. Wash cells with PBS, trypsinize, resuspend cells in complete low folate RPMI media, and perform a cell count. Aliquot $10 \times 10^6$ cells in complete low folate media (1 mL)+5% DMSO per cryovial. Use a cell freezing apparatus to freeze cells in a slow and controlled manner in a $-80°$ C. freezer. The next day, transfer cells to liquid nitrogen for long term storage. Thaw frozen cells from cryovial in 37° C. water bath, wash cells once with low folate assay medium: folate free RPMI 1640 medium (Gibco, #27016-021), Glucose (Sigma, #G5767), Hepes (Hyclone, #SH30237.01), Na Pyruvate (Hyclone, #Sh30239.01), 10% FBS (Hyclone, #SH30070.03). Adjust cells concentration to 250,000 cells/mL with medium, plate cells by adding 100 µl/well (25,000 cells/well) into Biocoat poly-D-lysine 96-well plate (BD, #35-4640), and incubate at 37° C. overnight with 5% $CO_2$. Treat cells with 20 µl/well compound diluted in media containing 3% DMSO. Incubate at 37° C. for 16 hours with 5% $CO_2$, then remove the medium and add 1× SureFire Lysis Buffer (50 µL) (PerkinElem, SureFire® Kit component) to each well and incubate at room temperature for 10 min with gentle shaking.

The cellular effects of AICARFT inhibition on the concentrations of ZMP, 2'-deoxyuridine 5'-monophosphate (dUMP) and $N^1$-(β-D-Ribofuranosyl)-5-aminoimidazole-4-carboxamide (AICAr) are determined by LC-MS. Cells grown in a 96-well plate have the media removed and are lysed in AlphaScreen® SureFire® lysis buffer. Standard curves containing ZMP, dUMP and AICAr at concentrations of 5-10,000 ng/mL are prepared in 40 mM ammonium acetate, pH 4. Aliquots (40 µL) of each standard or sample are combined in a deep 96-well plate with 160 µL of internal standard solution containing $^{13}C_5$-ZMP (custom synthesis) and $^{13}C_5$-AICAr (custom synthesis) at 100 ng/mL in 40 mM ammonium acetate, pH 4. A Beckman Biomek FX liquid handler is used to add 400 µL of DCM to each sample. Samples are sealed, vortexed for 5 minutes, and placed in the refrigerator for at least 30 minutes. The samples are centrifuged for 10 minutes at 4,000 rpm and 4° C. using an Eppendorf 5810R centrifuge, and the Biomek liquid handler is used to transfer 75 µL of the aqueous layer into a clean 96-well plate. The plates are sealed prior to analysis.

The LC-MS method utilizes a Shimadzu Prominence 20A HPLC system connected to an AB Sciex 5500™ or an AB Sciex 6500™ triple quadrupole mass spectrometer running Analyst® 2.1 software. Extracted samples are separated using a Thermo Hypercarb™ Javelin guard column (2.1×20 mm, 5 m) with an injection volume of 15 µL and a flow rate of 1 mL/minute. Mobile phase A is a 95:5 mixture of 50 mM ammonium formate, pH 4 and ACN. Mobile phase B is a 70:30 mixture of ACN and MeOH spiked with 0.3% formic acid and 2% concentrated ammonium hydroxide solution (v/v). The gradient is as follows: 0 minutes, 0% B; 0.25 minutes, 0% B; 2.00 minutes, 30% B; 2.01 minutes, 95% B; 3.50 minutes, 95% B, 3.51 minutes, 0% B, 5.00 minutes, stop.

The mass spectrometer is operated in positive ion TurboIonSpray® multiple reaction monitoring mode with a source temperature of 700° C. The precursor and fragment ions for each analyte are: ZMP (339→110), $^{13}C_5$-ZMP (344→110), dUMP (309→81), AICAr (259→127) and $^{13}C_5$-AICAr (264→127). Calibration curves are constructed by plotting analyte concentrations vs. analyte/internal standard peak area ratios and performing a linear fit of the data using a 1/concentration weighting with AB Sciex MultiQuant™ 2.1 software. Back-calculated ZMP concentrations are fit to a four-parameter logistic equation using ACTIVITYBASE 4.0 to determine $IC_{50}$ values. Specific values of activity representative of exemplified compounds tested in this assay are provided in Table 16.

TABLE 16

Low Folate Media Assay

| Example # | $IC_{50}$ (nM) |
|---|---|
| 1 | 22.0 (±9.9, n = 7) |
| 8 | 25.0 (±22.1, n = 3) |
| 33 | 7.93 (±5.24, n = 7) |
| 41 | 42.2 (±18.8, n = 5) |
| 46 | 39.6 (±33.1, n = 6) |
| 81 | 10.2 (±8.6, n = 4) |
| 84 | 10.1 (±7.3, n = 5) |

Mean ± SEM;
SEM = standard error of the mean

The data in Table 16 demonstrates that although the presence of low levels of folate in the media modulate to some extent, the compounds of Examples 1, 8, 33, 41, 46, 81, and 84 still inhibit AICARFT in this assay.

In vitro Proliferation Assay

In vitro anti-proliferative activity of Examples 1 and 41 is determined by cell number counting assays against a panel of cell lines of adrenal gland, autonomic ganglia, biliary tract, blood ALL, blood AML, blood CML, blood hodgkin lymphoma, blood lymphoma, blood multiple myeloma, blood NHL, blood RAEB, bone, breast ER+, breast fibroblast, breast fibroblast mixed, breast HER2, breast normal, breast triple negative, cervix, CNS, endometrium, eye, fibroblast normal, kidney ns, kidney renal, large intestine, liver, liver normal, lung adenocarcinoma, lung ns, lung NSCLC, lung NSCLC mixed, lung SCLC, lung squamous, melanoma, melanoma normal, oesophagus adenocarcinoma, oesophagus ns, oesophagus squamous, ovary, pancreas adenocarcinoma, pancreas ductal carcinoma, pancreas ns, pleura mesothelioma, prostate adenocarcinoma, prostate small cell, salivary gland, small intestine, soft tissue, stomach, testis, thyroid, thyroid squamous, umbilical vein endothelial cell normal, upper aerodigestive tract squamous, urinary tract ns, urinary tract transitional cell carcinoma, and vulva squamous origin obtained from ATCC, CASTCC, CLS, DSMZ, ECACC, HSRRB, ICLC, JCRB, NCI, Riken and SNU cell banks. Cells are grown using the cell banks recommended culture conditions on the date of sample acquisition. Prepare complete medium adding appropriate horse serum (ex. Invitrogen, Cat. No. 16050130) or FBS (ex. Invitrogen, Cat. No. 10099-141 or Hyclone Cat. No. CH30160.03) and additives.

For attached cell lines, remove and discard culture medium using a vacuum pump. Briefly rinse the cell layer with 0.25% (w/v) Trypsin-0.038% (w/v) EDTA solution to remove all traces of serum that contains trypsin inhibitor. Add 3.0 mL of Trypsin-EDTA solution to flask and observe cells under an inverted microscope until cell layer is dispersed. Add 8.0 mL of complete growth medium and aspirate cells by gently pipetting.

For suspension cell lines, transfer the cell suspension to a centrifuge tube and centrifuge at 800-1000 rpm for 3-5 minutes. Discard the supernatant using a vacuum pump. Add the appropriate volume of complete medium. Suspend the cell pellet by gently pipetting. Count the cell numbers and adjust cells to the appropriate seeding density. Add 100 µl (for the cells that will be tested for 48, 96 and 120 hours) or 200 µl (for the cells that will be tested for 144 hours) of cell suspension to 96-well white-walled clear bottom plates (ex. Corning, Cat. No. 3707 or 3610) according to the planned plate layout and place the plates in the $CO_2$ incubator overnight.

Prepare 2 mM DMSO stocks of compounds to be tested in proliferation assay. Determine the concentrations to be tested and dilute the compounds to 200×final concentration in low folate media. DMSO is the diluent. Perform a serial 1:3 dilution of compounds in diluent. Add 0.5 or 1 µl/well of diluted compounds to plated cells. Final concentration of compounds will be 1×. Incubate plates at 37° C. for approximately 2 doubling times as determined for each cell line. Observe the cell morphology under an inverted microscope. Equilibrate the plate and its contents to room temperature for approximately 30 minutes. Add 100 µl of CellTiter-Glo Reagent (Promega, Cat. No. G7571) to the assay plate. Mix contents for 2 minutes on an orbital shaker to induce cell lysis. Allow the plate to incubate at room temperature for 10 minutes to stabilize luminescent signal. Paste the clear bottom with white back seal and record luminescence with Flexstation3 (Molecular Devices). The settings should be: Luminescence, integration time 500 ms. Determine % inhibition for each sample (see Table 17).

TABLE 17

Proliferation Assay

| | Number of Cell Lines | | | | | |
|---|---|---|---|---|---|---|
| | Example 1 | | | Example 41 | | |
| | | | | | Rel IC$_{50}$ | Rel IC$_{50}$ |
| Histology | Total count | Rel IC$_{50}$ ≤2.50 µM and % inh ≥50 | Rel IC$_{50}$ >2.50 µM or % inh <50 | Total count | ≤2.50 µM and % inh ≥50 | >2.50 µM or % inh <50 |
| Adrenal_Gland | 2 | | 2 | 2 | | 2 |
| Autonomic_Ganglia | 7 | 2 | 5 | 7 | 1 | 6 |
| Biliary_Tract | 3 | 1 | 2 | 3 | 1 | 2 |
| Blood_ALL | 14 | 10 | 4 | 14 | 7 | 7 |
| Blood_AML | 9 | 5 | 4 | 9 | 3 | 6 |
| Blood_CML | 3 | 3 | | 3 | 3 | |
| Blood_Hodgkin_lymphoma | 1 | | 1 | 1 | | 1 |
| Blood_lymphoma | 2 | 2 | | 2 | 2 | |
| Blood_multiple_myeloma | 6 | 2 | 4 | 6 | 2 | 4 |
| Blood_NHL | 19 | 11 | 8 | 19 | 10 | 9 |
| Blood_RAEB | 1 | 1 | | 1 | 1 | |
| Bone | 12 | | 12 | 10 | | 10 |
| Breast_ER_plus | 6 | 1 | 5 | 5 | | 5 |
| Breast_fibroblast | 1 | | 1 | 1 | | 1 |
| Breast_fibroblast_mixed | 1 | | 1 | 1 | | 1 |
| Breast_HER2 | 12 | 4 | 8 | 12 | 2 | 10 |
| Breast_normal | 1 | | 1 | 1 | | 1 |
| Breast_TNBC | 17 | 5 | 12 | 16 | 4 | 12 |
| Cervix | 8 | 1 | 7 | 8 | 1 | 7 |
| CNS | 16 | 5 | 11 | 16 | 4 | 12 |
| Endometrium | 6 | | 6 | 6 | | 6 |
| Eye | 1 | | 1 | 1 | | 1 |
| Fibroblast_normal | 1 | 1 | | 1 | 1 | |
| Kidney_NS | 8 | 3 | 5 | 8 | 2 | 6 |
| Kidney_Renal | 13 | 5 | 8 | 13 | 4 | 9 |
| Large_Intestine | 28 | 11 | 17 | 28 | 10 | 18 |
| Liver | 30 | 6 | 24 | 30 | 4 | 26 |
| Liver_normal | 2 | | 2 | 2 | | 2 |
| Lung_Adenocarcinoma | 49 | 10 | 39 | 49 | 8 | 41 |
| Lung_NS | 2 | | 2 | 2 | | 2 |
| Lung_NSCLC | 5 | | 5 | 5 | | 5 |
| Lung_NSCLC_mixed | 2 | 1 | 1 | 2 | 1 | 1 |
| Lung_SCLC | 28 | 5 | 23 | 28 | 3 | 25 |
| Lung_Squamous | 9 | 2 | 7 | 9 | 1 | 8 |
| Melanoma | 33 | 6 | 27 | 33 | 6 | 27 |
| Melanoma_normal | 1 | | 1 | 1 | | 1 |
| Oesophagus_Adenocarcinoma | 2 | | 2 | 2 | | 2 |
| Oesophagus_NS | 2 | | 2 | 2 | | 2 |
| Oesophagus_Squamous | 15 | 11 | 4 | 15 | 10 | 5 |
| Ovary | 10 | 4 | 6 | 10 | 4 | 6 |
| Pancreas_Adenocarcinoma | 7 | 1 | 6 | 7 | | 7 |
| Pancreas_Ductal_Carcinom | 5 | 2 | 3 | 5 | 3 | 2 |

TABLE 17-continued

Proliferation Assay

| | Number of Cell Lines | | | | | |
|---|---|---|---|---|---|---|
| | | Example 1 | | | Example 41 | |
| | | Rel IC$_{50}$ ≤2.50 µM | Rel IC$_{50}$ >2.50 µM | | Rel IC$_{50}$ ≤2.50 µM | Rel IC$_{50}$ >2.50 µM |
| Histology | Total count | and % inh ≥50 | or % inh <50 | Total count | and % inh ≥50 | or % inh <50 |
| Pancreas_NS | 3 | 1 | 2 | 3 | | 3 |
| Pleura_Mesothelioma | 4 | | 4 | 4 | | 4 |
| Prostate_Adenocarcinoma | 5 | | 5 | 5 | | 5 |
| Prostate_Small_Cell | 1 | | 1 | 1 | | 1 |
| Salivary_gland | 2 | | 2 | 2 | | 2 |
| Small_intestine | 1 | 1 | | 1 | 1 | |
| Soft_Tissue | 8 | 1 | 7 | 8 | 2 | 6 |
| Stomach | 30 | 9 | 21 | 30 | 5 | 25 |
| Testis | 1 | 1 | | 1 | | 1 |
| Thyroid | 2 | | 2 | 2 | | 2 |
| Thyroid_Squamous | 1 | | 1 | 1 | | 1 |
| Umbilical_vein_endothelial_cell_Normal | 1 | | 1 | 1 | | 1 |
| Upper_aerodigestive_tract_Squamous | 12 | 4 | 8 | 12 | 1 | 11 |
| Urinary_tract_NS | 2 | 2 | | 2 | | 2 |
| Urinary_tract_Transitional_Cell_Carcinoma | 7 | 3 | 4 | 7 | 3 | 4 |
| Vulva_Squamous | 2 | | 2 | 2 | | 2 |
| Total | 482 | 143 | 339 | 478 | 109 | 369 |

The data in Table 17 demonstrates that the compounds of Example 1 and 41 tested in this assay inhibit proliferation of cancer cells under standard media conditions. As representative data from this assay, Example 1 and Example 41 in one of the 49 Lung Adenocarcinoma cell lines evaluated demonstrated an IC$_{50}$ of 0.61 µM and 1.88 µM respectively for large cell lung cancer NCI-H460 and in one of the 28 Large Intestine cell lines demonstrated an IC$_{50}$ of 8.1 µM and 10.8 µM respectively for colorectal carcinoma HCT-116, under standard media conditions.

Low Folate In Vitro Proliferation Assay

In vitro anti-proliferative activity of Example 1 is determined by cell number counting assays against a panel of 46 cancer cell lines of lung, colorectal, gastric, pancreatic, liver, breast, brain, melanoma, pancreatic, fibrosarcoma, kidney, T-cell leukemia, lymphoblast, monocyte & CML origin obtained from ATCC, DSMZ, JCRB, and Riken cell banks. Transfer cells growing in high folate RPMI media (ATCC #30-2001)+10% FBS (Hyclone #SH30070.03) to low folate RPMI media and folate starve for 7 days. Wash cells grown in high folate media with PBS, trypsinize, and resuspend in low folate media. Grow cells in low folate media for 7 days making sure to seed tissue culture flasks at a density that will not exceed 80% confluence after 7 days. Wash cells in PBS, trypsinize, and resuspend in low folate media and count cells. Seed 96 well poly D lysine plate (Corning #354640) at 3000 cells/well in 100 µl low folate media. Allow cells to attach overnight. Prepare 10 mM DMSO stocks of compounds to be tested in proliferation assay. Determine concentrations to be tested and dilute compounds to 2× final concentration in low folate media. Calculate % DMSO of this solution and use this value as diluent. Perform a serial 1:2 or 1:3 dilution of compounds in diluent. Add 100 µl/well of diluted compounds to plated cells. Final concentration of compounds will be 1×. Ensure that final % DMSO does not exceed 0.5%. Maximum and minimum signal reference controls are reserved for columns #1 (2 µM Staurosporine) and column #12 (DMSO at diluent concentration). Dose cells with compounds of interest for 7 days. To measure proliferation results, add 1/10 volume Alamar Blue cell viability reagent (Invitrogen DAL-1100) to each well. Return plate to tissue culture incubator and allow reaction to proceed for approximately 1.5-4 hours. Read plates on the Envision plate reader (Perkin Elmer), or other fluorescent plate reader, with excitation at 570 nm and emission at 585 nm. Determine % inhibition for each sample (see Table 18).

TABLE 18

In vitro anticancer activity of Example 1 in low folate media

| Cancer Cell Lines | Number of Cell Lines | Number of cell lines | |
|---|---|---|---|
| | | >50% Inhibition relative IC$_{50}$ < 20 nM | <50% Inhibition relative IC$_{50}$ > 20 nM |
| Lung | 21 | 14 | 7 |
| Gastro-intestinal | 6 | 4 | 2 |
| Pancreatic | 4 | 2 | 2 |
| Melanoma | 3 | 1 | 2 |
| Brain | 3 | 2 | 1 |
| Breast | 3 | 0 | 3 |
| Others | 9 | 4 | 5 |
| Total | 49 | 27 | 22 |

The data in Table 18 demonstrates that Example 1, the exemplified compound tested in this assay, inhibits proliferation of cancer cells under media conditions with folate levels similar to human plasma. As representative data from this assay, Example 1 in one of the 21 Lung cell lines evidenced an IC$_{50}$ of 20 nM for large cell lung cancer NCI-H460, and in one of the 6 Gastrointestinal cell lines evidenced an IC$_{50}$ of 3 nM for, the colorectal carcinoma HCT-116, in low folate media.

Antitumor Efficacy in Human Carcinoma Mouse Xenograft Model

The in vivo anticancer activity of Example 1 is studied in human colorectal adenocarcinoma cell line HCT-116 and human lung carcinoma NCI-H460 mouse xenograft tumor model which is predicted to be sensitive based on in vitro proliferative assay data described above. In vivo studies are performed using female athymic nude mice (Harlan) with a bodyweight of 23-28 g at first measurement. Upon receipt and throughout the study, the animals are housed 5 animals per cage in appropriately sized solid-bottom cages with contact bedding. The animal room is maintained on a 12-hour light/dark cycle. Animals are acclimated for 14 days prior to implantation of the NCI-H460 or HCT-116 cells on low folate diet (Teklad 130451) ad libitum and autoclaved tap water is provided ad libitum. The HCT-116 and NCI-H460 cell line are obtained from American Type Culture Collection (ATCC) and is cultured following ATCC instructions. Cells used for implantation are harvested during log phase growth and suspended in serum-free media. The suspended cells are then diluted 1:1 with BD Matrigel Matrix (ref 354234). Cells are injected in the right flank with 5.0E+06 cells (0.2 mL cell/Matrigel suspension). Tumors are monitored beginning day 8 post implant. Animals are redistributed into groups with 5-6 animals per group utilizing proprietary randomization software when average tumor volume reaches 200 $mm^3$. Groups 1-12 are maintained on a low folate diet (Teklad 130451) and folic acid (Sigma F8798 Lot #SLBH0909V) administration at doses listed in the Table 19 began 28 hours prior to dose initiation and 4 hours prior to each dose. Folic acid is formulated weekly in PBS and dosed via oral gavage at 0.2 mL. Groups 13-16 are placed on standard chow (Teklad 2920X) at randomization. The compound is formulated weekly in 20% HPBCD in Phosphate buffer pH 8 with one molar equivalent NaOH added. The formulated compound is administered at the doses and schedules indicated in Table 19 by oral gavage (0.2 mL). The vehicle is also given QD as the control arm of the study. Tumor volume and body weight are measured 2× a week. Tumor volume is determined by caliper measurements (mm) and using the formula for an ellipsoid sphere: tumor volume ($mm^3$)=length×$width^2$/2, where length and width refer to the larger and smaller perpendicular dimensions collected at each measurement. The animal behavior and animal health are monitored daily during dosing period. The study is terminated after the last dose indicated in Table 19.

The statistical analysis of the tumor volume data begins with a data transformation to a log scale to equalize variance across time and treatment groups. The log volume data are analyzed with a two-way repeated measures analysis of variance by time and treatment using the MIXED procedures in SAS software (Version 9.3). The correlation model for the repeated measures is Spatial Power. Treated groups are compared to the control group at each time point. The MIXED procedure is also used separately for each treatment group to calculate adjusted means and standard errors at each time point. Both analyses account for the autocorrelation within each animal and the loss of data that occurs when animals with large tumors are removed from the study early. The adjusted means and standard errors are plotted for each treatment group vs time. The analysis comparing the treated groups to the control groups at each time point uses the log 10 tumor volumes and produces the p-values. For statistical significance of p-values shown, "*"=P<0.05.

Delta T/C, % calculation is used. Equations: T=Final tumor volume in treated group; T0=Baseline tumor volume in treated group (assumed to be same as C0); C=Final tumor volume in control group; C0=Baseline tumor volume in control group (assumed to be same as T0); Delta T/C, %=100*(T−T0)/(C−C0)

AICARFT In Vivo Target Inhibition (IVTI) Assay

The in vivo effects of AICARFT inhibition on the concentrations of pathway-related analytes are determined by liquid chromatography-mass spectrometry (LC-MS) analysis of tumor xenografts. Tumor xenograft samples on dry ice are weighed on an analytical balance, transferred to 2 mL Eppendorf Safe-Lock Tube™, and placed on dry ice. An internal standard solution containing 13C5-ZMP (1000 ng/mL), 13C5-AICAr (500 ng/mL), ascorbic acid (0.1%), and formic acid (0.1%) in MeOH/DCM (80:20) is prepared and stored at 20° C. For every mg of tissue in the sample tube, 10 L of internal standard solution is added. Standard curves containing ZMP, dUMP, AICAr at concentrations of 7.6-50,000 ng/mL are prepared separately in the internal standard solution.

One 5 mm steel bead (Qiagen) is added to each sample tube and the tubes are placed on wet ice for 15 minutes. Samples are homogenized on a Qiagen TissueLyser II for 5 minutes at 15 Hz, and then centrifuged on an Eppendorf 5430R microcentrifuge for 10 minutes at 13,000 rpm and 4° C. Aliquots of each supernatant (200 µL) are removed and placed into a deep 96-well plate. Aliquots (200 µL) of each standard curve solution are also placed in a deep 96-well plate. A Beckman Biomek FX liquid handler added DCM (600 µL) and 0.1% ascorbic acid solution (200 µL) to each well. The plate is sealed, vortexed for 5 minutes, and centrifuged for 5 minutes at 4,000 rpm and 4° C. on an Eppendorf 5810R centrifuge. Aliquots (75 µL) of the top layer are transferred to a clean 96-well plate, and an additional 75 µL of 40 mM ammonium acetate, pH 4 is added to each well. The plates are sealed prior to analysis. The LC-MS method utilized a Shimadzu Prominence 20A HPLC system connected to an AB Sciex 5500™ or an AB Sciex 6500™ triple quadrupole mass spectrometer running Analyst® software. Extracted samples are separated using two Thermo Hypercarb™ Javelin guard columns (2.1×20 mm, 5 µm) connected in series with an injection volume of 15 µL and a flow rate of 0.75 mL/minute. Mobile phase A is a 95:5 mixture of 50 mM ammonium formate, pH 4 and ACN. Mobile phase B is a 70:30 mixture of ACN and MeOH spiked with 0.3% formic acid and 2% concentrated ammonium hydroxide solution (v/v). The gradient is as follows: 0 minutes, 0% B; 0.25 minutes, 0% B; 4.00 minutes, 30% B; 4.01 minutes, 95% B; 5.50 minutes, 95% B, 3.51 minutes, 0% B, 7.50 minutes, stop. The mass spectrometer is operated in positive ion TurboIonSpray® multiple reaction monitoring mode with a source temperature of 700° C. The precursor and fragment ions for each analyte are: ZMP (339→110), 13C5-ZMP (344→110), dUMP (309→81), AICAr (259→127), and 13C5-AICAr (264→127). Calibration curves are constructed by plotting analyte concentrations vs. analyte/internal standard peak area ratios and performing a linear fit of the data using a 1/concentration weighting with AB Sciex MultiQuant™ 2.1 software. 13C5-ZMP is used as the internal standard for ZMP and dUMP. 13C5-AICAr is s used as the internal standard for AICAr.

AICARFT In Vivo Target Inhibition (IVTI) Assay in Mouse and Dog Plasma

The in vivo effects of AICARFT inhibition on the circulating concentration of AICAr is determined by liquid chromatography-mass spectrometry (LC-MS). Standard curves containing AICAr at concentrations of 1 ng/mL-2000 ng/mL are prepared in 40 mM ammonium acetate, pH 4. Plasma samples (75 µL) or standards (75 µL) are combined with 300 µL of an internal standard solution containing 13C5-AICAr (20 ng/mL) and formic acid (1%) in ACN. The samples are vortex mixed for 5 minutes and passed through a Phenomenex Phree 96-well phospholipid removal SPE plate. The eluents are collected in a 96-well plate and dried under heated nitrogen at 50° C. Each sample is reconstituted in 50 µL of 40 mM ammonium acetate, pH 4. The plates are sealed and vortexed for 5 minutes prior to analysis. The LC-MS method utilized a Shimadzu Prominence 20A HPLC system connected to an AB Sciex 5500™ or an AB Sciex 6500™ triple quadrupole mass spectrometer running Analyst® software. Extracted samples are separated using two Thermo Hypercarb™ Javelin guard columns (2.1×20 mm, 5 µm) connected in series with an injection volume of 15 µL and a flow rate of 1 mL/minute. Mobile phase A is a 95:5 mixture of 50 mM ammonium formate, pH 4 and ACN. Mobile phase B is a 70:30 mixture of ACN and MeOH spiked with 0.3% formic acid and 2% concentrated ammonium hydroxide solution (v/v). For mouse plasma samples the following gradient is used: 0 minutes, 0% B; 0.25 minutes, 0% B; 2.00 minutes, 25% B; 2.01 minutes, 95% B; 3.50 minutes, 95% B; 3.51 minutes, 0% B; 4.50 minutes, stop. For dog plasma samples the following gradient is used to remove endogenous interferences: 0 minutes, 0% B; 0.25 minutes, 0% B; 5.99 minutes, 20% B; 6.00 minutes, 95% B; 8.00 minutes, 95% B; 8.01 minutes, 0% B; 10.00 minutes, stop. The mass spectrometer is operated in positive ion TurboIonSpray® multiple reaction monitoring mode with a source temperature of 700° C. The precursor and fragment ions for each analyte are: AICAr (259→127) and 13C5-AICAr (264→127). Calibration curves are constructed by plotting analyte concentrations vs. analyte/internal standard peak area ratios and performing a linear fit of the data using a 1/concentration weighting with AB Sciex MultiQuant™ 2.1 software.

TABLE 19

Antitumor activity in mouse xenograft tumor model and IVTI

| Group | Cells | Folic Acid Dose | Example # | Compound Dose | Day | % T/C | Mean tumor ZMP, µM | Mean plasma AICAr, nM |
|---|---|---|---|---|---|---|---|---|
| 13 | NCI-H460 | | Vehicle | | 20 | | 0.1 | 8.4 |
| 14 | NCI-H460 | | 1 | 10 mg/kg QD × 13, orally | 20 | 113 | 3.7 | 368 |
| 15 | NCI-H460 | | 1 | 30 mg/kg QD × 13, orally | 20 | 42* | 66 | 1400 |
| 5 | HCT-116 | 0.75 mg/kg (QD × 15, orally) | Vehicle | | 23 | | 0.2 | 1.5 |
| 6 | HCT-116 | 0.75 mg/kg (QD × 15, orally) | 1 | 10 mg/kg QD × 14, orally | 23 | 65* | 20 | 88 |
| 7 | HCT-116 | 0.75 mg/kg (QD × 15, orally) | 1 | 30 mg/kg QD × 14, orally | 23 | 57* | 35 | 181 |
| 13 | HCT-116 | | Vehicle | | 23 | | 0.2 | 1.5 |
| 14 | HCT-116 | | 1 | 10 mg/kg QD × 14, orally | 23 | 112 | 7.0 | 44 |
| 15 | HCT-116 | | 1 | 30 mg/kg QD × 14, orally | 23 | 49 | 26 | 154 |

As provided in Table 19 above, the exemplified compound of Example 1 tested in this assay demonstrates in vivo anticancer activity on the HCT-116 & NCI-H460 xenograft tumors when given QD continuously for 2 weeks. This activity is consistent with the in vitro activity observed with HCT-116 & NCI-H460 cancer cell lines. The mouse has serum folate levels significantly higher than humans (C P Leamon et al. (2008) JPET 327:918-925) and may underestimate the activity observed in humans based upon the dependence of anti-proliferative $IC_{50}$ on the folate levels in tissue culture. The observed tumor growth inhibition activity is associated with increases in tumor ZMP and plasma AICAr. The data in Table 19 also supports the use of plasma AICAr as a biomarker for AICARFT inhibition.

Pharmacodynamic Response in Beagle Dogs

Pharmacodynamic (PD) response to Example 1, Example 33, and Example 41 are assessed in the most relevant non-clinical species in single ascending dose studies in beagle dogs. Beagle dogs, non-human primates and human are low serum folate species, whereas rodents are high serum folate (C P Leamon et al. (2008) JPET 327:918-925). The pharmacodynamics response in dogs treated with an AICARFT inhibitor will be more representative of the expected pharmacodynamics response in patients treated with an AICARFT inhibitor.

To demonstrate target engagement in "normal", i.e. non-tumour bearing, pairs of non-naïve beagle dogs are treated with an AICARFT inhibitor by oral gavage administration; each experiment included two pairs of one male and one female dog which are treated on alternate occasions—each pair of dogs received two treatments at least seven days apart.

Following treatment, plasma samples are taken at timed intervals for measurement of pharmacodynamics response as demonstrated by increased plasma AICAr concentrations. Animals are returned to the colony for re-use after completion of the experiment.

TABLE 20

| Plasma AICAr elevation in beagle dogs | | | |
|---|---|---|---|
| Example # | Dose | Time of collection post dose | Mean Plasma AICAr nM |
| 1 | 10 mg/kg QD, orally | 8 | 138 |
| 1 | 30 mg/kg QD, orally | 8 | 254 |
| 1 | 100 mg/kg QD, orally | 8 | 652 |
| 1 | 300 mg/kg QD, orally | 8 | 931 |
|  | Vehicle, orally | 0 | 18 |
| 33 | 10 mg/kg QD, orally | 8 | 98 |
| 33 | 30 mg/kg QD, orally | 8 | 213 |
| 33 | 100 mg/kg QD, orally | 8 | 726 |
| 33 | 300 mg/kg QD, orally | 8 | 1150 |
|  | Vehicle, orally | 0 | 12 |
| 41 | 10 mg/kg QD, orally | 8 | 158 |
| 41 | 30 mg/kg QD, orally | 8 | 362 |
| 41 | 100 mg/kg QD, orally | 8 | 1534 |
| 41 | 300 mg/kg QD, orally | 8 | 1373 |

As provided in Table 20, the compound of Example 1, Example 41, and Example 33 tested in this assay demonstrate in vivo inhibition of AICARFT in dogs. This activity in dogs is consistent with the in vivo activity of these compounds observed in the HCT-116 and NCI-H460 mouse xenograft evaluations, above.

We claim:

1. A compound of Formula I:

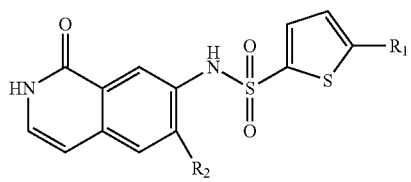

I wherein:
$R^1$ is selected from the group:

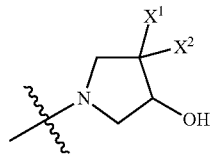

wherein each of $X^1$ and $X^2$ is independently selected from hydrogen, fluoro, or —$CH_3$;
or one of $X^1$ and $X^2$ is selected from —OH, —$OCH_3$, —$N(CH_3)_2$ or morpholin-4-yl and the other is hydrogen;

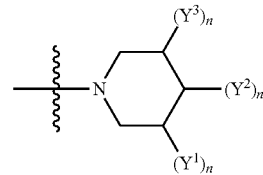

wherein each n is independently selected from 0, 1 or 2;
$Y^1$, $Y^2$ and $Y^3$ are independently selected from hydrogen, —OH, fluoro, —$NH_2$, or —$CF_3$; provided all are not hydrogen; and
provided all n's are not simultaneously 0; and further provided only one n may be 2;
and when one n is 2, each of $Y^1$, $Y^2$ and $Y^3$ are independently selected from fluoro, —OH, or —$CF_3$;

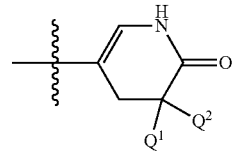

wherein $Q^1$ and $Q^2$ are independently selected from hydrogen, —$CH_3$ or —$CH_2CH_3$;

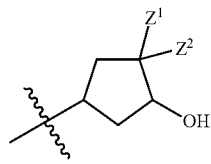

wherein each of $Z^1$ and $Z^2$ is independently selected from hydrogen or fluoro;

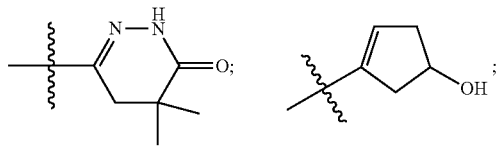

-continued

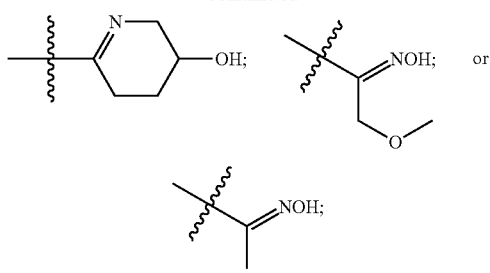

$R^2$ is hydrogen or fluoro;
or a pharmaceutically acceptable salt thereof.

2. A compound as claimed in claim 1 wherein:
$R^1$ is selected from the group:

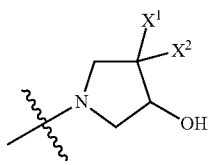

wherein each of $X^1$ and $X^2$ is independently selected from hydrogen, fluoro, or —CH$_3$; or one of $X^1$ and $X^2$ is selected from —OH, —OCH$_3$, —N(CH$_3$)$_2$ or morpholin-4-yl and the other is hydrogen;

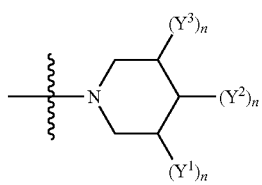

wherein each n is independently selected from 0, 1 or 2;
$Y^1$, $Y^2$ and $Y^3$ are independently selected from hydrogen, —OH, fluoro, —NH$_2$, or —CF$_3$; provided all are not hydrogen; and provided all n's are not simultaneously 0; and further provided only one n may be 2; and when one n is 2, each of $Y^1$, $Y^2$ and $Y^3$ are independently selected from fluoro, —OH, or —CF$_3$;

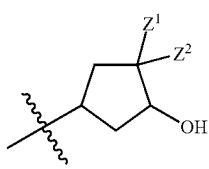

wherein each of $Z^1$ and $Z^2$ is independently selected from hydrogen or fluoro;

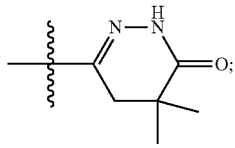 [SMILES: *C1=NNC(=O)C(C)(C)C1]

$R^2$ is hydrogen or fluoro;
or a pharmaceutically acceptable salt thereof.

3. A compound as claimed in claim 2 wherein:
$R^1$ is selected from the group:

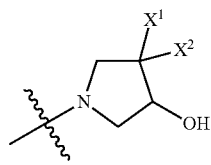

wherein each of $X^1$ and $X^2$ is independently selected from hydrogen, fluoro, or CH$_3$;

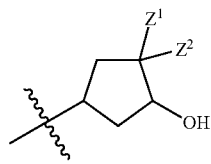

wherein each of $Z^1$ and $Z^2$ is independently selected from hydrogen or fluoro;

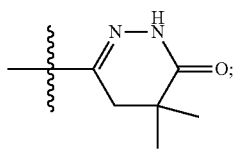 [SMILES: *C1=NNC(=O)C(C)(C)C1]

$R^2$ is fluoro;
or a pharmaceutically acceptable salt thereof.

4. A compound as claimed in claim 3 wherein the compound is:
N-(6-Fluoro-1-oxo-1,2-dihydroisoquinolin-7-yl)-5-[(3R)-3-hydroxypyrrolidin-1-yl]thiophene-2-sulfonamide, or a pharmaceutically acceptable salt thereof;
N-(6-Fluoro-1-oxo-1,2-dihydroisoquinolin-7-yl)-5-[(3S)-3-hydroxypyrrolidin-1-yl]thiophene-2-sulfonamide, or a pharmaceutically acceptable salt thereof;
5-[(3S,4R)-3-Fluoro-4-hydroxy-pyrrolidin-1-yl]-N-(6-fluoro-1-oxo-1,2-dihydroisoquinolin-7-yl)thiophene-2-sulfonamide, or a pharmaceutically acceptable salt thereof;
5-(3,3-Difluoro-(4R)-4-hydroxy-pyrrolidin-1-yl)-N-(6-fluoro-1-oxo-1,2-dihydroisoquinolin-7-yl)thiophene-2-sulfonamide, or a pharmaceutically acceptable salt thereof;
5-(5,5-Dimethyl-6-oxo-1,4-dihydropyridazin-3-yl)-N-(6-fluoro-1-oxo-1,2-dihydroisoquinolin-7-yl)thiophene-2-sulfonamide, or a pharmaceutically acceptable salt thereof; or N-(6-Fluoro-1-oxo-1,2-dihydroisoquinolin-7-yl)-5-[(1R,3R)-3-hydroxycyclopentyl]thiophene-2-sulfonamide, or a pharmaceutically acceptable salt thereof.

5. A compound as claimed in claim 4 wherein the compound is:
N-(6-Fluoro-1-oxo-1,2-dihydroisoquinolin-7-yl)-5-[(3R)-3-hydroxypyrrolidin-1-yl]thiophene-2-sulfonamide, or a pharmaceutically acceptable salt thereof.

6. A pharmaceutical composition comprising a compound of claim 1, or a pharmaceutically acceptable salt thereof, with a pharmaceutically acceptable carrier.

7. A method of treating a cancer which is glioblastoma, cervical cancer, uterine cancer, breast cancer, triple negative breast cancer, bladder cancer, head and neck cancer, kidney cancer, melanoma, pancreatic cancer, liver cancer, lung cancer, mesothelioma, colorectal cancer, gastric cancer, osteosarcoma, non-Hodgkin lymphoma, T-cell lymphoma, fibroblastic sarcoma, chronic myelogenous leukemia, acute lymphoid leukemia, T-ALL, lymphoblast, or monocytic leukemia in a patient comprising administering to a patient in need thereof a therapeutically effective amount of a compound of claim 1, or a pharmaceutically acceptable salt thereof.

8. A method of treating a cancer which is triple negative breast cancer, bladder cancer, lung cancer, mesothelioma, colorectal cancer, non-Hodgkin lymphoma, T-cell lymphoma, chronic myelogenous leukemia, acute lymphoid leukemia, T-ALL, lymphoblast, or monocytic leukemia) in a patient comprising administering to a patient in need thereof a therapeutically effective amount of a compound of claim 1, or a pharmaceutically acceptable salt thereof.

* * * * *

UNITED STATES PATENT AND TRADEMARK OFFICE
CERTIFICATE OF CORRECTION

PATENT NO. : 9,776,992 B2
APPLICATION NO. : 15/518787
DATED : October 3, 2017
INVENTOR(S) : Harold Burns Brooks Page 1 of 1

It is certified that error appears in the above-identified patent and that said Letters Patent is hereby corrected as shown below:

In the Claims

In Column 95, Lines 1 through 5 (structure), Claim 1 delete ". 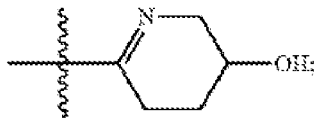 " and insert --  --, therefor.

In Column 97, Line 28, Claim 8 delete "leukemia)" and insert -- leukemia --, therefor.

Signed and Sealed this
Twelfth Day of December, 2017

Joseph Matal
*Performing the Functions and Duties of the*
*Under Secretary of Commerce for Intellectual Property and*
*Director of the United States Patent and Trademark Office*